US012734258B2

(12) United States Patent
Zeglis et al.

(10) Patent No.: US 12,734,258 B2
(45) **Date of Patent: *Sep. 15, 2026**

(54) RADIOLIGANDS FOR PRETARGETED PET IMAGING AND METHODS OF THEIR THERAPEUTIC USE

(71) Applicant: Memorial Sloan Kettering Cancer Center, New York, NY (US)

(72) Inventors: Brian Zeglis, New York, NY (US); Jason Lewis, New York, NY (US); Thomas Reiner, New York, NY (US); Jacob Lee Houghton, New York, NY (US); Jan-Philip Meyer, New York, NY (US); Christian Brand, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1326 days.

This patent is subject to a terminal disclaimer.

(21) Appl. No.: 17/464,472

(22) Filed: Sep. 1, 2021

(65) Prior Publication Data

US 2022/0040337 A1 Feb. 10, 2022

Related U.S. Application Data

(63) Continuation of application No. 16/203,513, filed on Nov. 28, 2018, now Pat. No. 11,135,320, which is a continuation of application No. 14/826,775, filed on Aug. 14, 2015, now abandoned.

(60) Provisional application No. 62/159,763, filed on May 11, 2015.

(51) Int. Cl.

| | |
|---|---|
| ***A61K 51/00*** | (2006.01) |
| ***A61K 47/68*** | (2017.01) |
| ***A61K 51/04*** | (2006.01) |
| ***A61M 36/14*** | (2006.01) |

(52) U.S. Cl.
CPC ...... *A61K 51/0482* (2013.01); *A61K 47/6897* (2017.08); *A61K 51/0453* (2013.01)

(58) Field of Classification Search
CPC ............ A61K 51/0482; A61K 47/6897; A61K 51/0453
See application file for complete search history.

(56) References Cited

U.S. PATENT DOCUMENTS

| | | | | |
|---|---|---|---|---|
| 11,135,320 | B2 * | 10/2021 | Zeglis ................ | A61K 51/0482 |
| 2012/0039803 | A1 * | 2/2012 | Robillard ........... | A61K 51/1045 424/9.1 |
| 2012/0134920 | A1 | 5/2012 | D'Souza et al. | |
| 2014/0093522 | A1 * | 4/2014 | Robillard ............... | A61K 47/22 530/391.9 |
| 2015/0359913 | A1 * | 12/2015 | Reiner ............... | A61K 51/0453 424/9.4 |

OTHER PUBLICATIONS

Rossin et al. (Bioconj. Chem. 2013, 24, 1210-1217).*
Minretumomab Wikipedia (2025).*
Blom et al. (Int. J. Clin. Exp. Med. 2012, 5, 165-172).
Fournier et al. (Bioconj. Chem. 2012, 23, 1687-1693).
Kai Chen et al: "Combining aluminum [18F]fluoride radiolabeling and catalyst-free click chemistry to rapidly prepare 18F-labeled PET probes.", The Journal of Nuclear Medicine, vol. 56, No. 3, Suppl. 3, May 1, 2015 (May 1, 2015),-Jun. 10, 2015 (Jun. 10, 2015), p. 219, XP055297866, US ISSN: 0161-5505.
Pauline Desogere. Synthesis and studies of new optimised chelating agents for targeting chemokine receptor CXCR4. Other. Universite de Bourgogne, 2012. English. NNT: 2012DIJOS047. tel-00842206.
Wadas et al. (Current Pharm. Design 2007, 13, 3-16).
Zeglis et al. (J. Nucl. Med. 2013, 54, 1389-1396).

* cited by examiner

*Primary Examiner* — Michael G. Hartley
*Assistant Examiner* — Melissa J Perreira
(74) *Attorney, Agent, or Firm* — Foley & Lardner LLP

(57) ABSTRACT

Described herein are Tz/TCO-based pretargeting strategies using an Al[$^{18}$F]-NOTA-labeled tetrazine radioligand. This imaging strategy enables delineation of cancer at earlier time points compared to other imaging strategies and further decreases the radiation dose to healthy tissues compared to directly labeled antibodies. Al-based $^{18}$F imaging of small molecules, such as tetrazine, has not been previously achieved due to the decomposition of tetrazine during radiofluorination. Radiofluorination is advantageous over other radiolabeling methods because, in addition to having a shorter half-life, $^{18}$F is more readily available to produce and therefore integrated into hospital workflows.

6 Claims, 40 Drawing Sheets

1

[18F]2

RADIOLIGANDS FOR PRETARGETED PET IMAGING AND METHODS OF THEIR THERAPEUTIC USE

CROSS-REFERENCE TO RELATED APPLICATIONS

This application is a continuation of U.S. patent application Ser. No. 16/203,513, filed Nov. 28, 2018, now issued as U.S. Pat. No. 11,135,320, which is a continuation of U.S. patent application Ser. No. 14/826,775, filed Aug. 14, 2015, which claims priority to and the benefit of U.S. Provisional Patent Application No. 62/159,763, filed May 11, 2015, the entire contents of each of which are incorporated herein by reference.

GOVERNMENT SUPPORT

This invention was made with government support under grant numbers CA008748, CA144138, CA178205 and EB016673 awarded by the National Institutes of Health. The government has certain rights in the invention.

FIELD OF THE INVENTION

This invention relates generally to pretargeted positron emission tomography (PET) imaging of cancer. In particular embodiments, the invention relates to radioligands for pretargeted PET imaging of cancer (e.g., colorectal, pancreatic, etc.).

BACKGROUND

Over the past 25 years, antibodies have emerged as effective vectors for the sensitive and specific delivery of radioisotopes to tumors. A wide variety of radionuclides ranging from 124I for positron emission tomography (PET) to 225Ac for targeted radiotherapy have been conjugated to antibodies for preclinical investigations and clinical applications. However, the size and dosing of these radiolabeled antibodies have obstructed clinical utility. For example, intact IgG antibodies have relatively long biological half-lives due to their size, which causes them to require multiple days to weeks to reach their optimal biodistribution. Consequently, the large size of intact IgGs requires isotopes with long physical half-lives, such as $^{89}$Zr ($t_{1/2}$=3.26 d) or $^{24}$I ($t_{1/2}$=4.2 d) for PET or $^{177}$Lu ($t_{1/2}$=6.73 d) for radiotherapy. While the resulting radioimmunoconjugates can deliver high concentrations of activity to tumor tissue, the long circulation times and radioactive half-lives combine to produce significant and potentially deleterious radiation doses to healthy tissues.

To overcome these limitations, radiopharmaceuticals based on truncated immunoglobulins, such as F(ab')2, F(ab'), and scFv fragments have been developed to provide imaging agents that combine the specificity and affinity of intact IgGs with the rapid pharmacokinetics and favorable dosimetry of smaller molecules. However, preclinical studies have shown that the smaller size and more rapid pharmacokinetics result in decreased activity concentrations in the targeted tissue in addition to increased activity concentrations in excretory organs such as the kidneys.

To address these limitations, pretargeting, or strategies to decouple the antibody from the radioactivity at the time of injection, have been developed to provide an alternative approach to harness the high affinity and specificity of intact IgGs, while avoiding their pharmacokinetic drawbacks. Pretargeting uses an antibody designed to bind both a target antigen and a radiolabeled hapten. The antibody is injected into the blood and, in turn, is given time to accumulate at the tumor and concomitantly clear from the body. After the accumulation, a radiolabeled hapten is administered intravenously. The radioligand either binds to the antibody at the tumor or, due to its small size, rapidly clears from the body. If the radioligand binds to the antibody, the final radioimmunconjugate is formed at the tumor site. Thus, pretargeting achieves delineation of tumor tissue at much earlier time points than traditional radioimmunoconjugates while significantly reducing the overall radiation burden to the patient.

Until recently, three types of pretargeting technologies have been used: (1) streptavidin-fused antibodies and biotin-based radioligands, (2) oligonucleotide-labeled antibodies and radioligands bearing complementary sequences, and (3) bispecific antibodies that bind both a target antigen and a radiolabeled hapten (e.g., $^{90}$Y-DOTA). Yet despite significant preclinical successes, the widespread application of each strategy has been hampered by its intrinsic limitations. For example, the immunogenicity of the streptavidin-bearing immunoconjugates or the inherent lack of modularity of bispecific antibodies limits use in clinics.

Over the last few years, a pretargeting strategy based on the inverse electron demand Diels-Alder (IEDDA) reaction between tetrazine (Tz) and transcyclooctene (TCO) was developed and is depicted in FIG. 1. The IEDDA cycloaddition as a click chemistry conjugation reaction has been used for a variety of applications, including the fluorescent labeling of nanoparticles, antibodies, oligonucleotides, and small molecules, as well as the traditional synthesis of radiopharmaceuticals.

The IEDDA reaction was thought to be a promising tool for in vivo pretargeting. For example, the IEDDA reaction is extraordinarily rapid ($k_1$ greater than 30,000 $M^{-1}$ $s^{-1}$), selective, robust, and bioorthogonal. The use of IEDDA in pretargeting was pioneered largely by Rossin, et al., who published an $^{111}$In-based SPECT imaging approach and have improved their systems to use tetrazine-bearing clearing agents and more reactive dienophiles (Rossin, R.; van den Bosch, S. M.; Ten Hoeve, W.; Carvelli, M.; Versteegen, R. M.; Lub, J.; Robillard, M. S., Highly reactive trans-cyclooctene tags with improved stability for Diels-Alder chemistry in living systems. *Bioconj. Chem.* 2014, 34, 1210-1217).

An alternative pretargeting PET imaging strategy based on the IEDDA reaction was reported by Zeglis, B. M. et al. *Journal of Nuclear Medicine.* 54, 1389-1396 (2013) and in U.S. Provisional Application No. 62/159,763, which are hereby incorporated by reference herein in their entireties. This strategy featured a rapid and selective in vivo biorthogonal reaction between trans-cyclooctene (TCO) and tetrazine (Tz). The use of antibodies labeled with TCO and small molecule tetrazine-based radioligands allowed radioactive labeling of antibodies after accumulation at the target site in vivo. However, one of the drawbacks of this system was that the $^{64}$Cu-NOTA-labeled tetrazine radioligand cleared too slowly from the gut (e.g., small intestine, large intestine, etc.). Although the pretargeting system delineated cancer tumors with this radioligand, later imaging time points (e.g., at 12 hours (h)) were required to achieve high image contrast, and the dosimetric benefits of the system were not significant. Moreover, unclicked $^{64}$Cu-Tz-NOTA radioligand was cleared sluggishly through the intestines, hindering use as a clinical imaging system for cancer (e.g., colorectal) detection. The U.S. Provisional Application No.

62/159,763 reports a $^{64}Cu$-labeled radioligand employed for the pretargeted PET imaging of SW1222 human colorectal cancer xenografts.

As the half-life of $^{64}Cu$ is 12.74 hours the potential of utilizing even shorter-lived radionuclides to decrease the time period between the administration of the radiotracer and imaging (e.g., generate an image at an earlier time point) has significant clinical benefits: The ability to acquire clinical imaging data at earlier time points reduces radiation exposure to the patient and expedites the time that the patient is in the hospital.

As mentioned above, various pretargeting strategies based on the IEDDA reaction between Tz and TCO have been developed using $^{64}Cu$-based approaches. In addition to the aforementioned advantages of short-lived radionuclides, the availability of $^{18}F$ (or $^{68}Ga$) is considerably higher compared to $^{64}Cu$ for instance as most hospitals and imaging centers do not produce $^{64}Cu$ locally and rely on the delivery from external sources. In contrast to $^{64}Cu$, most hospitals and imaging centers have the ability to produce the $^{18}F$ radionuclide in house and hence make the use of $^{18}F$-labeled radiotracer logistically more desirable.

Although $^{18}F$-incorporation into the Tz moiety has been attempted (Li, Z, et al., Chem. Commun., 2010, 46, 8043-8045, Li, Z, et al., Chem. Commun., 2010, 46, 8043-8045, Reiner and Zeglis, J. Label Compd. Radiopharm, 2013), this has not been successful, and workarounds have been necessary, for example, attaching the $^{18}F$ radionuclide to TCO or dextran. The radiosynthesis of $^{18}F$ attached to a small molecule, such as an $^{18}F$-labeled tetrazine moiety capable of pretargeted in vivo imaging, has not been published.

Therefore, there is a need to develop low-dose radioimmunoconjugates that delineate cancer from healthy tissue in small amounts of time, possess favorable pharmacokinetic profiles, can be cleared rapidly from the body to enable high contrast PET imaging of cancer (e.g., colorectal, pancreatic), and are commercially available to or synthesized by hospitals.

SUMMARY OF INVENTION

Described herein are Tz/TCO-based pretargeting strategies using (1) a 64Cu-sarcophagine-based tetrazine radioligand for pretargeted PET imaging with more rapid excretion of the excess radioligand through the bladder and kidneys and (2) an Al[$^{18}F$]-NOTA-labeled tetrazine radioligand. These imaging strategies enable delineation of cancer at earlier time points compared to other imaging strategies and further decrease the radiation dose to healthy tissues compared to directly labeled antibodies.

The present disclosure describes the development and in vivo validation of an improved strategy for pretargeted PET imaging of colorectal and pancreatic cancer.

In certain embodiments, the present disclosure describes the synthesis and characterization of in vivo behavior of two $^{64}Cu$-labeled tetrazine radioligands: $^{64}Cu$-Tz-$PEG_7$-NOTA and $^{64}Cu$-Tz-SarAr. These two radioligands possess structural alterations that modulate their pharmacokinetic profile compared to prior imaging systems. In some example embodiments, the system described herein produces higher activity concentrations in the tumor and, due to the renal excretion of the unbound radioligand disclosed herein, provides improved tumor-to-background activity concentration ratios at early time points. Furthermore, the presently disclosed methodologies function at significantly lower dose rates required by directly labeled radioimmunoconjugates. In some certain embodiments, the present imaging strategies can be effective for any cancer (e.g., colorectal, pancreatic) for which a non-internalizing, biomarker-targeted antibody exists.

In certain embodiments, a TCO-bearing immuno-conjugate of the anti-CA19.9 antibody 5B1 and an Al[$^{18}F$]-NOTA-labeled tetrazine radioligand were harnessed for the visualization of CA19.9-expressing BxPC3 pancreatic cancer xenografts. Al-based $^{18}F$ imaging of small molecules, such as tetrazine, has not been previously achieved due to the decomposition of tetrazine during radiofluorination. Radiofluorination is advantageous over other radiolabeling methods because, in addition to having a shorter half-life, $^{18}F$ is more readily available to produce, and therefore, more suited to be integrated into hospital workflows. Biodistribution and $^{18}F$-PET imaging data clearly demonstrate that this methodology effectively delineates tumor mass with activity concentrations up to 6.4% ID/g at 4 h after injection of the radioligand.

In one aspect, the invention is directed to a composition comprising: a tetrazine moiety (Tz); a radiolabel (e.g., 18F); a chelator (e.g., 1,4,7-triazonane-1,4,7-triyl-triacetic acid (NOTA), e.g., 1,4,7-triazacyclononane-1,4-diacetate (NODA)); a linker (e.g., polyethylene glycol, (poly)-L-lysine) attaching the tetrazine moiety (Tz) to the chelator; and aluminum or aluminum-containing moiety (e.g., wherein the radiolabel is attached to aluminum).

In certain embodiments, the linker is polyethylene glycol (PEG) or (poly)-L-lysine and has a length of from 1 to 100 units and 1 to 200 units, respectively.

In certain embodiments, the composition comprises:

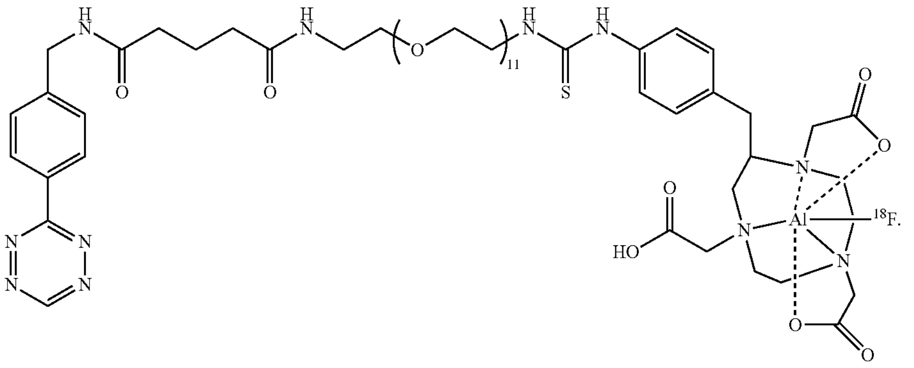

In another aspect, the invention is directed to a radioimmunoconjugate comprising: (1) a targeting moiety-transcyclooctene (TCO) conjugate (e.g., TCO-5B1); and (2) a radioligand (e.g., attached to the targeting moiety-TCO conjugate) comprising a tetrazine moiety (Tz); a radiolabel (e.g., 18F); a chelator (e.g., 1,4,7-triazonane-1,4,7-triyl-triacetic acid (NOTA), e.g., 1,4,7-triazacyclononane-1,4-diacetate (NODA)); a linker (e.g., polyethylene glycol, (poly)-L-lysine) attaching the tetrazine moiety (Tz) to the chelator; and aluminum or aluminum-containing moiety (e.g., wherein the radiolabel is attached to aluminum).

In certain embodiments, the tetrazine moiety (Tz), the chelator, and the linker attaching the tetrazine moiety to the chelator comprises a member selected from the group consisting of: 2,2',2"-(3-(4-(3-(1-(4-(1,2,4,5-tetrazin-3-yl)phenyl)-1-oxo-5,8,11,14,17,20,23-heptaoxa-2-azapentacosan-25-yl)thioureido)benzyl)-1,4,7-triazonane-2,5,8-triyl) triacetic acid; 2,2',2"-(3-(4-(3-(1-(4-(1,2,4,5-tetrazin-3-yl) phenyl)-1-oxo-5,8,11,14,17,20,23,26,29,32,35-undecaoxa-2-azaheptatriacontan-37-yl)thioureido)benzyl)-1,4,7-triazonane-2,5,8-triyl)triacetic acid; 2,2'-(7-(4-(3-(1-(4-(1,2,4,5-tetrazin-3-yl)phenyl)-1-oxo-5,8,11,14,17,20,23,26,29,32,35-undecaoxa-2-azaheptatriacontan-37-yl)thioureido) benzyl)-1,4,7-triazonane-1,4-diyl)diacetic acid; 2,2',2"-(3-(4-(3-(1-(4-(1,2,4,5-tetrazin-3-yl)phenyl)-3,7-dioxo-11,14,17,20,23,26,29-heptaoxa-2,8-diazahentriacontan-31-yl) thioureido)benzyl)-1,4,7-triazonane-2,5,8-triyl)triacetic acid; 2,2',2"-(3-(4-(3-(1-(4-(1,2,4,5-tetrazin-3-yl)phenyl)-3,7-dioxo-11,14,17,20,23,26,29,32,35,38,41-undecaoxa-2,8-diazatritetracontan-43-yl)thioureido)benzyl)-1,4,7-triazonane-2,5,8-triyl)triacetic acid; 2,2',2"-(3-(4-(3-(25,28-dioxo-28-((6-(6-(pyridin-2-yl)-1,2,4,5-tetrazin-3-yl) pyridin-3-yl)amino)-3,6,9,12,15,18,21-heptaoxa-24-azaoctacosyl)thioureido)benzyl)-1,4,7-triazonane-2,5,8-triyl)triacetic acid; 2,2',2"-(3-(4-(3-(37,40-dioxo-40-((6-(6-(pyridin-2-yl)-1,2,4,5-tetrazin-3-yl)pyridin-3-yl)amino)-3,6,9,12,15,18,21,24,27,30,33-undecaoxa-36-azatetracontyl) thioureido)benzyl)-1,4,7-triazonane-2,5,8-triyl)triacetic acid; 2,2',2"-(3-(4-(1-(4-(6-methyl-1,2,4,5-tetrazin-3-yl) phenyl)-3-oxo-6,9,12,15,18,21,24-heptaoxa-2-azaheptacosan-27-amido)benzyl)-1,4,7-triazonane-2,5,8-triyl)triacetic acid; 2,2',2"-(2-(4-(1-(4-(6-methyl-1,2,4,5-tetrazin-3-yl)phenoxy)-3,6,9,12,15,18,21,24,27,30,33-undecaoxahexatriacontan-36-amido)benzyl)-1,4,7-triazonane-1,4,7-triyl)triacetic acid; 2,2',2"-(3-(4-(3-(5-amino-6-((4-(6-methyl-1,2,4,5-tetrazin-3-yl)benzyl)amino)-6-oxohexyl)thioureido)benzyl)-1,4,7-triazonane-2,5,8-triyl) triacetic acid; 2,2'-(7-(4-(3-(5-amino-6-((4-6-methyl-1,2,4,5-tetrazin-3-yl)benzyl)amino)-6-oxohexyl)thioureido) benzyl)-1,4,7-triazonane-1,4-diyl)diacetic acid; 2,2',2"-(3-(4-(3-(5-amino-6-((5-amino-6-((4-(6-methyl-1,2,4,5-tetrazin-3-yl)benzyl)amino)-6-oxohexyl)amino)-6-oxohexyl)thioureido)benzyl)-1,4,7-triazonane-2,5,8-triyl) triacetic acid; and 2,2',2"-(3-(4-(3-(5-amino-6-((5-amino-6-((5-amino-6-((4-(6-methyl-1,2,4,5-tetrazin-3-yl)benzyl) amino)-6-oxohexyl)amino)-6-oxohexyl)amino)-6-oxohexyl)thioureido)benzyl)-1,4,7-triazonane-2,5,8-triyl) triacetic acid.

In certain embodiments, the composition is hydrophilic (e.g., having a partition coefficient less than 2).

In certain embodiments, the radioligand comprises:

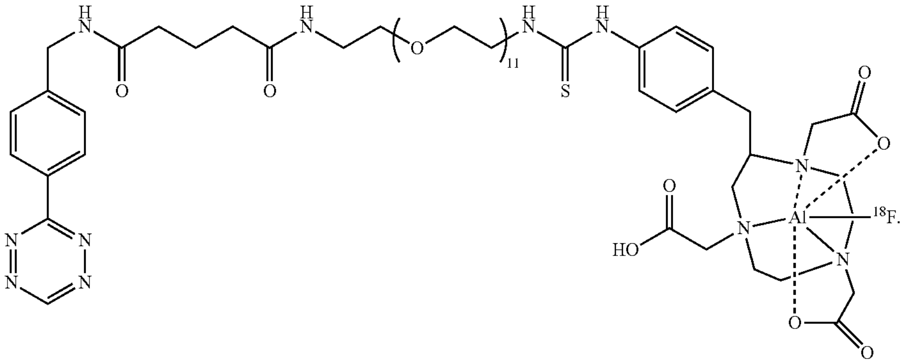

In certain embodiments, the targeting moiety-TCO conjugate has a TCO moiety comprises:

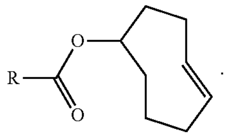

R = N, C

In certain embodiments, wherein linker is polyethylene glycol (PEG) or (poly)-L-lysine and has a length of from 1 to 100 units and 1 to 200 units, respectively.

In another aspect, the invention is directed to a method for synthesizing a radioligand: (1) preparing Tz-PEG11-NOTA (tetrazine-polyethylene glycol-1,4,7-triazonane-1,4,7-triyl-triacetic acid) (e.g., comprising coupling Tz-NHS (tetrazine-N-hydroxysuccinimide) to NH2-PEG11-NHBoc; deprotecting the terminal tert-butyloxycarbonyl protecting group to obtain Tz-PEG11-NH2; and reacting Tz-PEG11-NH2 with p-SCN-Bn-NOTA to yield Tz-PEG11-NOTA (e.g., wherein Tz-PEG11-NOTA is prepared with a purity of greater than 98% and with an overall yield of greater than 10%)); (2) preparing a Al-$^{18}$F complex (e.g., comprising eluting [18F] fluoride into a metal-free solvent; mixing the eluted [18F] fluoride with a AlCl3-solution (e.g., wherein mixing is performed at room temperature and a pH of 3.5-4); incubating the mixture (e.g., wherein the mixture is incubated at 30° C.); and (3) reacting the Tz-PEG11-NOTA (e.g., wherein the solvent of the prepared Tz-PEG11-NOTA is acetonitrile (MeCN)/water in a volumetric ratio of 3:1) and the Al-$^{18}$F complex to yield the radioligand Tz-PEG11-Al [$^{18}$F]-NOTA, wherein the radioligand is obtained in 54% to 65% radiochemical yield (decay-corrected to the start of synthesis) with a purity greater than 96% and specific activities between 20 to 30 Gbq/μmol.

In another aspect, the invention is directed to a method for detecting tumor cells, the method comprising: (1) administering (e.g., injecting) a quantity of targeting moiety-trans-cyclooctene (TCO) conjugate (e.g., TCO-5B1) to a subject, wherein a portion of the targeting moiety-TCO conjugate localizes at the tumor cells and unbound targeting moiety-TCO conjugate is cleared (e.g., from the blood, from the renal system, and/or from the subject) after an accumulation interval (e.g., wherein the accumulation interval is less than 240 hours, e.g., less than 216 hours, e.g., less than 192 hours, e.g., less than 144 hours, e.g., less than 120 hours, e.g., less than 96 hours, e.g., less than 72 hours, e.g., less than 48 hours, e.g., less than 24 hours); (2) administering (e.g., injecting) a radioligand to the subject after the accumulation interval, wherein the radioligand comprises a tetrazine moiety (Tz); a radiolabel (e.g., 18F); a chelator (e.g., 1,4,7-triazonane-1,4,7-triyl-triacetic acid (NOTA), e.g., 1,4,7-triazacyclononane-1,4-diacetate (NODA)); a linker (e.g., polyethylene glycol, (poly)-L-lysine) attaching the tetrazine moiety (Tz) to the chelator; and aluminum or aluminum-containing moiety (e.g., wherein the radiolabel is attached to aluminum), wherein the targeting moiety-TCO conjugate and the radioligand bind together to form a radioimmunoconjugate via an in vivo click reaction at the tumor site within a region of the subject; and (3) imaging (e.g., via positron emission tomography (PET) imaging) the radioimmunoconjugate accumulated in the region of the subject within a time period less than 9 hours (e.g., less than 6 hours, less than 4 hours, less than 2 hours) from the administering of the radioligand.

In certain embodiments, the radioligand comprises:

In certain embodiments, the radioimmunoconjugate has an activity concentration in a large intestine of the subject that is less than 2% of the initial dose per gram (ID/g) (e.g., less than 1% ID/g, e.g., less than 0.5% ID/g, e.g., less than 0.1% % ID/g) after 2 hour post injection.

In certain embodiments, the radioimmunoconjugate has an activity concentration in a gastrointestinal tract of the subject that is less than 2% of the initial dose per gram (ID/g) (e.g., less than 1% ID/g, less than 0.5% ID/g, e.g., less than 0.1% % ID/g) after 2 hour post injection.

In certain embodiments, the radioimmunoconjugate has an activity concentration in a hepatobiliary system of the subject that is less than 2% of the initial dose per gram (ID/g) (e.g., less than 1% ID/g, less than 0.5% ID/g, e.g., less than 0.1% % ID/g) after 2 hour post injection.

In certain embodiments, the linker is polyethylene glycol (PEG) or (poly)-L-lysine and has a length of from 1 to 100 units and 1 to 200 units, respectively.

In certain embodiments, the radioligand is hydrophilic (e.g., wherein the hydrophilicity of the composition is determined by a partition coefficient (e.g., wherein the partition coefficient is less than 2)).

In certain embodiments, the targeting moiety is an antibody. In certain embodiments, the antibody is a member selected from the group consisting of trastuzumab, J591, bevacizumab, B43.13, AR9.6, 3F8, 8H9, huA33, and 51. In certain embodiments, the targeting moiety is a nanoparticle, a peptide, or other biomolecule.

In certain embodiments, the tumor cells are colorectal tumor cells or pancreatic tumor cells (e.g., wherein the tumor cells can be detected using a non-internalizing, biomarker-targeted antibody) (e.g., wherein the tumor cells comprise a biomarker on the surface of the cell).

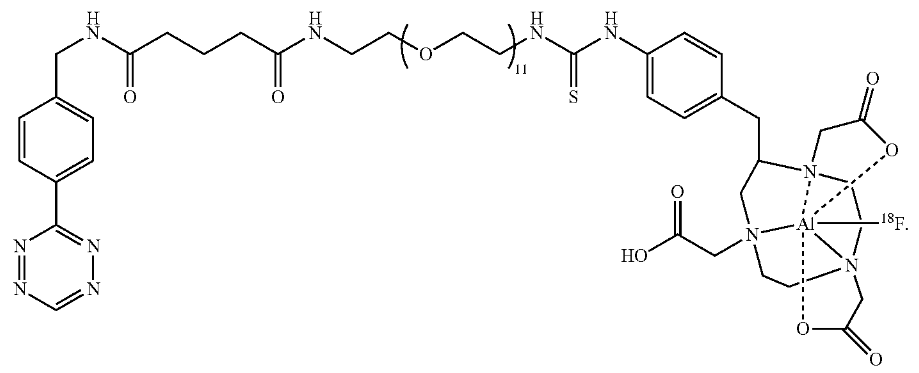

In certain embodiments, the targeting moiety-TCO conjugate has a TCO moiety comprising:

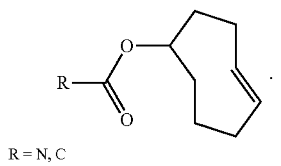

In certain embodiments, the radioligand has an effective dose of less than 0.1 rem/mCi (e.g., less than 0.05 rem/mCi) over a 4 hour accumulation interval.

In certain embodiments, the radioligand has a half-life in blood that is less than 100 minutes.

In certain embodiments, the tetrazine moiety (Tz), the chelator, and the linker attaching the tetrazine moiety to the chelator comprises a member selected from the group consisting of: 2,2',2"-(3-(4-(3-(1-(4-(1,2,4,5-tetrazin-3-yl)phenyl)-1-oxo-5,8,11,14,17,20,23-heptaoxa-2-azapentacosan-25-yl)thioureido)benzyl)-1,4,7-triazonane-2,5,8-triyl) triacetic acid; 2,2',2"-(3-(4-(3-(1-(4-(1,2,4,5-tetrazin-3-yl) phenyl)-1-oxo-5,8,11,14,17,20,23,26,29,32,35-undecaoxa-2-azaheptatriacontan-37-yl)thioureido)benzyl)-1,4,7-triazonane-2,5,8-triyl)triacetic acid; 2,2'-(7-(4-(3-(1-(4-(1,2,4,5-tetrazin-3-yl)phenyl)-1-oxo-5,8,11,14,17,20,23,26,29,32,35-undecaoxa-2-azaheptatriacontan-37-yl)thioureido) benzyl)-1,4,7-triazonane-1,4-diyl)diacetic acid; 2,2',2"-(3-(4-(3-(1-(4-(1,2,4,5-tetrazin-3-yl)phenyl)-3,7-dioxo-11,14,17,20,23,26,29-heptaoxa-2,8-diazahentriacontan-31-yl) thioureido)benzyl)-1,4,7-triazonane-2,5,8-triyl)triacetic acid; 2,2',2"-(3-(4-(3-(1-(4-(1,2,4,5-tetrazin-3-yl)phenyl)-3,7-dioxo-11,14,17,20,23,26,29,32,35,38,41-undecaoxa-2,8-diazatritetracontan-43-yl)thioureido)benzyl)-1,4,7-triazonane-2,5,8-triyl)triacetic acid; 2,2',2"-(3-(4-(3-(25,28-dioxo-28-((6-(6-(pyridin-2-yl)-1,2,4,5-tetrazin-3-yl)pyridin-3-yl)amino)-3,6,9,12,15,18,21-heptaoxa-24-azaoctacosyl)thioureido)benzyl)-1,4,7-triazonane-2,5,8-triyl)triacetic acid; 2,2',2"-(3-(4-(3-(37,40-dioxo-40-((6-(6-(pyridin-2-yl)-1,2,4,5-tetrazin-3-yl)pyridin-3-yl)amino)-3,6,9,12,15,18,21,24,27,30,33-undecaoxa-36-azatetracontyl)thioureido)benzyl)-1,4,7-triazonane-2,5,8-triyl)triacetic acid; 2,2',2"-(3-(4-(1-(4-(6-methyl-1,2,4,5-tetrazin-3-yl)phenyl)-3-oxo-6,9,12,15,18,21,24-heptaoxa-2-azaheptacosan-27-amido)benzyl)-1,4,7-triazonane-2,5,8-triyl)triacetic acid; 2,2',2"-(2-(4-(1-(4-(6-methyl-1,2,4,5-tetrazin-3-yl)phenoxy)-3,6,9,12,15,18,21,24,27,30,33-undecaoxahexatriacontan-36-amido)benzyl)-1,4,7-triazonane-1,4,7-triyl)triacetic acid; 2,2',2"-(3-(4-(3-(5-amino-6-((4-(6-methyl-1,2,4,5-tetrazin-3-yl)benzyl)amino)-6-oxohexyl)thioureido)benzyl)-1,4,7-triazonane-2,5,8-triyl)triacetic acid; 2,2'-(7-(4-(3-(5-amino-6-((4-6-methyl-1,2,4,5-tetrazin-3-yl)benzyl)amino)-6-oxohexyl)thioureido)benzyl)-1,4,7-triazonane-1,4-diyl)diacetic acid; 2,2',2"-(3-(4-(3-(5-amino-6-((5-amino-6-((4-(6-methyl-1,2,4,5-tetrazin-3-yl)benzyl)amino)-6-oxohexyl)amino)-6-oxohexyl)thioureido)benzyl)-1,4,7-triazonane-2,5,8-triyl)triacetic acid; and 2,2',2"-(3-(4-(3-(5-amino-6-((5-amino-6-((5-amino-6-((4-(6-methyl-1,2,4,5-tetrazin-3-yl)benzyl)amino)-6-oxohexyl)amino)-6-oxohexyl)amino)-6-oxohexyl)thioureido)benzyl)-1,4,7-triazonane-2,5,8-triyl)triacetic acid.

In another aspect, the invention is directed to a kit for targeted positron emission tomography (PET) comprising: a plurality of containers, wherein each container has a type selected from an ampule, a vial, a cartridge, a reservoir, a lyo-ject, or a pre-filled syringe; the composition; and a targeting moiety-transcyclooctene (TCO) conjugate (e.g., TCO-5B1), wherein a first container of the plurality of containers holds (e.g., contains) the composition (e.g., a first solution comprising the composition); and a second container of the plurality of containers holds (e.g., contains) the targeting moiety-TCO conjugate (e.g., a second solution comprising the conjugate).

Elements of embodiments involving one aspect of the invention (e.g., methods) can be applied in embodiments involving other aspects of the invention (e.g., systems), and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4% 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Biomolecule": As used herein, "biomolecule" refers to bioactive, diagnostic, and prophylactic molecules. Biomolecules that can be used in the present invention include, but are not limited to, synthetic, recombinant or isolated peptides and proteins such as antibodies and antigens, receptor ligands, enzymes, and adhesion peptides; nucleotides and polynucleic acids such as DNA and antisense nucleic acid molecule; activated sugars and polysaccharides; bacteria; viruses; and chemical drugs such as antibiotics, antiinflammatories, and antifungal agents.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Radiolabel": As used herein, "radiolabel" refers to a moiety comprising a radioactive isotope of at least one element. Exemplary suitable radiolabels include but are not limited to those described herein. In some embodiments, a radiolabel is one used in positron emission tomography (PET). In some embodiments, a radiolabel is one used in single-photon emission computed tomography (SPECT). In some embodiments, radioisotopes comprise $^{99m}$Tc, $^{111}$In, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{13}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Small molecule": As used herein, the term "small molecule" can refer to a non-polymeric molecule, for example, or a species less than 5000 Da.

"Therapeutic agent": As used herein, the phrase "therapeutic agent" refers to any agent that has a therapeutic effect and/or elicits a desired biological and/or pharmacological effect, when administered to a subject.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIG. 25A shows hematoxylin and eosin staining.

FIG. 25B shows immunofluorescence staining for the huA33 antibody.

FIG. 25C shows autoradiography indicating the localization of $^{64}$Cu-Tz-SarAr.

FIG. 25D shows an overlay of immunofluorescence staining and autoradiography;

FIG. 25E higher magnification image of the area enclosed by the black box in FIG. 25A.

FIGS. 25F-25H show higher magnification images of the same area corresponding to FIGS. 25B-25D, respectively.

DETAILED DESCRIPTION

Figure 1:
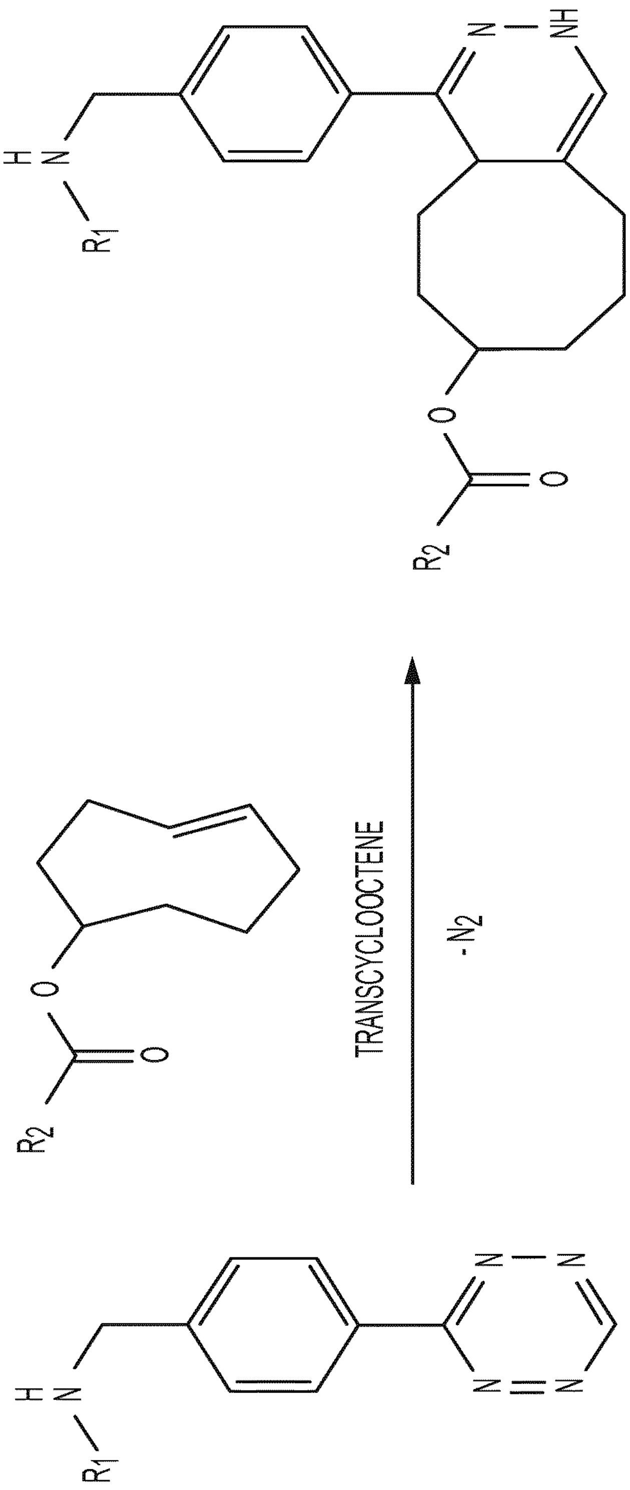
FIG. 1 shows the inverse electron demand Diels-Alder cycloaddition.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Described herein are Tz/TCO-based pretargeting strategies using (1) a 64Cu-sarcophagine-based tetrazine radioligand for pretargeted PET imaging with more rapid excretion of the excess radioligand through the bladder and kidneys and (2) an Al[$^{18}$F]-NOTA-labeled tetrazine radioligand. These imaging strategies enable delineation of cancer at earlier time points compared to other imaging strategies and further decrease the radiation dose to healthy tissues compared to directly labeled antibodies.

In certain embodiments, two radioligands $^{64}$Cu-Tz-PEG$_7$-NOTA and $^{64}$Cu-Tz-SarAr based on $^{64}$Cu-Tz-NOTA were designed to harbor structural modifications to alter the pharmacokinetics of $^{64}$Cu-Tz-NOTA. The in vivo evaluation of these two constructs revealed that $^{64}$Cu-Tz-PEG$_7$-NOTA was eliminated via both the gastrointestinal and renal tracts and $^{64}$Cu-Tz-SarAr was cleared through the renal system alone. Moreover, pretargeted PET imaging and biodistribution experiments using huA33-TCO, $^{64}$Cu-Tz-SarAr, and mice bearing human colorectal carcinoma xenografts revealed that this approach delineated malignant tissue with high tumor-to-background contrast at only a fraction of the radiation dose created by traditional, directly-labeled radioimmunoconjugates. Altering the molecular structure of the tetrazine-bearing radioligand effectively eliminated background uptake of the radioligand in the gastrointestinal tract.

In certain embodiments, a TCO-bearing immuno-conjugate of the anti-CA19.9 antibody 5B1 and an Al[$^{18}$F]-NOTA-labeled tetrazine radioligand were harnessed for the visualization of CA19.9-expressing BxPC3 pancreatic cancer xenografts. Al-based $^{18}$F imaging of small molecules, such as tetrazine, has not been previously achieved due to the decomposition of tetrazine during radiofluorination. Radiofluorination is advantageous over other radiolabeling methods because, in addition to having a shorter half-life, $^{18}$F is more readily available to produce and therefore more convenient to integrate into hospital workflows. Biodistribution and $^{18}$F-PET imaging data demonstrate that this methodology effectively delineates tumor mass with activity concentrations up to 6.4% ID/g at 4 h after injection of the radioligand.

$^{64}$Cu-based Tetrazine Radioligands for Pretargeted Imaging

The present disclosure describes the synthesis and characterization of the in vivo behavior of two $^{64}$Cu-labeled tetrazine radioligands—$^{64}$Cu-Tz-PEG$_7$-NOTA and $^{64}$Cu-Tz-SarAr—that possess structural alterations to modulate their pharmacokinetic profiles. It was found that the $^{64}$Cu- Tz-SarAr radioligand, in combination with the huA33-TCO, performed better than the $^{64}$Cu-Tz-NOTA radioligand. For example, the combined huA33-TCO and $^{64}$Cu-Tz-SarAr system exhibited higher activity concentrations in the tumor, the $^{64}$Cu-Tz-SarAr radioligand was rapidly cleared through the renal system allowing for higher tumor-to-background activity concentration ratios at early time points, and the presently described system demonstrated dosimetric improvement over other radioimmunoconjugate systems.

System Design

At a basic level, the pretargeting strategy described herein comprises three components: (1) the antibody, (2) the transcyclooctene, and (3) the tetrazine; each component is important. The present disclosure describes a pretargeted PET imaging system for colorectal system, which uses the huA33 antibody. The huA33 antibody is a humanized antibody that targets the A33 antigen, a transmembrane glycoprotein abundantly expressed by greater than 95% of all colorectal cancer tumors. While low levels of expression of the A33 antigen have been found on normal bowel epithelium, clinical studies with $^{124}$I-labeled huA33 have illustrated that tumor tissue retains the antibody far longer than healthy epithelium. Furthermore, in vitro studies have shown that the huA33-A33 antigen complex persists on the surface of the cell for days after formation. These features are important for pretargeting methodologies because the antibody must accumulate in tumor tissue compared to normal tissue and remain accessible to the radioligand for the in vivo ligation to occur.

Figure 2:
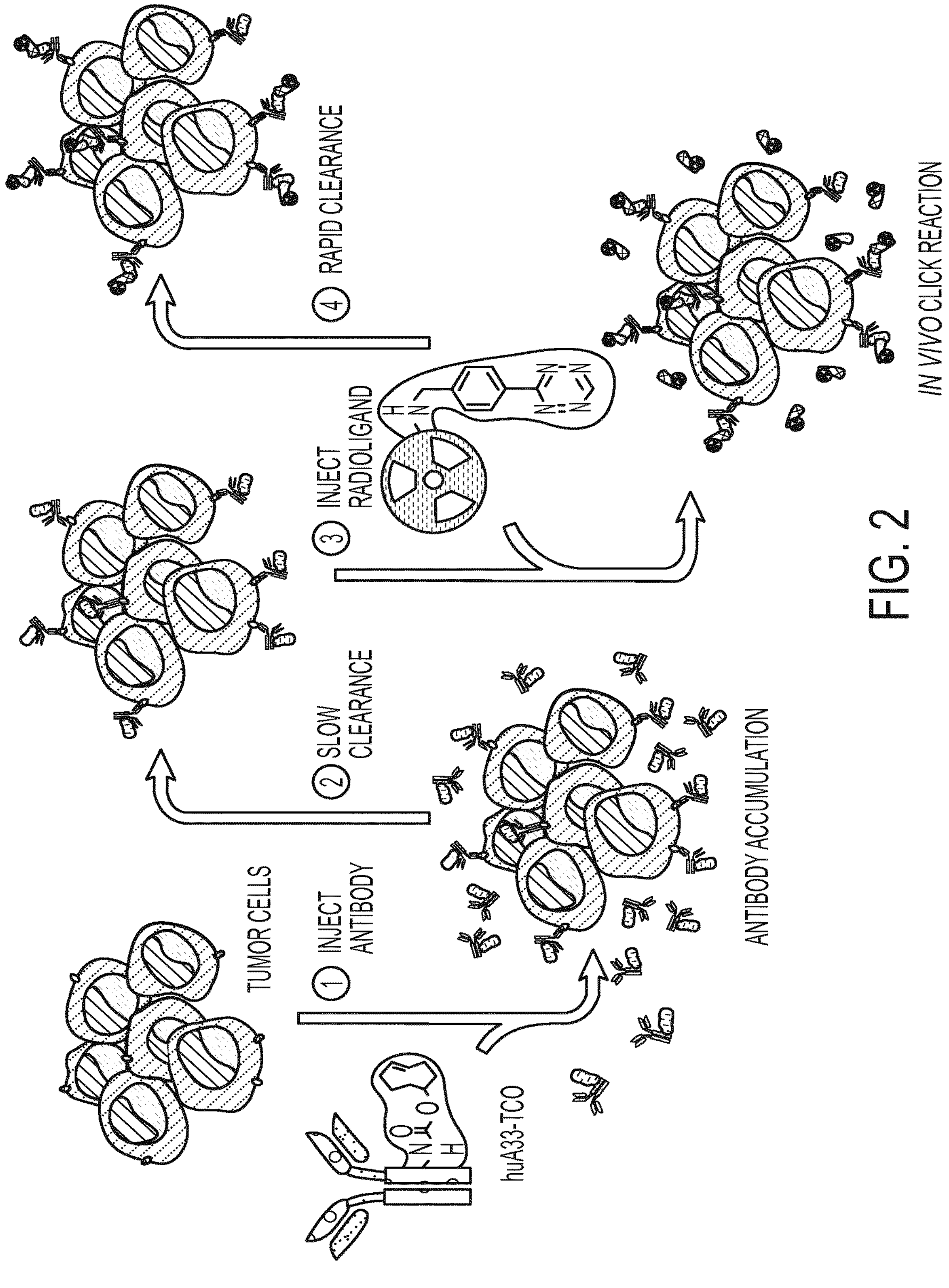
FIG. 2 shows a schematic of the pretargeted PET imaging strategy.

The pretargeted PET system includes: (1) injection of the huA33-TCO conjugate; (2) accumulation of the antibody at the target site and allowing unbound antibody to clear from the blood; (3) injection of the radioligand; and (4) an in vivo click ligation of the two components, followed by clearance of the excess radioligand (FIG. 2). Importantly, this pretargeting strategy effectively delineates tumor tissue at much earlier time points than directly radiolabeled antibodies and significantly reduces the overall radiation burden to the patient, permitting safer and more accurate diagnoses in shorter time frames.

The present disclosure also describes use of transcyclooct-4-en-1-yl hydrogen carbonate (TCO) and 3-4-(benzylamine)-1,2,4,5-tetrazine (Tz) as the transcyclooctene and tetrazine components. The IEDDA cycloaddition between these two moieties has been shown to be extraordinarily rapid, with a second order rate constant greater than 30,000 $M^{-1}$ $s^{-1}$. Furthermore, both components have been shown to be sufficiently stable in physiological settings, and amine-reactive variants (TCO-NHS and Tz-NHS) of both are commercially available.

Figure 3A:
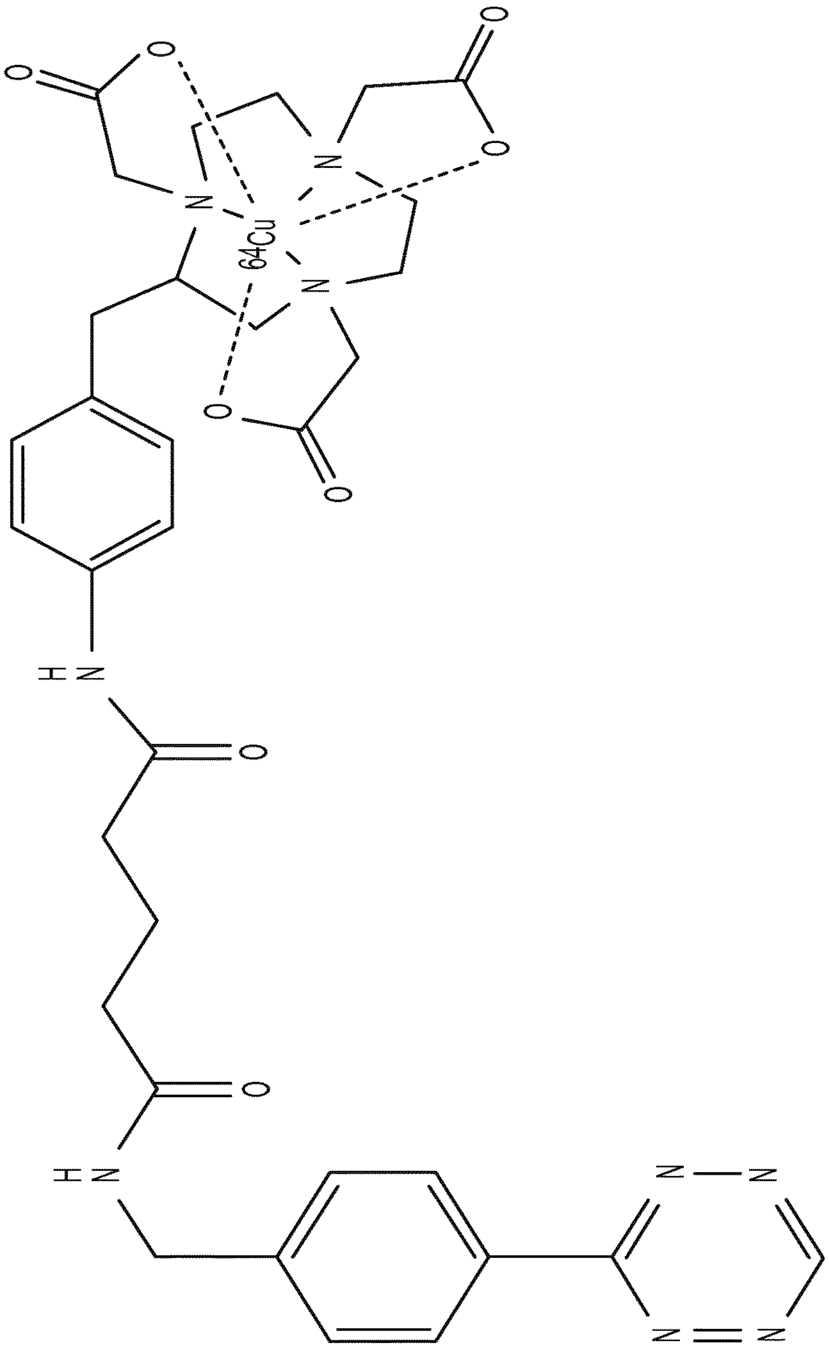
FIG. 3A shows a structure of $^{64}$Cu-Tz-NOTA.

As described above, the relatively slow ($t_{1/2}$~4 h) clearance of the $^{64}$Cu-Tz-NOTA (FIG. 3A) through the intestinal tract has hampered potential use as a methodology for imaging colorectal cancer. Without being bound by theory, it is thought that PEG linkers also known as oligoethyleneglycol linkers—can accelerate the clearance and lower the non-target tissue uptake of radiopharmaceuticals. Likewise, without being bound by theory, it is thought that changes to the identity of the chelator and the overall charge of the radiometal-chelator complex can dramatically influence pharmacokinetics. Thus, two $^{64}$Cu-Tz radioligands with structural alterations made to $^{64}$Cu-Tz-NOTA were designed for improved pharmacokinetic profiles. To this end, two different structural motifs (e.g., polyethyleneglycol (PEG) linkers and chelators) were used to influence the in vivo behavior of radiotracers.

Figure 3B:
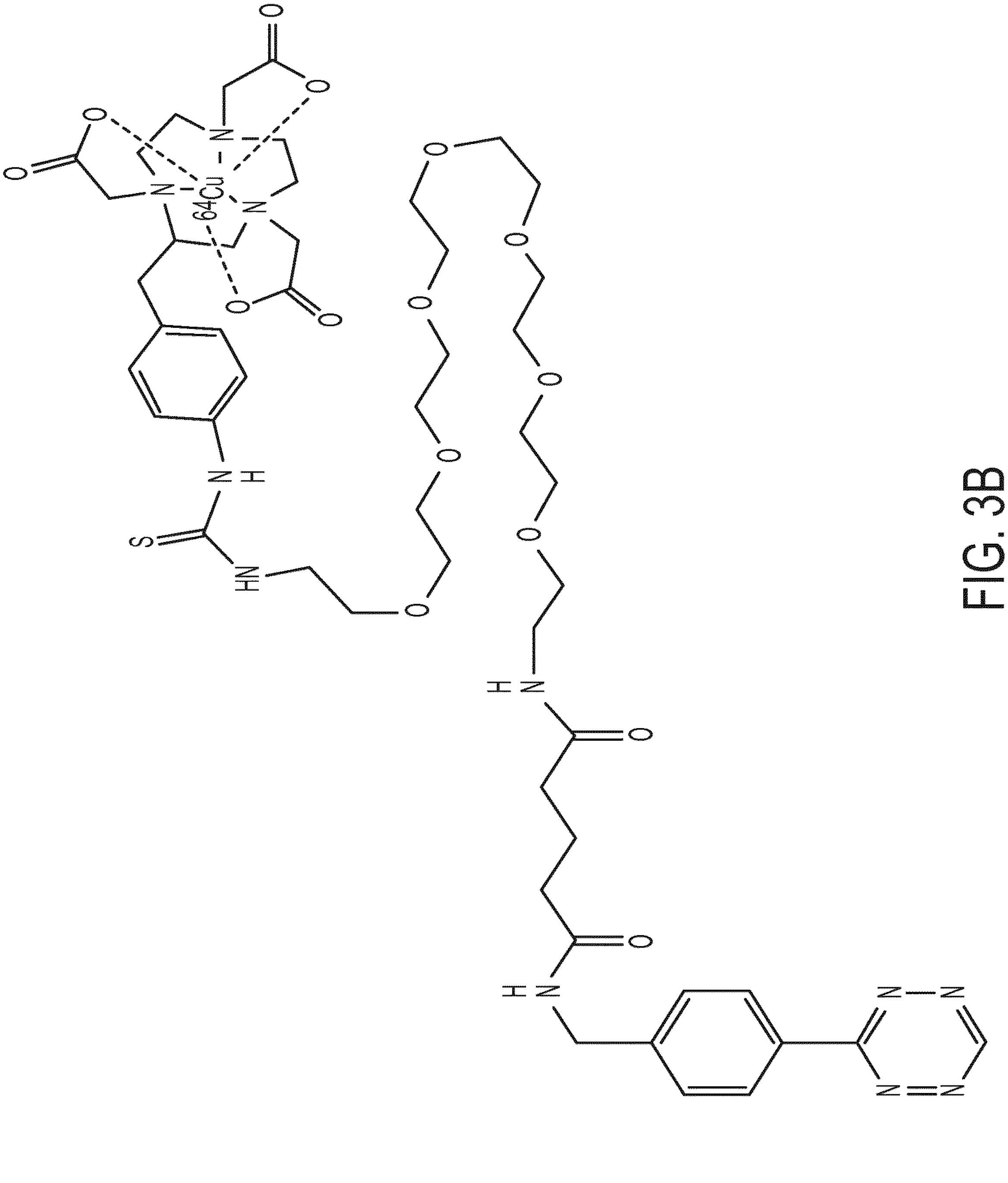
FIG. 3B shows a structure of $^{64}$Cu-Tz-PEG$_7$-NOTA.
Figure 3C:
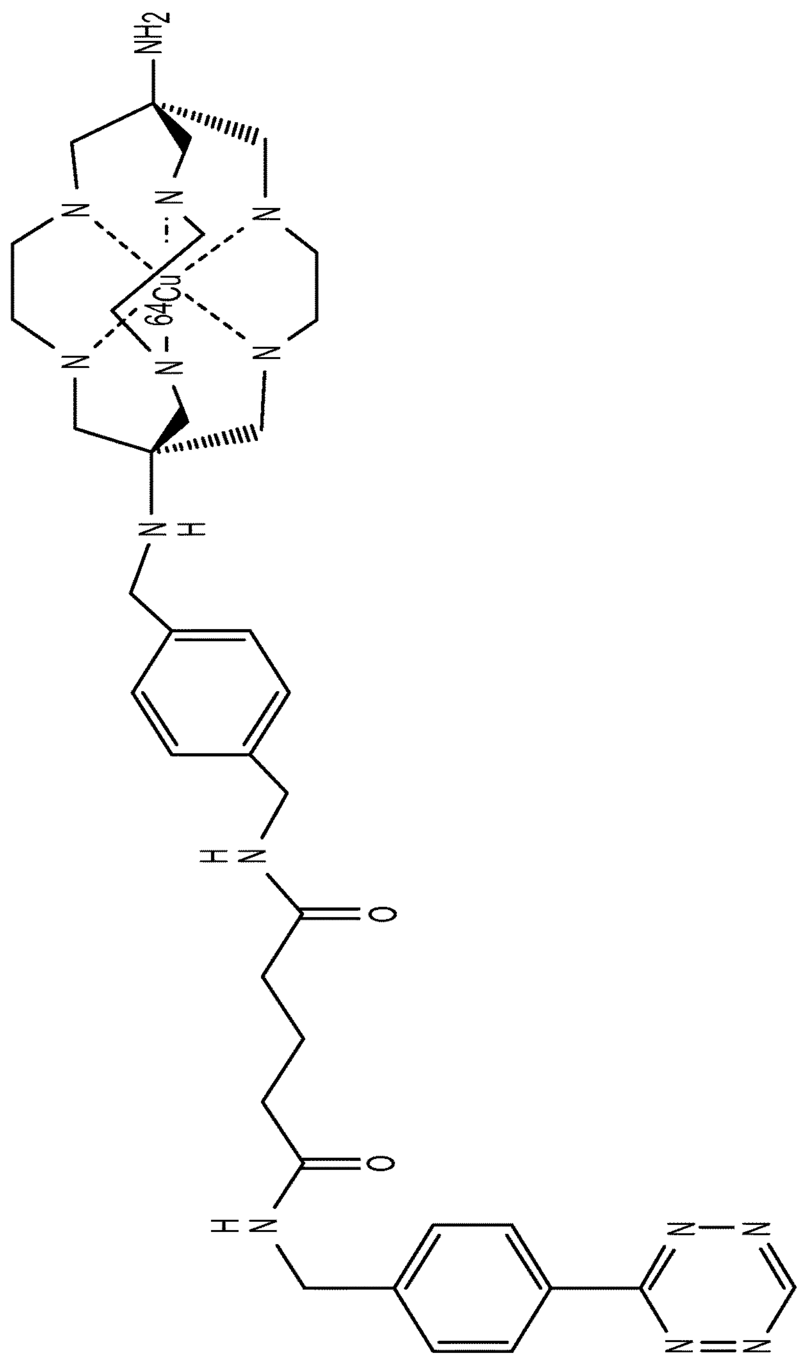
FIG. 3C shows a structure of $^{64}$Cu-Tz-SarAr.

In a first example disclosed herein, $^{64}$Cu-Tz-PEG$_7$-NOTA contained a PEG$_7$ spacer that separated the tetrazine moiety from the NOTA chelator (FIG. 3B). In a second example disclosed herein, $^{64}$Cu-Tz-SarAr contained a sarcophagine-based chelator (SarAr) that replaced the NOTA macrocycle. This chelator substitution not only changed the coordination environment from $N_3O_3$ to $N_6$ but shifted the overall charge of the metal-ligand complex from −1 ($Cu^{II}$-NOTA) to +2 ($Cu^{II}$-SarAr) (FIG. 3C). Table 0 depicts some selected properties of the three tetrazine radioligands shown in FIGS. 3A-3C.

TABLE 0

| Radioligand | Molecular weight (MW) | Coordination Environment | Net Charge | Log D | % Intact After 2 h @ 37° C. (PBS) | % Intact After 2 h @ 37° C. (Serum) |
|---|---|---|---|---|---|---|
| $^{64}$CU-Tz-NOTA | 752.6 | $N_3O_3$ | −1 | −2.54 +/− 0.10 | 91.6 +/− 1.9 | 85.4 +/− 6.6 |
| $^{64}$CU-Tz-PEG$_7$-NOTA | 1163.2 | $N_3O_3$ | −1 | −2.44 +/− 0.08 | 87.0 +/− 1.3 | 84.7 +/− 4.8 |
| $^{64}$CU-Tz-SarAr | 780.9 | $N_6$ | +2 | −2.08 +/− 0.06 | 94.7 +/− 0.6 | 92.0 +/− 2.1 |

Synthesis and Characterization

Figure 4:
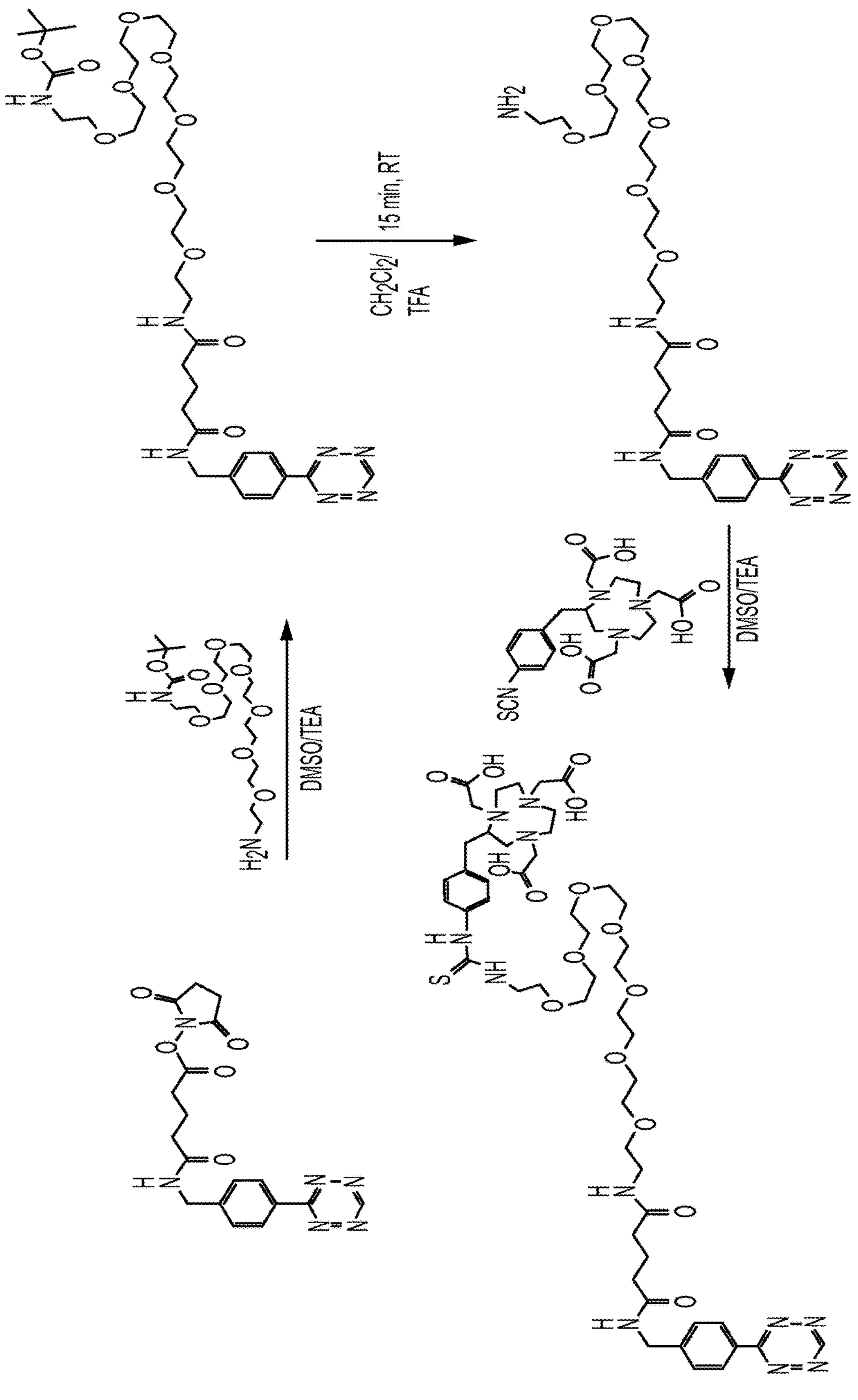
FIG. 4 shows a schematic of the synthesis of Tz-PEG$_7$-NOTA.
Figure 5:
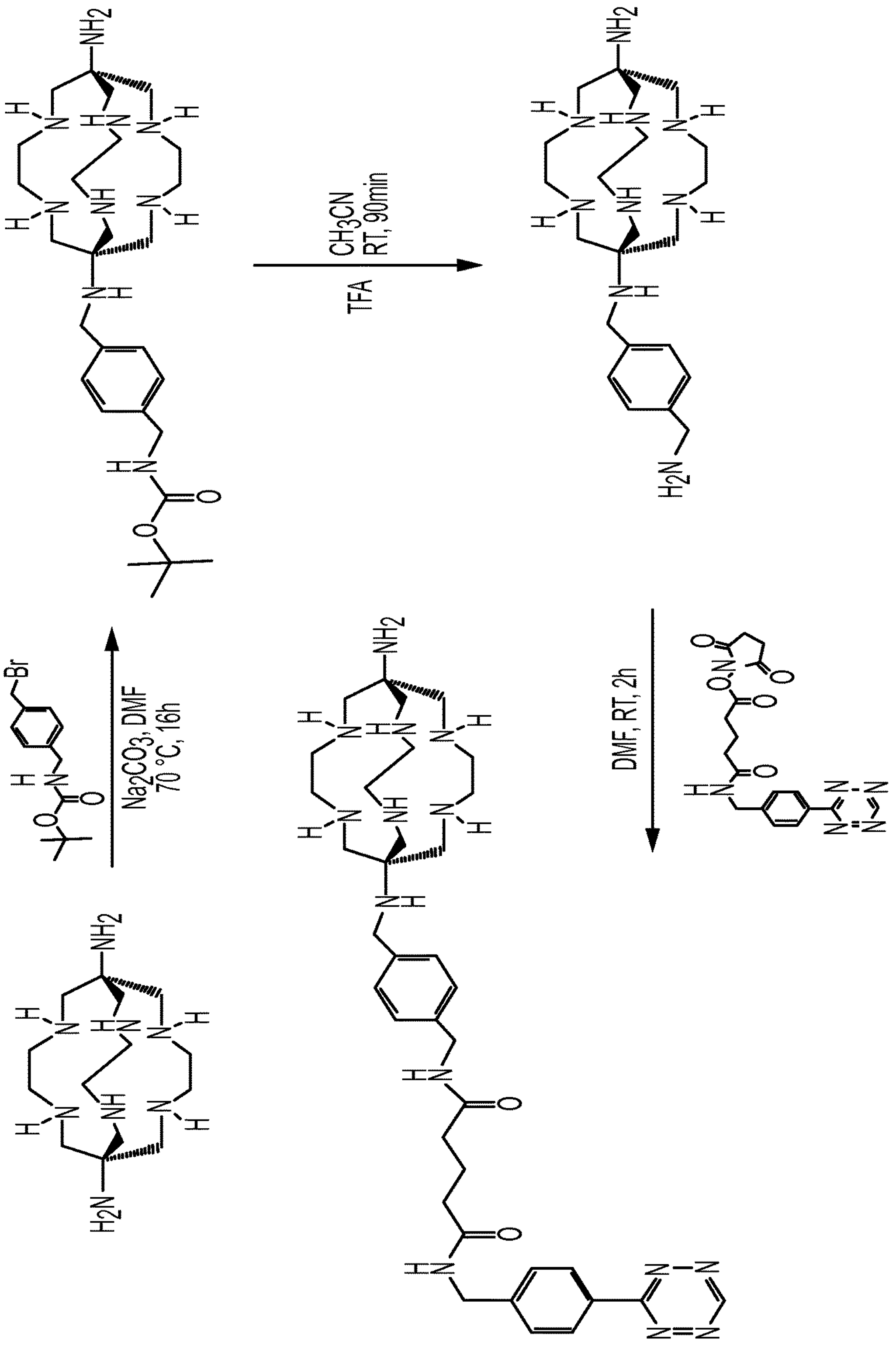
FIG. 5 shows a schematic of the synthesis of Tz-SarAr.
Figure 6:
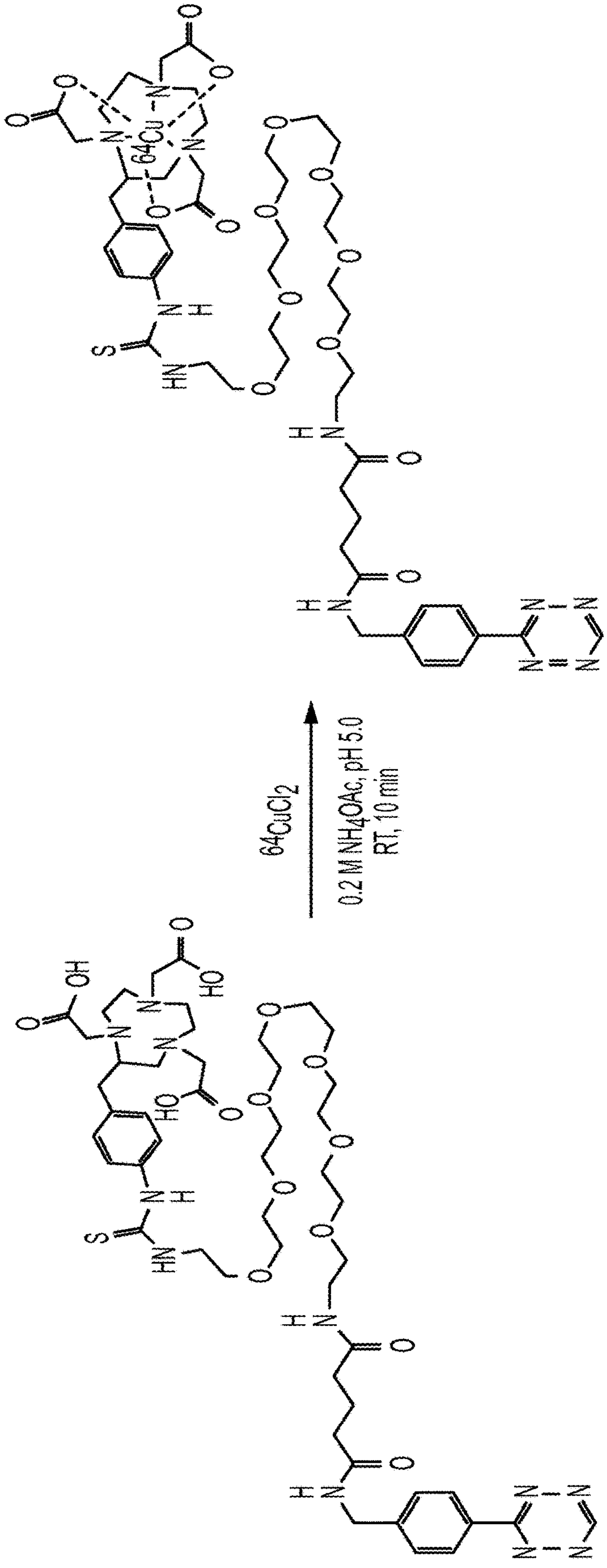
FIG. 6 shows a schematic of the radiosynthesis of $^{64}$Cu-Tz-PEG$_7$-NOTA.
Figure 7:
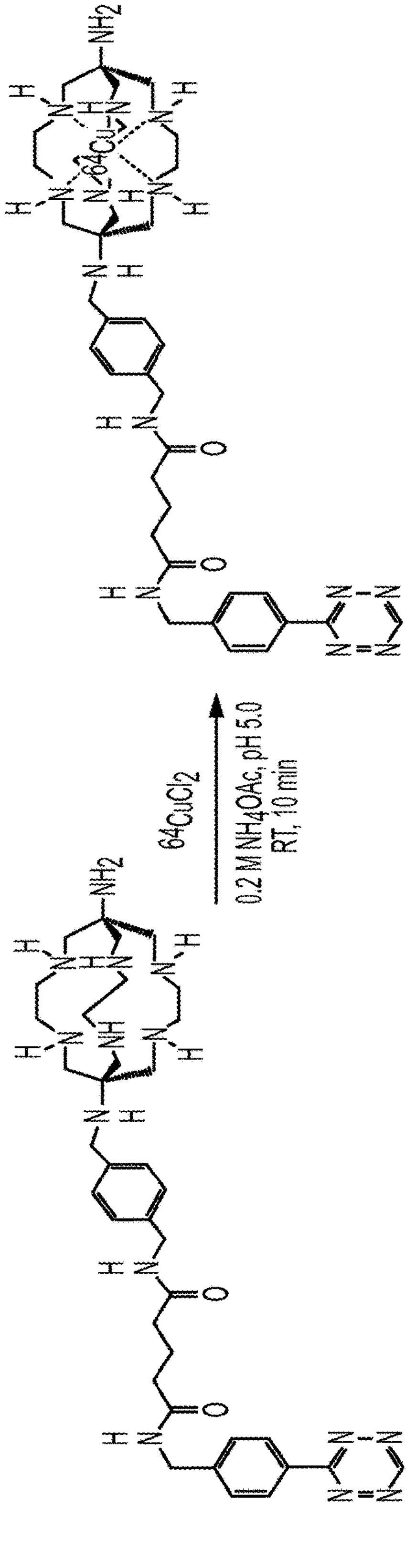
FIG. 7 shows a schematic of the radiosynthesis of $^{64}$Cu-Tz-SarAr.
Figure 8:
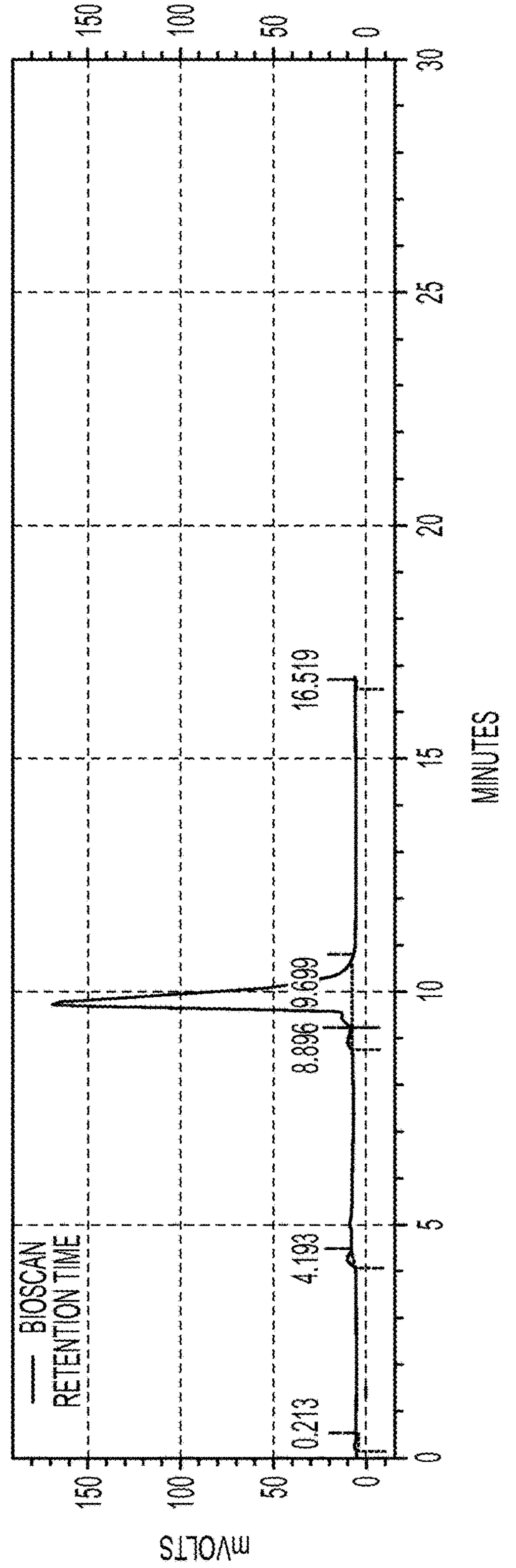
FIG. 8 shows a crude radio-HPLC chromatogram of $^{64}$Cu-Tz-PEG$_7$-NOTA.
Figure 9:
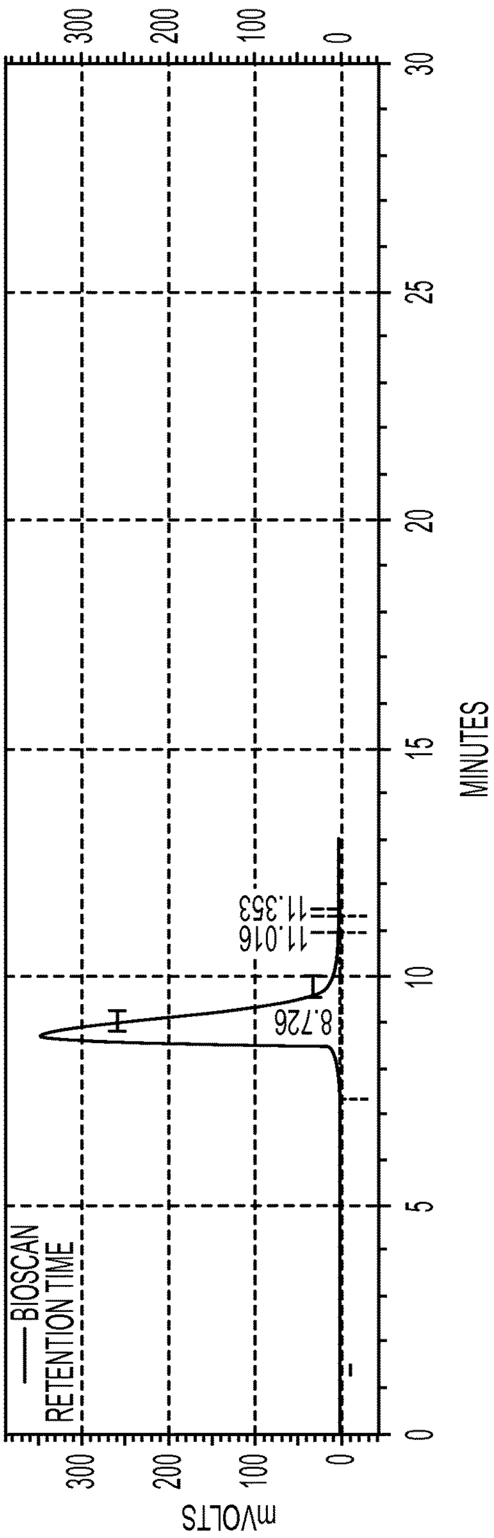
FIG. 9 shows a crude radio-HPLC chromatogram of $^{64}$Cu-Tz-SarAr.

Tz-PEG$_7$-NOTA was synthesized in 49% yield over three facile steps: the coupling of Tz-NHS and monofunctional 0-(2-aminoethyl)-O'-[2-(bocamino)ethyl]hexaethylene glycol to form Tz-PEG$_7$-NHBoc; the removal of the tert-butyloxycarbonyl protecting group with TFA/$CH_2Cl_2$; and the coupling of Tz-PEG$_7$-NH$_2$ with p-NCS-Bn-NOTA (FIG. 4). Given the symmetry of its sarcophagine precursor, Tz-SarAr required more complex synthesis. In this case, the mono-alkylation of DiAmSar with Boc-protected 4-(bromomethyl)-benzylamine was followed by the removal of the acid-labile protecting group with TFA and the coupling of the resulting SarAr-Bn-NH$_2$ moiety with Tz-NHS to produce the final product in 29% yield over three steps (FIG. 5). For both syntheses, all intermediates as well as the completed tetrazine-bearing precursors were analyzed and purified using reverse-phase $C_{18}$ HPLC and characterized via UV-Vis spectrophotometry, $^{1}$H-NMR, ESI-MS, and high-resolution mass spectrometry.

Once the precursors were made, the tetrazine constructs were then radiolabeled via incubation with [$^{64}$Cu]—$CuCl_2$ for 10 minutes at room temperature in 200 mM $NH_4OAc$, pH 5.0 and purified via reverse-phase $C_{18}$ HPLC ($t_R$=8.7 min for $^{64}$Cu-Tz-SarAr and 9.7 min for $^{64}$Cu-Tz-PEG$_7$NOTA; FIGS. 6-9). In both cases, the identity of the radiolabeled product was confirmed via co-injection of unlabeled $^{nat}$Cu-Tz-SarAr and $^{nat}$Cu-Tz-PEG$_7$-NOTA standards. Ultimately, $^{64}$Cu-Tz-PEG$_7$NOTA was prepared in greater than 99% radionuclidic purity, 78±6% decay-corrected isolated yield, and a specific activity of 323±37 mCi/μmol (n=6). Similarly, $^{64}$Cu-Tz-SarAr was synthesized in greater than 99% radionuclidic purity, 79±7% decay-corrected isolated yield, and a specific activity of 310±36 mCi/μmol (n=6). The $^{64}$Cu-Tz-NOTA radioligand was synthesized, radiolabeled, and purified as previously reported by Zeflis et al. *J. Nucl. Med.* 2013, 54, 1389-1396, which is hereby incorporated by reference in its entirety. In order to probe the influence of the structural changes on solubility, the partition coefficients of the various radioligands were determined using PBS (pH 7.4) and 1-octanol (Table 1). Table 1 shows partition coefficient (Log D) of the $^{64}$Cu-labeled tetrazines in 1-octanol and PBS (pH 7.4). While all three radioligands proved reasonably hydrophilic (e.g., log D values below −2), differences were observed. For example, the replacement of NOTA with SarAr rendered $^{64}$Cu-Tz-SarAr (log D=−2.08±0.06) more hydrophobic than $^{64}$Cu-Tz-NOTA (log D=−2.54±0.1). Moreover, the addition of the $PEG_7$ moiety in $^{64}$Cu-Tz-$PEG_7$-NOTA did not generate a more hydrophilic product (log D=−2.44±0.08) than the $^{64}$Cu-Tz-NOTA radioligand that lacked a linker.

TABLE 1

| Radioligand | LogD |
|---|---|
| $^{64}$Cu-Tz-NOTA | −2.54 ± 0.10 |
| $^{64}$Cu-Tz-$PEG_7$-NOTA | −2.44 ± 0.08 |
| $^{64}$Cu-Tz-SarAr | −2.08 ± 0.06 |

Next, the aqueous and serum stabilities were determined via incubation at 37° C. (Tables 2-3). Both $^{64}$Cu-Tz-$PEG_7$-NOTA and $^{64}$Cu-Tz-SarAr were shown to be fairly stable in PBS (pH 7.4). It was determined that 94.7±0.6% and 93.3±0.5% of $^{64}$Cu-Tz-SarAr remained intact after 2 and 4 h, respectively. $^{64}$Cu-Tz-$PEG_7$-NOTA proved similarly stable, with 87.0±1.3% (2 h) and 83.2±4.6% (4 h) intact. However, more extensive decomposition was observed in human serum. For example, after a 4 h incubation, 77.8±3.5% and 81.2±3.7% of $^{64}$Cu-Tz-$PEG_7$-NOTA and $^{64}$Cu-Tz-SarAr, respectively, remained intact. Importantly, the release of $^{64}Cu^{2+}$ from the chelators was not observed in any of the trials. Despite the rates of decomposition, the speed of the IEDDA reaction was faster than short blood half-lives of these small molecules; therefore, the radioligands remained functional in vivo. Table 2 shows the percent of $^{64}$Cu-Tz-$PEG_7$-NOTA and $^{64}$Cu-Tz-SarAr intact after incubation in PBS (pH 7.4) at 37° C. Table 3 shows the percent of $^{64}$Cu-Tz-$PEG_7$-NOTA and $^{64}$Cu-Tz-SarAr intact after incubation in human serum at 37° C.

TABLE 2

| Time | $^{64}$Cu-Tz-$PEG_7$-NOTA | $^{64}$Cu-Tz-SarAr |
|---|---|---|
| 2 h | 87.0 ± 1.3 | 94.7 ± 0.6 |
| 4 h | 83.2 ± 4.6 | 93.3 ± 0.5 |
| 8 h | 76.2 ± 2.6 | 89.7 ± 2.3 |

TABLE 3

| Time | $^{64}$Cu-Tz-$PEG_7$-NOTA | $^{64}$Cu-Tz-SarAr |
|---|---|---|
| 2 h | 84.7 ± 4.8 | 92.0 ± 2.1 |
| 4 h | 77.8 ± 3.5 | 81.2 ± 3.7 |
| 8 h | 64.0 ± 6.5 | 67.7 ± 4.3 |

Figure 10:
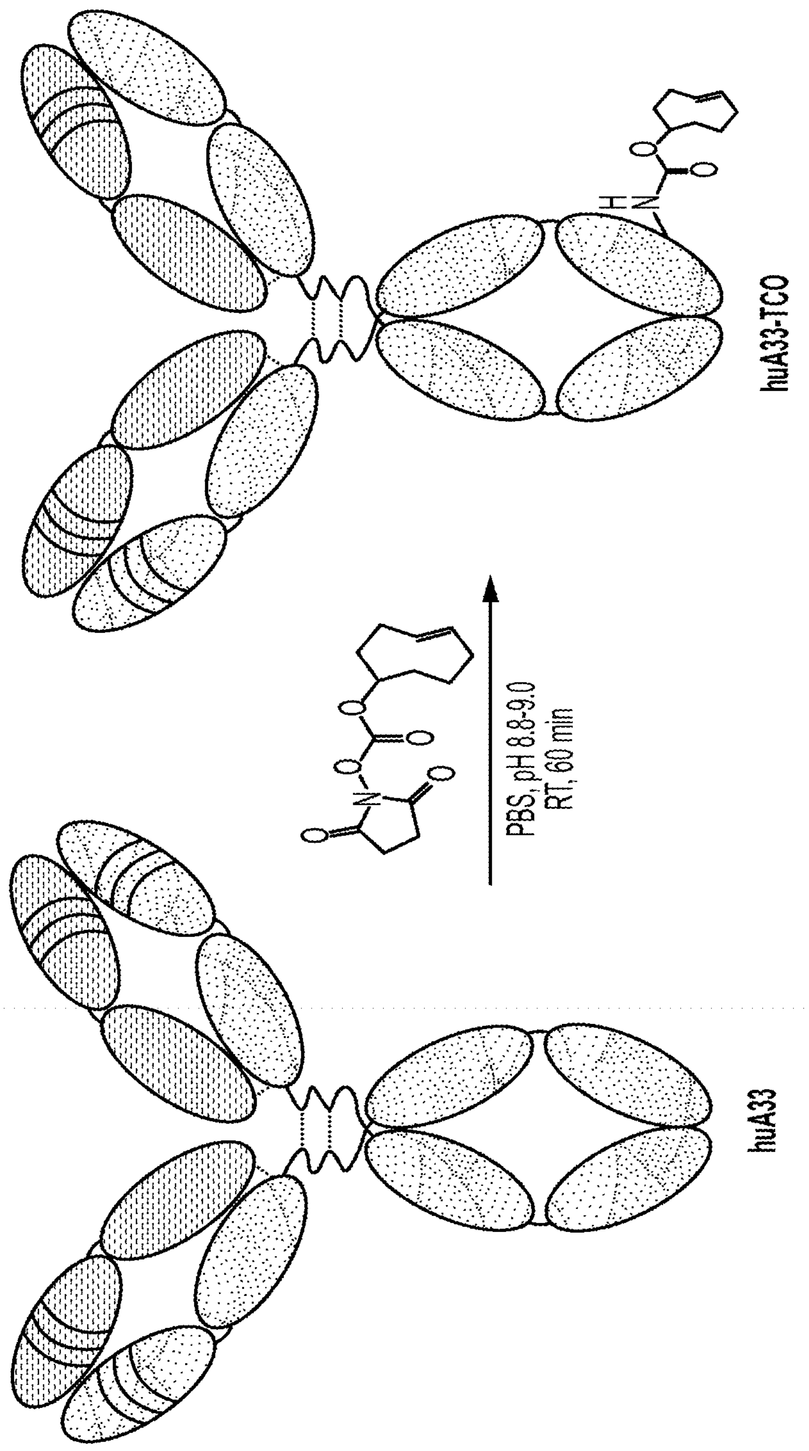
FIG. 10 shows a schematic of the synthesis of huA33-TCO
Figure 11:
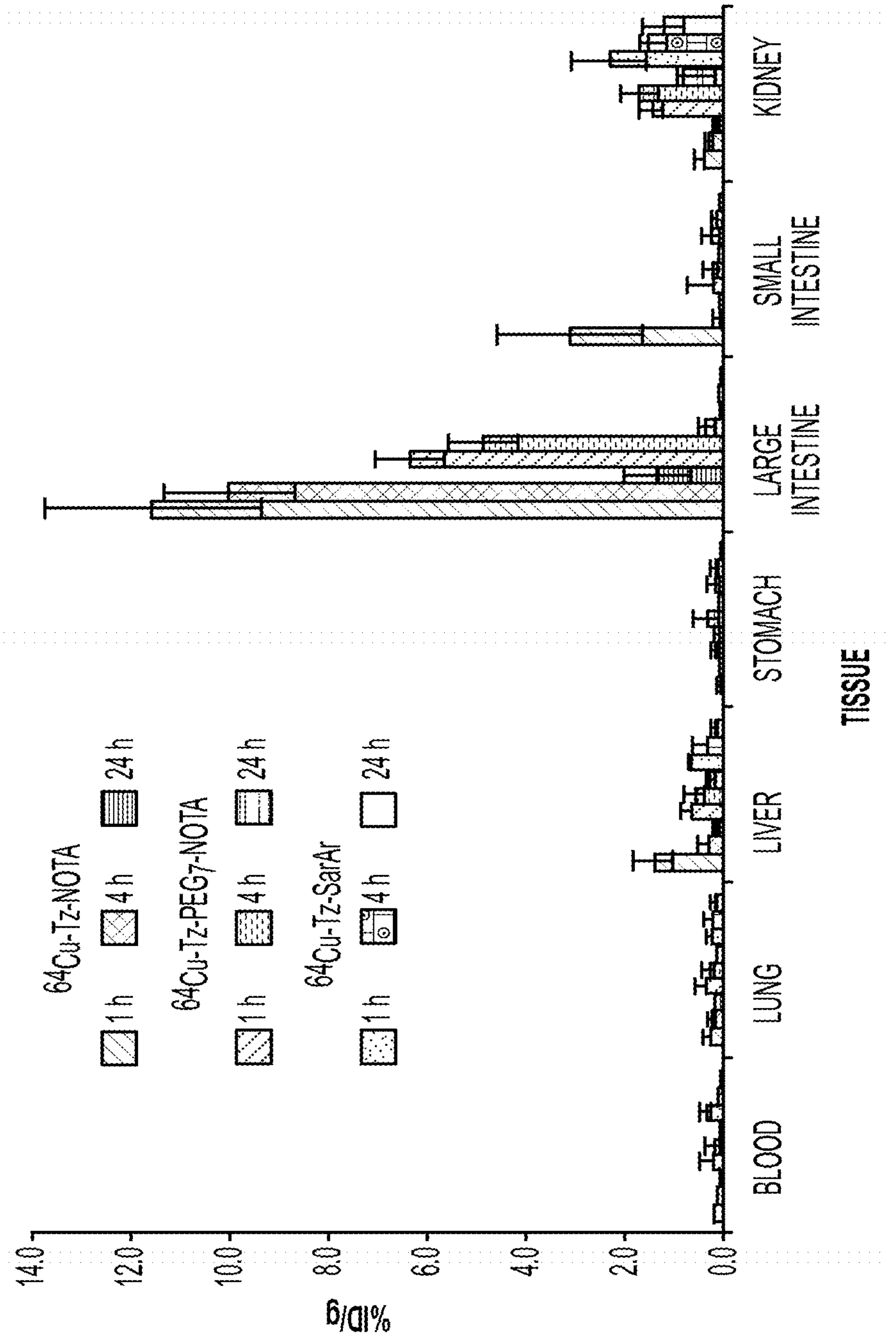
FIG. 11 shows biodistribution data (% ID/g±SD) of $^{64}$Cu-Tz-NOTA, $^{64}$Cu-Tz-PEG$_7$-NOTA, and $^{64}$Cu-Tz-SarAr in healthy athymic nude (n=4 for each time point). Mice were administered the radioligands (25-30 μCi in 200 mL 0.9% sterile saline) via intravenous tail vein injection and euthanized by $CO_2$(g) asphyxiation at 1, 4, and 24 h after injection.

Next, huA33-TCO was synthesized via the coupling of TCO-NHS to the huA33 antibody as previously described (FIG. 10). Briefly, a solution of huA33 (2-3 mg/mL) in PBS was adjusted to pH 8.8-9.0 with 0.1 M $Na_2CO_3$. Ten molar equivalents of TCO-NHS were then added to the antibody solution, and the resulting reaction mixture was incubated at room temperature for 1 hr prior to purification via size exclusion chromatography. Using a fluorophore-labeled tetrazine probe (Tz-$PEG_7$-AF680), the TCO occupancy of the huA33 was determined to be 3.6±0.6 TCO/mAb. Both $^{64}$Cu-Tz-$PEG_7$-NOTA and $^{64}$Cu-Tz-SarAr were incubated with huA33-TCO and rapidly resulted in greater than 95% reaction yields. After purification, $^{64}$Cu-labeled huA33 radioimmunoconjugates exhibited high specific activities (greater than 2 mCi/mg) and immunoreactive fractions (greater than 0.95) with A33 antigen-expressing SW1222 human colorectal carcinoma cells (Table 4). Control reactions between unmodified huA33 and the $^{64}$Cu-labeled tetrazines as well as huA33-TCO and uncomplexed $^{64}Cu^{2+}$ resulted in less than 1% radiolabeling of the huA33 constructs. Table 4 shows immunoreactive fractions of radioimmunoconjugates formed through the reaction of huA33-TCO and either $^{64}$Cu-Tz-$PEG_7$-NOTA or $^{64}$Cu-Tz-SarAr, as determined via in vitro assays with A33 antigen-expressing SW1222 cells.

TABLE 4

| Radioimmunoconjugate | Immunoreactive Fraction |
|---|---|
| huA33-TCO + $^{64}$Cu-Tz-$PEG_7$-NOTA | 0.96 ± 0.02 |
| huA33-TCO + $^{64}$Cu-Tz-SarAr | 0.97 ± 0.01 |

In Vivo Evaluation of the $^{64}$Cu-Labeled Tetrazines

Figure 12:
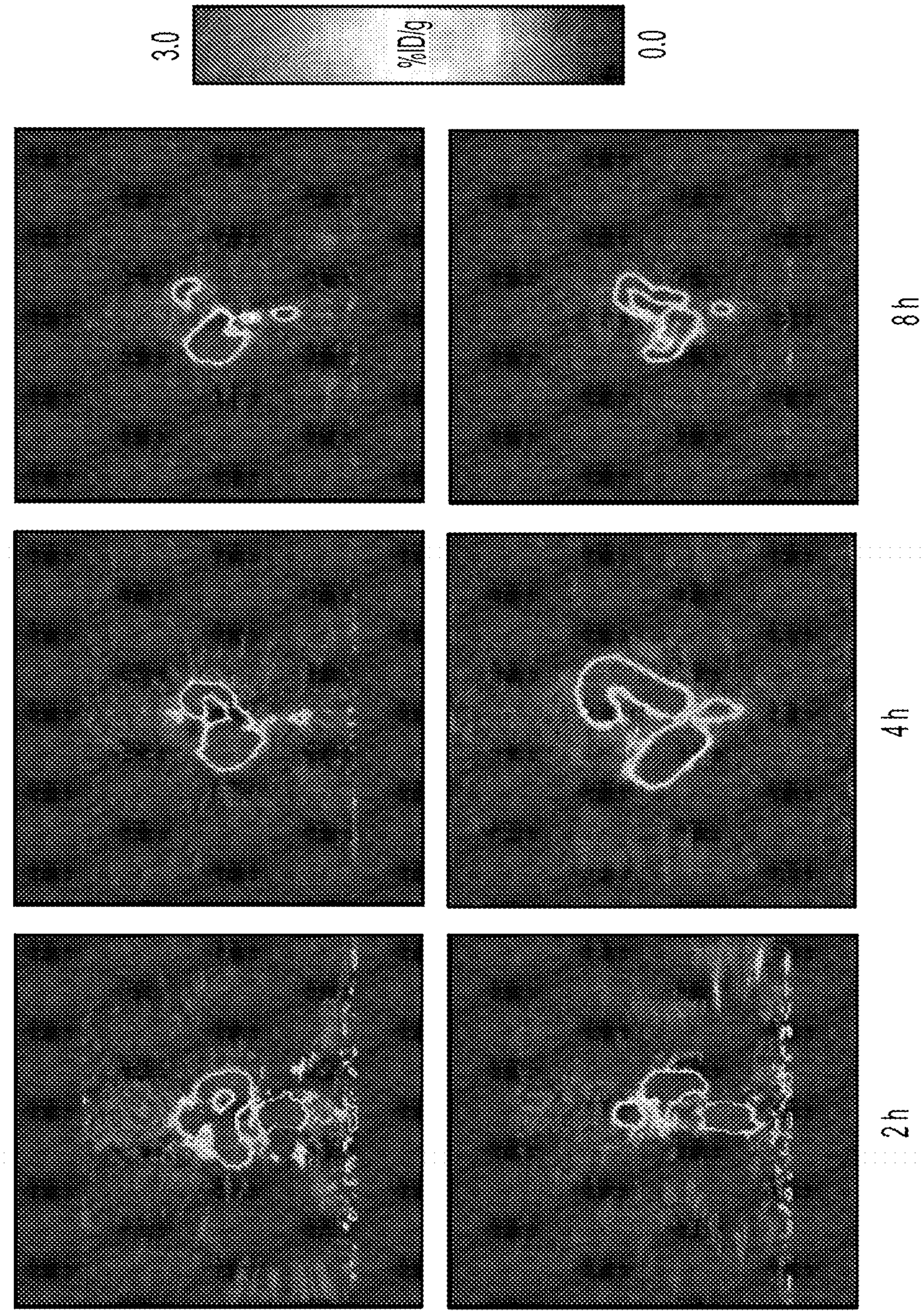
FIG. 12 shows PET imaging data for $^{64}$Cu-Tz-NOTA in two healthy mice. Healthy female athymic nude mice were administered $^{64}$Cu-Tz-NOTA (300-350 μCi in 200 mL 0.9% sterile saline) via intravenous tail vein injection (t=0). Approximately 5 minutes prior to the PET images, mice were anesthetized by inhalation of 2% isoflurane (Baxter Healthcare, Deerfield, IL)/oxygen gas mixture and placed on the scanner bed; anesthesia was maintained using 1% isoflurane/gas mixture. Static scans were recorded at various time points after injection with a minimum of 30 million coincident events (10-30 min total scan time). Activity concentrations (percentage of dose per gram of tissue [% ID/g]) and maximum intensity projections were determined by conversion of the counting rates from the reconstructed images. All of the resulting PET images were analyzed using ASIPro VM™ software. The coronal slices above are representative images chosen to illustrate the areas of highest uptake.
Figure 13:
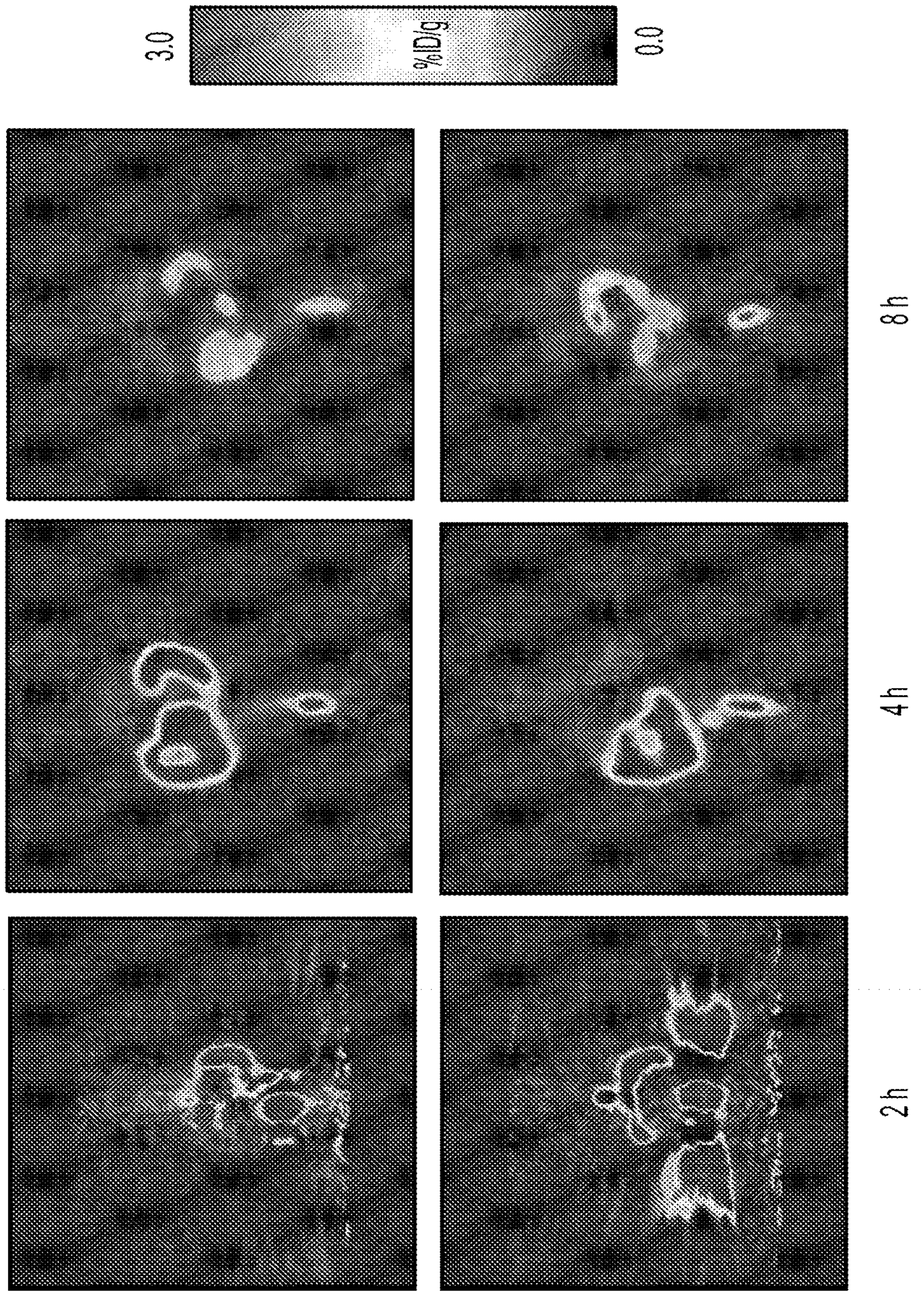
FIG. 13 shows PET imaging data for $^{64}$Cu-Tz-PEG7-NOTA in two healthy mice. Healthy female athymic nude mice were administered $^{64}$Cu-Tz-PEG$_7$-NOTA (300-350 μCi in 200 mL 0.9% sterile saline) via intravenous tail vein injection (t=0). Approximately 5 minutes prior to the PET images, mice were anesthetized by inhalation of 2% isoflurane (Baxter Healthcare, Deerfield, IL)/oxygen gas mixture and placed on the scanner bed; anesthesia was maintained using 1% isoflurane/gas mixture. Static scans were recorded at various time points after injection with a minimum of 30 million coincident events (10-30 min total scan time). Activity concentrations (percentage of dose per gram of tissue [% ID/g]) and maximum intensity projections were determined by conversion of the counting rates from the reconstructed images. All of the resulting PET images were analyzed using ASIPro VM™ software. The coronal slices above are representative images chosen to illustrate the areas of highest uptake.
Figure 14:
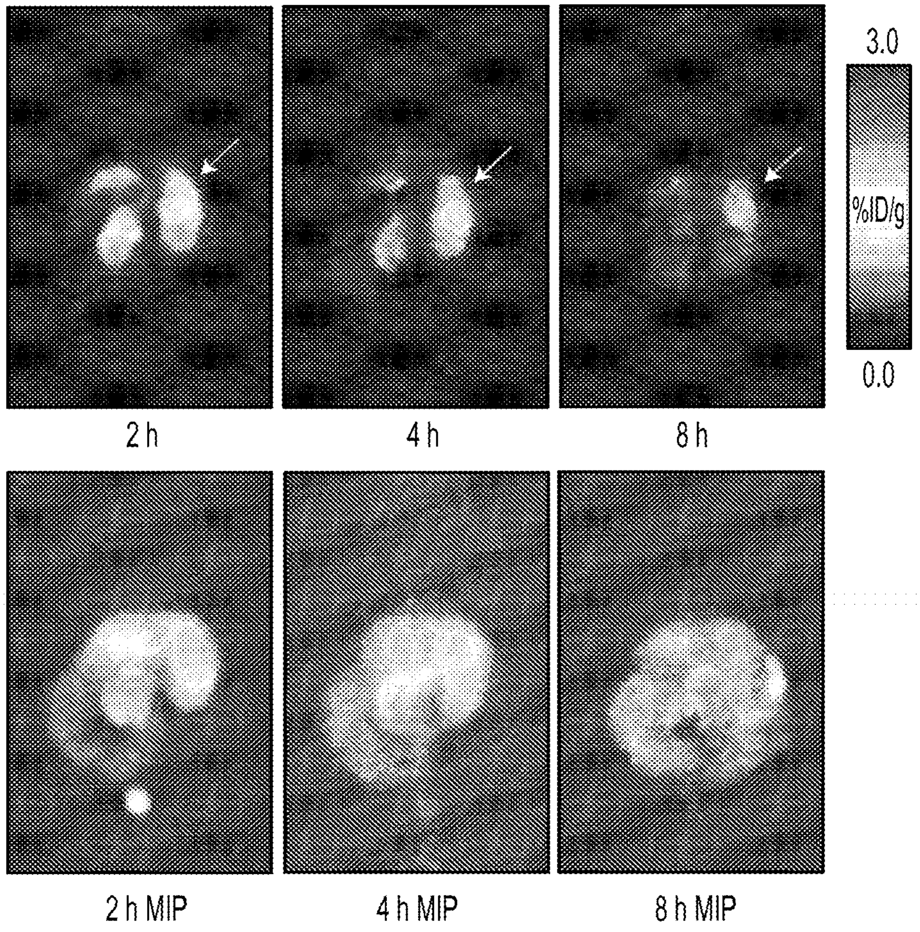
FIG. 14 shows PET imaging data for $^{64}$Cu-Tz-SarAr in a healthy mouse. Healthy female athymic nude mice were administered $^{64}$Cu-Tz-SarAr (300-350 μCi in 200 μL 0.9% sterile saline) via intravenous tail vein injection (t=0). Approximately 5 minutes prior to the PET images, mice were anesthetized by inhalation of 2% isoflurane (Baxter Healthcare, Deerfield, IL)/oxygen gas mixture and placed on the scanner bed; anesthesia was maintained using 1% isoflurane/gas mixture. Static scans were recorded at various time points after injection with a minimum of 30 million coincident events (10-30 min total scan time). Activity concentrations (percentage of dose per gram of tissue [% ID/g]) and maximum intensity projections were determined by conversion of the counting rates from the reconstructed images. All of the resulting PET images were analyzed using ASIPro VM™ software. Maximum intensity projections (MIPs) are shown for each time point, and the coronal slices above are representative images chosen to illustrate the areas of highest uptake (i.e. the kidneys, white arrow).

After synthesis and characterization, in vivo behavior and pharmacokinetics of the $^{64}$Cu-labeled tetrazine radioligands were measured. To this end, acute biodistribution and PET imaging experiments were performed in healthy athymic nude mice injected with $^{64}$Cu-Tz-NOTA, $^{64}$Cu-Tz-$PEG_7$-NOTA, or $^{64}$Cu-Tz-SarAr (FIGS. 12-14 and Tables 5-7). All three $^{64}$Cu-labeled tetrazines minimally accumulated in most healthy non-target tissues, with activity concentrations lower than 0.5% ID/g beyond the earliest time points. Notably, the largest difference between the three radioligands was their excretion profiles. As discussed previously, $^{64}$Cu-Tz-NOTA was excreted relatively slowly through the feces, with 10.0±1.3% ID/g remaining in the large intestine and its contents at 4 h post-injection, a number which dropped to 1.4±0.7% ID/g at 24 h. The addition of the PEG linker in $^{64}$Cu-Tz-$PEG_7$-NOTA caused two distinct changes. First, the elimination of the radioligand through the gut was accelerated, with only 4.9±0.7% ID/g in the large intestine and its contents at 4 h post-injection Second, the kidneys displayed activity concentrations of 1.5±0.2% ID/g and 1.2±0.4% ID/g at 1 h and 4 h, respectively, indicating that a portion of the radiotracer was excreted by the urinary tract. Notably, the largest difference was observed with $^{64}$Cu-Tz-SarAr, which was excreted exclusively and rapidly through the renal system. The tissue with the highest levels of $^{64}$Cu-Tz-SarAr at 1 h post-injection was the kidney, with 2.3±0.4% ID/g. The activity in the kidneys decreased over time; however, at 24 h some retention of the radioligand remained. Complementary PET imaging experiments confirmed the observations from the biodistributions: $^{64}$Cu-Tz-SarAr cleared quickly and cleanly through the urinary tract; $^{64}$Cu-Tz-NOTA was eliminated somewhat sluggishly through the gastrointestinal pathway; and $^{64}$Cu-Tz-PEG$_7$-NOTA represented an intermediate case, with excretion through both the intestines and the kidneys.

Table 5 shows biodistribution data (% ID/g±SD) of $^{64}$Cu-Tz-NOTA versus time in healthy athymic nude (n=4 for each time point). Mice were administered $^{64}$Cu-Tz-NOTA (25-30 μCi in 200 μL 0.9% sterile saline) via intravenous tail vein injection. Animals (n=4 per group) were euthanized by $CO_2$(g) asphyxiation at 1, 4, and 24 h after injection. After asphyxiation, tissues were removed, rinsed in water, dried in air for 5 min, weighed, and counted in a gamma counter calibrated for $^{64}$Cu. Counts were converted into activity using a calibration curve generated from known standards. Count data were background- and decay-corrected to the time of injection, and the percent injected dose per gram (% ID/g) for each tissue sample was calculated by normalization to the total activity injected. Contents within the stomach, small intestine, and large intestine were not removed for the measurements.

TABLE 5

| | 1 h | 4 h | 24 h |
|---|---|---|---|
| Blood | 0.23 ± 0.01 | 0.13 ± 0.01 | 0.07 ± 0.01 |
| Heart | 0.10 ± 0.02 | 0.11 ± 0.02 | 0.09 ± 0.01 |
| Lung | 0.38 ± 0.06 | 0.27 ± 0.08 | 0.21 ± 0.02 |
| Liver | 1.45 ± 0.39 | 0.42 ± 0.13 | 0.21 ± 0.06 |
| Spleen | 0.15 ± 0.05 | 0.09 ± 0.02 | 0.08 ± 0.02 |
| Stomach | 0.12 ± 0.04 | 0.05 ± 0.03 | 0.18 ± 0.11 |
| Large Intestine | 11.58 ± 2.19 | 10.03 ± 1.33 | 1.37 ± 0.65 |
| Small Intestine | 3.14 ± 1.47 | 0.17 ± 0.07 | 0.10 ± 0.02 |
| Kidney | 0.53 ± 0.09 | 0.33 ± 0.07 | 0.22 ± 0.07 |
| Muscle | 0.04 ± 0.02 | 0.03 ± 0.02 | 0.03 ± 0.03 |
| Bone | 0.10 ± 0.03 | 0.07 ± 0.04 | 0.03 ± 0.01 |

Table 6 shows biodistribution data (% ID/g±SD) of $^{64}$Cu-Tz-PEG$_7$-NOTA versus time in healthy athymic nude (n=4 for each time point). Mice were administered $^{64}$Cu-Tz-PEG$_7$-NOTA (25-30 μCi in 200 μL 0.9% sterile saline) via intravenous tail vein injection. Animals (n=4 per group) were euthanized by $CO_2$(g) asphyxiation at 1, 4, and 24 h after injection. After asphyxiation, tissues were removed, rinsed in water, dried in air for 5 min, weighed, and counted in a gamma counter calibrated for $^{64}$Cu. Counts were converted into activity using a calibration curve generated from known standards. Count data were background- and decay-corrected to the time of injection, and the percent injected dose per gram (% ID/g) for each tissue sample was calculated by normalization to the total activity injected. Contents within the stomach, small intestine, and large intestine were not removed for the measurements.

TABLE 6

| | 1 h | 4 h | 24 h |
|---|---|---|---|
| Blood | 0.38 ± 0.14 | 0.26 ± 0.14 | 0.08 ± 0.01 |
| Heart | 0.17 ± 0.02 | 0.18 ± 0.03 | 0.09 ± 0.01 |
| Lung | 0.49 ± 0.11 | 0.35 ± 0.13 | 0.17 ± 0.03 |
| Liver | 0.77 ± 0.11 | 0.63 ± 0.2 | 0.32 ± 0.11 |
| Spleen | 0.19 ± 0.01 | 0.14 ± 0.02 | 0.12 ± 0.01 |
| Stomach | 0.18 ± 0.06 | 0.36 ± 0.25 | 0.09 ± 0.02 |
| Large Intestine | 6.35 ± 0.69 | 4.91 ± 0.71 | 0.40 ± 0.15 |
| Small Intestine | 0.5 ± 0.26 | 0.3 ± 0.14 | 0.10 ± 0.01 |
| Kidney | 1.51 ± 0.24 | 1.23 ± 0.39 | 0.86 ± 0.11 |
| Muscle | 0.05 ± 0.01 | 0.03 ± 0.02 | 0.02 ± 0.01 |
| Bone | 0.09 ± 0.06 | 0.07 ± 0.02 | 0.06 ± 0.01 |

Table 7 shows biodistribution data (0% ID/g±SD) of $^{64}$Cu-Tz-SarAr versus time in healthy athymic nude (n=4 for each time point). Mice were administered $^{64}$Cu-Tz-SarAr (25-30 μCi in 200 μL 0.90 sterile saline) via intravenous tail vein injection. Animals (n=4 per group) were euthanized by $CO_2$(g) asphyxiation at 1, 4, and 24 h after injection. After asphyxiation, tissues were removed, rinsed in water, dried in air for 5 min, weighed, and counted in a gamma counter calibrated for $^{64}$Cu. Counts were converted into activity using a calibration curve generated from known standards. Count data were background- and decay-corrected to the time of injection, and the percent injected dose per gram (0% ID/g) for each tissue sample was calculated by normalization to the total activity injected. Contents within the stomach, small intestine, and large intestine were not removed for the measurements.

TABLE 7

| | 1 h | 4 h | 24 h |
|---|---|---|---|
| Blood | 0.42 ± 0.11 | 0.15 ± 0.01 | 0.06 ± 0.01 |
| Heart | 0.22 ± 0.06 | 0.12 ± 0.02 | 0.08 ± 0.02 |
| Lung | 0.32 ± 0.06 | 0.31 ± 0.09 | 0.24 ± 0.06 |
| Liver | 0.72 ± 0.03 | 0.42 ± 0.24 | 0.28 ± 0.07 |
| Spleen | 0.38 ± 0.06 | 0.2 ± 0.05 | 0.21 ± 0.04 |
| Stomach | 0.24 ± 0.14 | 0.2 ± 0.1 | 0.05 ± 0.01 |
| Large Intestine | 0.07 ± 0.01 | 0.08 ± 0.03 | 0.07 ± 0.01 |
| Small Intestine | 0.29 ± 0.21 | 0.16 ± 0.03 | 0.07 ± 0.01 |
| Kidney | 2.34 ± 0.35 | 1.57 ± 0.19 | 1.26 ± 0.41 |
| Muscle | 0.05 ± 0.03 | 0.04 ± 0.01 | 0.03 ± 0.01 |
| Bone | 0.12 ± 0.03 | 0.09 ± 0.01 | 0.08 ± 0.02 |

Figure 15:
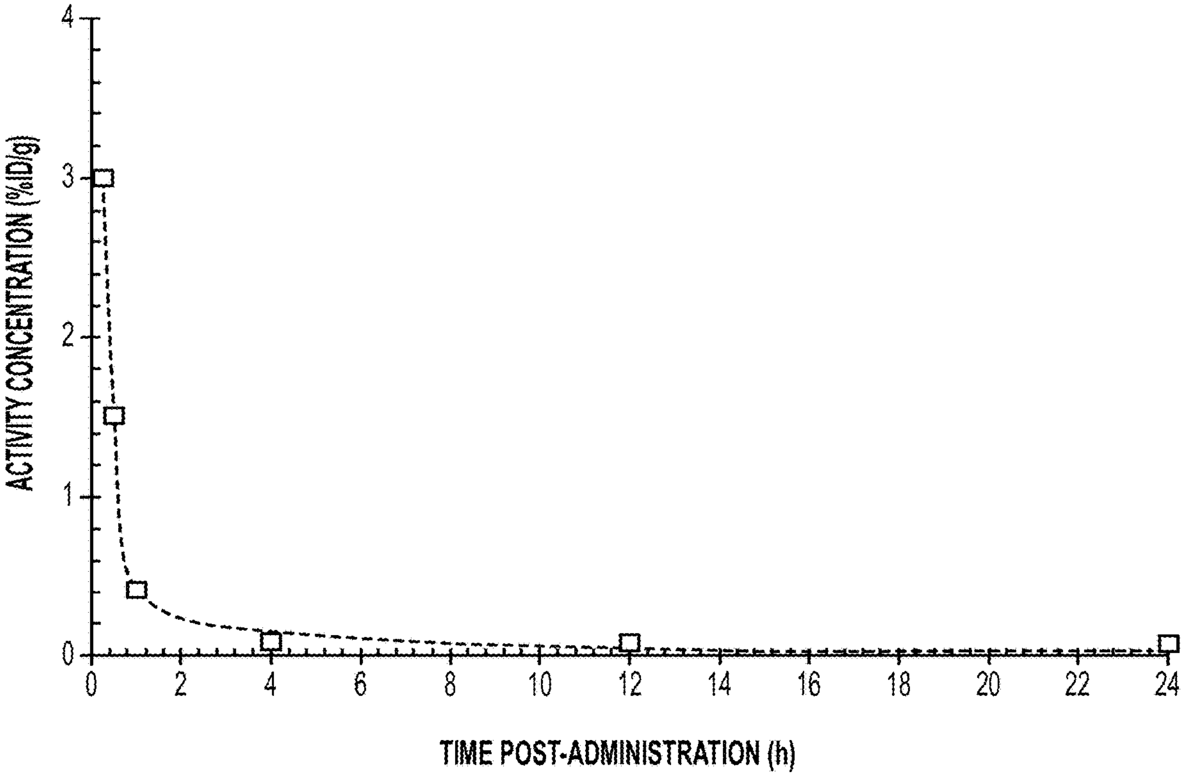
FIG. 15 shows a plot of the clearance of $^{64}$Cu-Tz-SarAr from the blood vs. time (red squares). Fitting of the data points to a biexponential function (dotted line) reveals that greater than 99% of the radioligand clears from the blood with a half-life of ~16 minutes.

Thus, $^{64}$Cu-Tz-SarAr possessed improved elimination pharmacokinetics compared to other pretargeted PET strategies. The radioligand was excreted rapidly via the bladder and kidneys, and the activity concentrations in the large intestine—a critical source of background noise in clinical colorectal cancer imaging—remained remarkably low (e.g., 0.07±0.01% ID/g at 1 h post-injection). Additional experiments were conducted to further interrogate the in vivo performance of $^{64}$Cu-Tz-SarAr. Blood activity measurements, for example, revealed that the vast majority of the radioligand cleared from the blood with a residence time of ~16 minutes (see Table 8 and FIG. 15). Moreover, in vivo stability assays indicated that 96.8±0.8% of the $^{64}$Cu-Tz-SarAr remained intact at 15 minutes post-injection, a value which falls to 82.0±3.3% at 1 h post-injection and ultimately 29.0±5.9% 4 h after administration (see Table 9). These numbers clearly indicated that while $^{64}$Cu-Tz-SarAr was not tremendously stable in vivo, the radioligand unquestionably remained intact during the critical initial blood residence time frame.

Table 8 shows the in vivo blood residence time of $^{64}$Cu-Tz-SarAr in healthy athymic nude mice (n=3).

TABLE 8

| Time | Activity in Blood (%ID/g) |
|---|---|
| 15 min | 3.02 ± 1.10 |
| 30 min | 1.55 ± 0.21 |
| 1 h | 0.42 ± 0.11 |
| 4 h | 0.15 ± 0.01 |
| 12 h | 0.12 ± 0.03 |
| 24 h | 0.06 ± 0.01 |

Table 9 shows percent of $^{64}$Cu-Tz-SarAr intact in blood after vs. time.

TABLE 9

| Time | % Intact $^{64}$Cu-Tz-SarAr |
|---|---|
| 15 min | 96.8 ± 0.8 |
| 1 h | 82.0 ± 3.3 |
| 4 h | 29.0 ± 5.9 |

In Vivo Pretargeting

Figure 16:
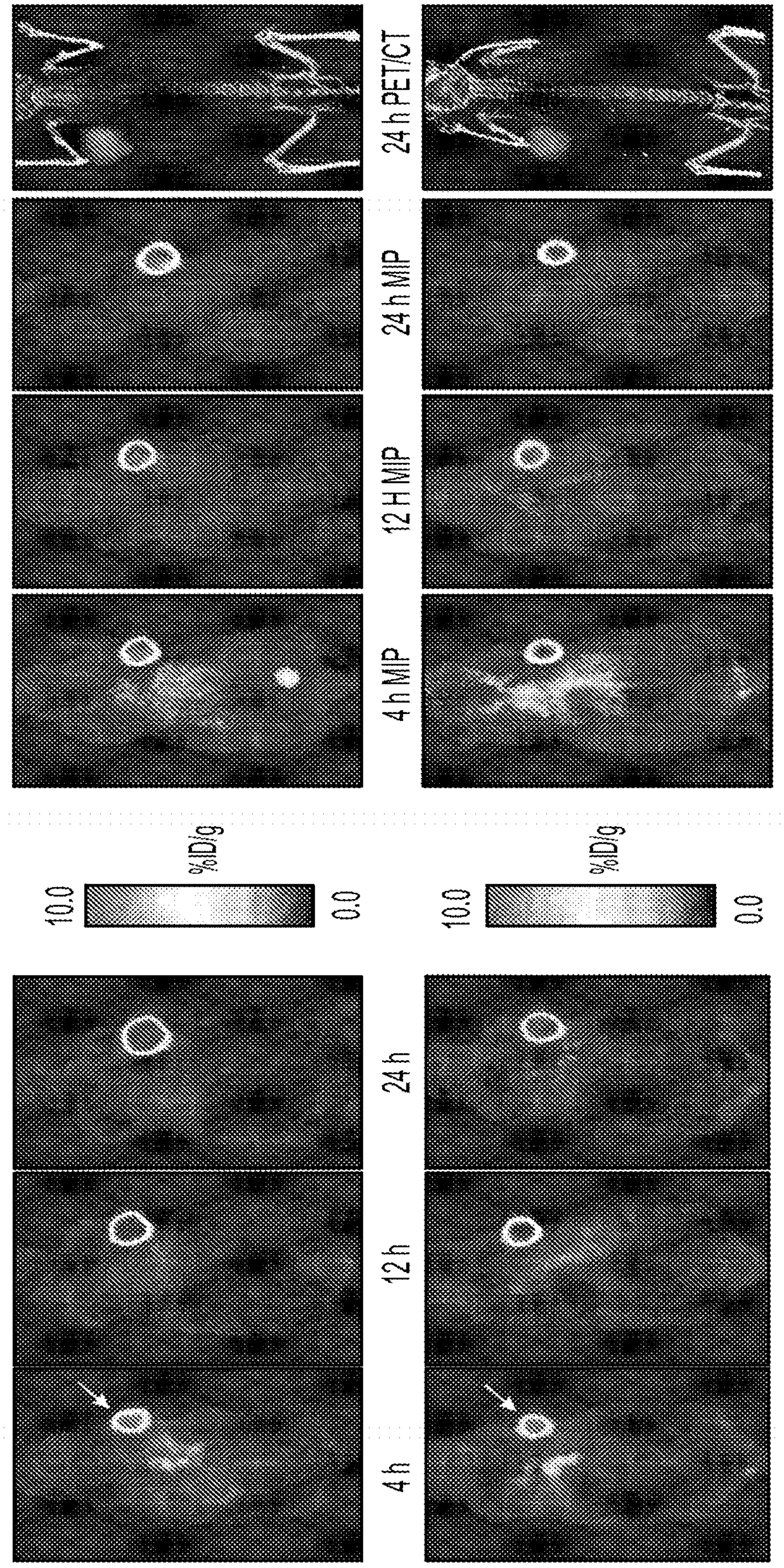
FIG. 16 shows pretargeted PET imaging using $^{64}$Cu-Tz-SarAr and a 24 h accumulation interval. Female athymic nude mice (n=5) bearing subcutaneous SW1222 (right shoulder) xenografts (100-150 mm$^3$, 9-12 days post-inoculation) were administered 100 mg (0.66 nmol) huA33-TCO (in 200 mL 0.9% sterile saline) via intravenous tail vein injection. After an accumulation interval period of 24 h, the same mice were then administered $^{64}$Cu-Tz-SarAr (400-450 μmCi, 0.66-0.77 nmol, in 200 mL 0.9% sterile saline), also via intravenous tail vein injection (t=0). The coronal slices (left) intersect the center of the tumor (white arrow). Maximum intensity projections (MIP) at 4, 12, and 24 h post-injection are also displayed (right), as well as a co-registered PET/CT images collected at 24 h post-injection (far right, perspective flipped).
Figure 17:
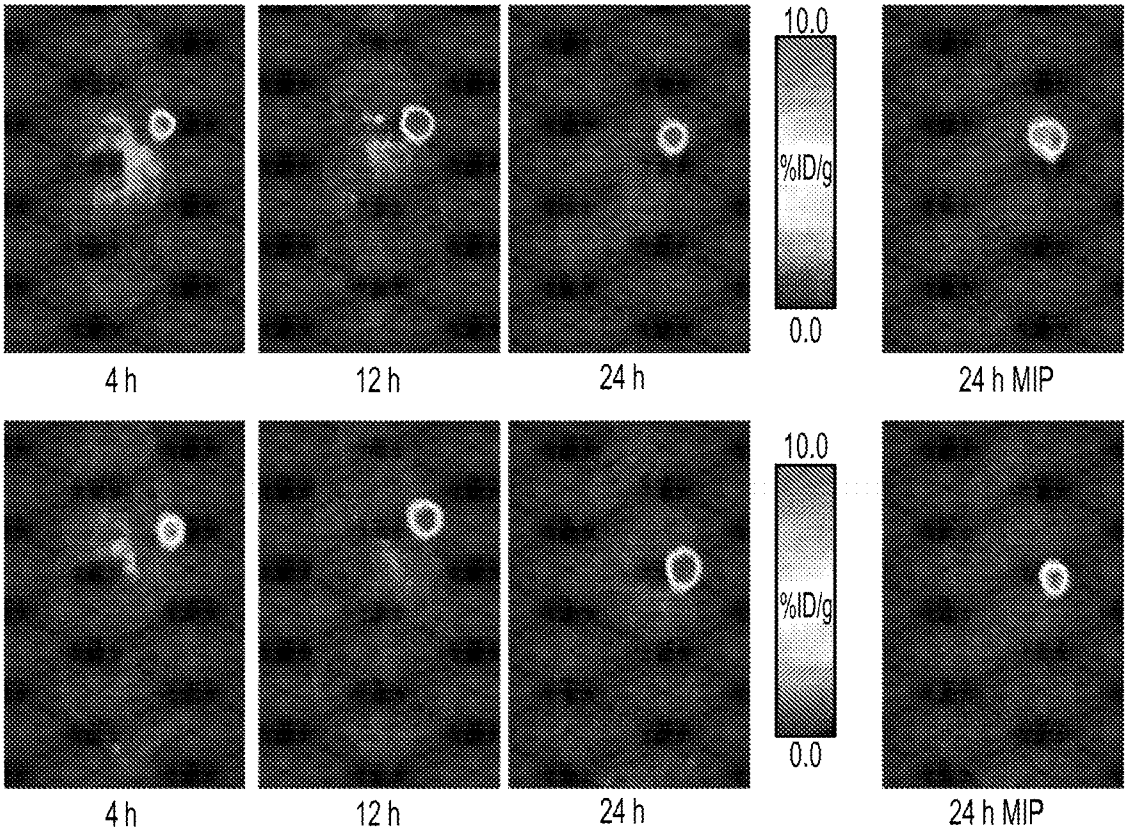
FIG. 17 shows pretargeted PET imaging using $^{64}$Cu-Tz-SarAr and a 24 h accumulation interval. Female athymic nude mice (n=5) bearing subcutaneous SW1222 (right shoulder) xenografts (100-150 mm$^3$, 18-21 days post-inoculation) were administered 100 mg (0.66 nmol) huA33-TCO (in 200 mL 0.9% sterile saline) via intravenous tail vein injection. After an accumulation interval of 24 h, the same mice were then administered $^{64}$Cu-Tz-SarAr (400-450 μCi in 200 mL 0.9% sterile saline), also via intravenous tail vein injection (t=0). The specific activity of $^{64}$Cu-Tz-SarAr was adjusted using cold $^{nat}$Cu-Tz-SarAr such that the molar ratio of $Tz_{injected}$:$huA33_{injected}$=1:1. Static scans were recorded at various time points after injection with a minimum of 30 million coincident events (10-30 min total scan time). Activity concentrations (percentage of dose per gram of tissue [% ID/g]) and maximum intensity projections were determined by conversion of the counting rates from the reconstructed images. All of the resulting PET images were analyzed using ASIPro VM™ software. The coronal slices intersect the center of the tumor, and the maximum intensity projection (MIP) displayed was collected at 24 h post-injection.

Due to its pharmacokinetic profile, $^{64}$Cu-Tz-SarAr was selected for in vivo pretargeting experiments. To this end, athymic nude mice bearing A33 antigen-expressing SW1222 human colorectal carcinoma tumors were first injected with huA33-TCO (100 μg). After a 24 h interval during which huA33-TCO accumulated at the tumor and cleared from the blood, the mice were injected with $^{64}$Cu-Tz-SarAr (400-450 μCi). The specific activity of the radiotracer was adjusted using cold $^{cat}$Cu-Tz-SarAr such that the molar ratio of Tz-SarAr:huA33-TCO≈1:1. Both the PET imaging (FIG. 16 and FIG. 17) and biodistribution results (Tables 10-12) indicated that the strategy quickly and clearly delineated colorectal carcinoma tissue with low activity concentrations in non-target tissues. At 1 h post-injection, the activity concentration in the tumor (5.63±0.67% ID/g) was the highest of all tissues surveyed, while the blood (4.2±0.8% ID/g) and kidneys (3.1±0.3% ID/g) were the healthy organs with the highest background activity concentrations. Notably, over the course of the experiment, the activity in the non-target tissues cleared. For example, at 24 h post-injection, the activity concentration in the blood and kidneys was reduced to 2.2±0.4% ID/g and 1.9±0.4% ID/g, respectively, while the tumoral activity concentration at the same time point was 6.7±1.3% ID/g. Furthermore, all other non-target tissues contained less than 1.5% ID/g at these later time points. Moreover, the tumor-to-background activity ratios were favorable at early time points (e.g., tumor:muscle=14.9±2.9 at 1 h post-injection) and increased to 45.12±8.5 at 12 h and 37.37±16.1 at 24 h (Table 11). Control PET imaging experiments were run using $^{64}$Cu-Tz-SarAr alone as well as $^{64}$Cu-Tz-SarAr with unmodified huA33. As expected, both cases resulted in minimal (less than 0.5% ID/g) uptake by the tumor.

Table 10 shows the biodistribution of $^{64}$Cu-Tz-SarAr pretargeting experiment with a 24 h accumulation interval. Female athymic nude mice bearing subcutaneous SW1222 (right shoulder) xenografts (100-150 $mm^3$, 18-21 days post-inoculation) were administered 100 μg (0.66 nmol) huA33-TCO (in 200 μL 0.9% sterile saline) via intravenous tail vein injection. After an accumulation interval of 24 h, the same mice were then administered $^{64}$Cu-Tz-SarAr (300-350 μCi in 200 μL 0.9% sterile saline), also via intravenous tail vein injection (t=0). The specific activity of the radiotracer was adjusted using cold $^{cat}$Cu-Tz-SarAr such that the molar ratio of $Tz_{injected}$:$huA33_{injected}$=1:1. Animals (n=4 per group) were euthanized by $CO_2(g)$ asphyxiation at 1, 4, 12, and 24 h after injection. After asphyxiation, 13 tissues were removed, rinsed in water, dried in air for 5 min, weighed, and counted in a gamma counter calibrated for $^{64}$Cu. Counts were converted into activity using a calibration curve generated from known standards. Count data were background- and decay-corrected to the time of injection, and the percent injected dose per gram (% ID/g) for each tissue sample was calculated by normalization to the total activity injected. Contents within the stomach, small intestine, and large intestine were not removed for the measurements.

TABLE 10

| | 1 h | 4 h | 12 h | 24 h |
|---|---|---|---|---|
| Blood | 4.20 ± 0.80 | 4.00 ± 0.37 | 2.19 ± 0.39 | 2.61 ± 0.20 |
| Tumor | 5.63 ± 0.67 | 5.56 ± 0.91 | 6.74 ± 1.26 | 7.38 ± 2.02 |
| Heart | 1.81 ± 0.46 | 1.45 ± 0.03 | 0.84 ± 0.1 | 0.81 ± 0.04 |
| Lung | 1.65 ± 0.51 | 1.55 ± 0.45 | 1.24 ± 0.22 | 0.99 ± 0.24 |
| Liver | 1.60 ± 0.12 | 1.45 ± 0.21 | 1.33 ± 0.53 | 1.51 ± 0.2 |
| Spleen | 0.98 ± 0.25 | 0.81 ± 0.20 | 0.65 ± 0.17 | 0.64 ± 0.04 |
| Stomach | 0.73 ± 0.19 | 0.56 ± 0.20 | 0.21 ± 0.1 | 0.28 ± 0.07 |
| Large Intestine | 0.21 ± 0.09 | 0.48 ± 0.09 | 0.20 ± 0.04 | 0.26 ± 0.06 |
| Blood | 4.20 ± 0.80 | 4.00 ± 0.37 | 2.19 ± 0.39 | 2.61 ± 0.20 |
| Small Intestine | 0.88 ± 0.09 | 0.62 ± 0.06 | 0.35 ± 0.08 | 0.45 ± 0.07 |
| Kidney | 3.08 ± 0.28 | 2.77 ± 0.57 | 1.87 ± 0.42 | 2.00 ± 0.24 |
| Muscle | 0.38 ± 0.06 | 0.37 ± 0.07 | 0.15 ± 0.01 | 0.20 ± 0.07 |
| Bone | 0.67 ± 0.14 | 0.34 ± 0.18 | 0.23 ± 0.05 | 0.29 ± 0.05 |

Table 11 shows tumor-to-tissue activity concentration ratios derived from the $^{64}$Cu-Tz-SarAr pretargeting biodistribution experiment with a 24 h accumulation interval as shown in Table 10.

TABLE 11

| | 1 h | 4 h | 12 h | 24 h |
|---|---|---|---|---|
| Tumor/Blood | 1.34 ± 0.30 | 1.39 ± 0.26 | 3.07 ± 0.79 | 2.83 ± 0.81 |
| Tumor/Heart | 3.11 ± 0.87 | 3.84 ± 0.63 | 8.01 ± 1.77 | 9.10 ± 2.54 |
| Tumor/Lung | 3.40 ± 1.12 | 3.59 ± 1.20 | 5.43 ± 1.41 | 7.44 ± 2.74 |
| Tumor/Liver | 3.52 ± 0.49 | 3.83 ± 0.83 | 5.06 ± 2.23 | 4.87 ± 1.48 |
| Tumor/Spleen | 5.75 ± 1.61 | 6.88 ± 2.01 | 10.34 ± 3.27 | 11.45 ± 3.20 |
| Tumor/ Stomach | 7.75 ± 2.24 | 9.91 ± 3.85 | 31.76 ± 16.62 | 26.44 ± 9.89 |
| Tumor/Large Intestine | 26.88 ± 12.11 | 11.65 ± 2.99 | 33.67 ± 8.82 | 28.86 ± 10.28 |
| Tumor/Small Intestine | 6.42 ± 1.01 | 8.96 ± 1.71 | 19.37 ± 5.95 | 16.33 ± 5.12 |
| Tumor/Kidney | 1.83 ± 0.27 | 2.00 ± 0.53 | 3.61 ± 1.05 | 3.68 ± 1.10 |
| Tumor/Muscle | 14.92 ± 2.85 | 14.84 ± 3.69 | 45.12 ± 8.55 | 37.37 ± 16.06 |
| Tumor/Bone | 8.43 ± 2.07 | 16.15 ± 8.89 | 29.8 ± 8.38 | 25.46 ± 8.22 |

Table 12 shows biodistribution data for in vivo pretargeting experiment using $^{64}$Cu-Tz-SarAr and a 24 h accumulation interval.

TABLE 12

| | 1 h | 4 h | 12 h | 24 h |
|---|---|---|---|---|
| Blood | 4.20 ± 0.80[a] | 4.00 ± 0.37 | 2.19 ± 0.39 | 2.61 ± 0.20 |
| Tumor | 5.63 ± 0.67 | 5.56 ± 0.91 | 6.74 ± 1.26 | 7.38 ± 2.02 |
| Heart | 1.81 ± 0.46 | 1.45 ± 0.03 | 0.84 ± 0.10 | 0.81 ± 0.04 |
| Lung | 1.65 ± 0.51 | 1.55 ± 0.45 | 1.24 ± 0.22 | 0.99 ± 0.24 |
| Liver | 1.60 ± 0.12 | 1.45 ± 0.21 | 1.33 ± 0.53 | 1.51 ± 0.20 |
| Spleen | 0.98 ± 0.25 | 0.81 ± 0.20 | 0.65 ± 0.17 | 0.64 ± 0.04 |
| Stomach | 0.73 ± 0.19 | 0.56 ± 0.20 | 0.21 ± 0.10 | 0.28 ± 0.07 |
| Large Intestine | 0.21 ± 0.09 | 0.48 ± 0.09 | 0.20 ± 0.04 | 0.26 ± 0.06 |
| Small Intestine | 0.88 ± 0.09 | 0.62 ± 0.06 | 0.35 ± 0.08 | 0.45 ± 0.07 |
| Kidney | 3.08 ± 0.28 | 2.77 ± 0.57 | 1.87 ± 0.42 | 2.00 ± 0.24 |
| Blood | 4.20 ± 0.80[a] | 4.00 ± 0.37 | 2.19 ± 0.39 | 2.61 ± 0.20 |
| Muscle | 0.38 ± 0.06 | 0.37 ± 0.07 | 0.15 ± 0.01 | 0.20 ± 0.07 |
| Bone | 0.67 ± 0.14 | 0.34 ± 0.18 | 0.23 ± 0.05 | 0.29 ± 0.05 |

[a]Values are % ID/g ± SD. Mice (n = 4) bearing subcutaneous SW1222 xenografts were administered huA33-TCO via tail vein injection. After 24 h, the same mice were administered $^{64}$Cu-Tz-SarAr, also via tail vein injection.

Figure 26:
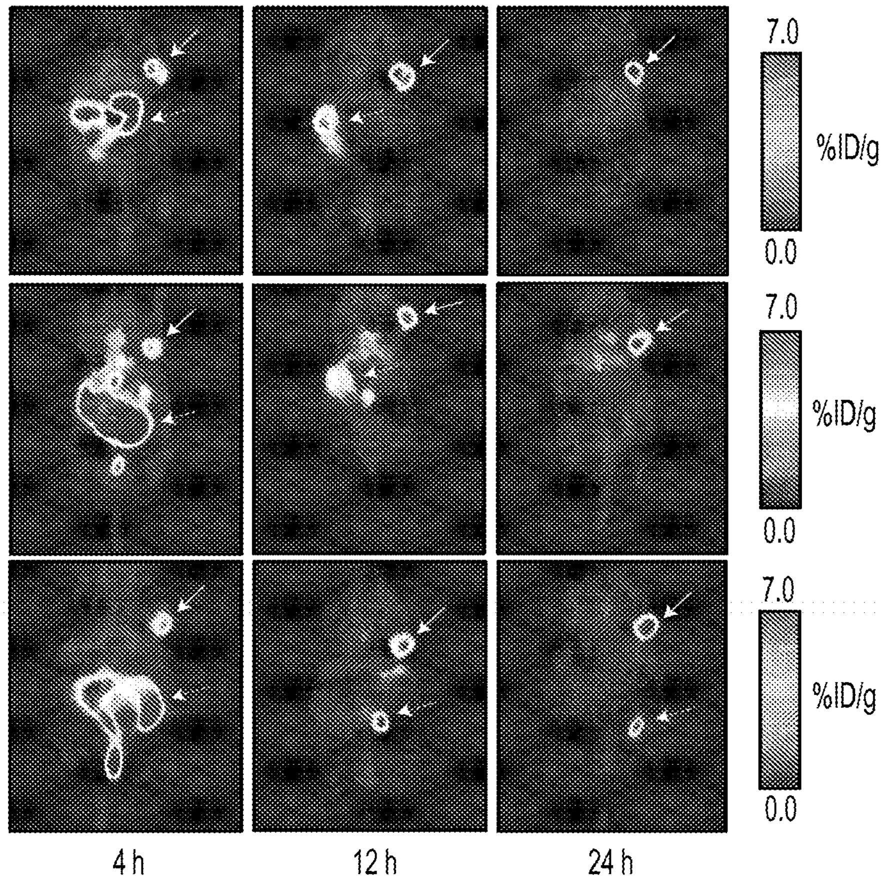
FIG. 26 shows pretargeted PET imaging using $^{64}$Cu-Tz-NOTA. Female athymic nude mice (n=5) bearing subcutaneous SW1222 (right shoulder) xenografts (100-150 mm$^3$, 18-21 days post-inoculation) were administered 100 mg (0.66 nmol) huA33-TCO (in 200 mL 0.9% sterile saline) via intravenous tail vein injection. After an accumulation interval of 24 h, the same mice were then administered $^{64}$Cu-Tz-NOTA (400-450 µCi in 200 mL 0.9% sterile saline), also via intravenous tail vein injection (t=0). The specific activity of $^{64}$Cu-Tz-NOTA was adjusted using cold $^{cat}$Cu-Tz-NOTA such that the molar ratio of $Tz_{injected}$:$huA33_{injected}$=1:1. Static scans were recorded at various time points after injection with a minimum of 30 million coincident events (10-30 min total scan time). Activity concentrations (percentage of dose per gram of tissue [% ID/g]) and maximum intensity projections were determined by conversion of the counting rates from the reconstructed images. All of the resulting PET images were analyzed using ASIPro VM™ software. The coronal slices intersect the center of the tumor (solid white arrow), and the maximum intensity projection (MIP) displayed was collected at 24 h post-injection. Note the activity not only in the SW1222 xenograft but also in the gut of the mouse (dashed white arrow) at 4 h post-injection.

Moreover, the PET imaging and biodistribution data for both designed systems outperformed the $^{64}$Cu-Tz-NOTA system (FIG. 26 and Tables 13-14). First, the activity concentrations in the tumor were higher using the $^{64}$Cu-Tz-SarAr approach. For example, $^{64}$Cu-Tz-SarAr demonstrated an activity concentration of 5.56±0.91% ID/g in the tumor whereas $^{64}$Cu-Tz-NOTA demonstrated an activity concentration of 4.09±0.61% ID/g at the same time-point of 4 h post-injection Second, the chelator structure alteration disclosed herein achieved higher tumor-to-background activity ratios compared to the $^{64}$Cu-Tz-NOTA radioligand. For example, at 12 h after injection, the tumor-to-muscle and tumor-to-blood activity ratios for $^{64}$Cu-Tz-SarAr were 3.1±0.8 and 45.1±8.6, respectively, compared to 1.8±0.5 and 26.6±6.6 for $^{64}$Cu-Tz-NOTA. Third, the clearance of the $^{64}$Cu-Tz-SarAr and $^{64}$Cu-Tz-NOTA radiotracers through the GI tract differed. For example, at 1 h post-injection, the activity concentration of $^{64}$Cu-Tz-NOTA in the large intestine and its contents was 13.29±3.15% ID/g compared to an activity concentration of 0.21±0.09% ID/g for $^{64}$Cu-Tz-SarAr. This caused the tumor-to-large intestine activity ratio to be 1.44±0.72 for $^{64}$Cu-Tz-NOTA to 33.67±8.82 for $^{64}$Cu-Tz-SarAr at 12 h post-injection However, the $^{64}$Cu-Tz-SarAr system exhibited higher activity concentrations in its clearance organs, the kidneys. Still, the activity levels of $^{64}$Cu-Tz-SarAr in the kidneys were generally below activity levels of $^{64}$Cu-Tz-NOTA measured in the gut. It is important to note that low levels of residual uptake in the kidneys will not significantly interfere with clinical imaging of primary colorectal carcinoma unlike uptake in the large intestine.

Table 13 shows the biodistribution of $^{64}$Cu-Tz-NOTA with a 24 h accumulation interval. Contents within the stomach, small intestine, and large intestine were not removed for the measurements. This data was originally published in *JNM*. Zeglis, B. M. et al. "A pretargeted PET imaging strategy based on bioorthogonal Diels-Alder click chemistry." *Journal of Nuclear Medicine*. 54, 1389-1396 (2013). ©2013 by the Society of Nuclear Medicine and Molecular Imaging, Inc.

TABLE 13

| | 1 h | 4 h | 12 h | 24 h |
|---|---|---|---|---|
| Blood | 3.47 ± 0.63 | 2.61 ± 0.83 | 2.31 ± 0.4 | 2.07 ± 0.49 |
| Tumor | 4.07 ± 0.25 | 4.09 ± 0.61 | 4.20 ± 0.84 | 3.94 ± 0.92 |
| Heart | 1.09 ± 0.18 | 0.91 ± 0.27 | 0.92 ± 0.14 | 0.82 ± 0.21 |
| Lung | 1.58 ± 0.46 | 1.6 ± 0.39 | 1.09 ± 0.38 | 1.03 ± 0.31 |
| Liver | 2.19 ± 0.25 | 1.26 ± 0.3 | 0.93 ± 0.23 | 1.07 ± 0.15 |
| Spleen | 0.63 ± 0.07 | 0.51 ± 0.22 | 0.59 ± 0.25 | 0.45 ± 0.11 |
| Stomach | 0.45 ± 0.08 | 0.25 ± 0.12 | 0.52 ± 0.64 | 0.16 ± 0.03 |
| Large Intestine | 13.29 ± 3.15 | 9.43 ± 4.22 | 2.92 ± 1.34 | 1.67 ± 0.88 |
| Small Intestine | 0.03 ± 0.04 | 0.38 ± 0.08 | 0.77 ± 0.51 | 0.35 ± 0.04 |
| Kidney | 1.3 ± 0.15 | 0.95 ± 0.31 | 0.91 ± 0.29 | 0.7 ± 0.19 |
| Muscle | 0.22 ± 0.04 | 0.14 ± 0.03 | 0.16 ± 0.02 | 0.15 ± 0.02 |
| Bone | 0.3 ± 0.16 | 0.27 ± 0.24 | 0.35 ± 0.11 | 0.29 ± 0.07 |

Table 14 shows tumor-to-tissue activity concentration ratios of $^{64}$Cu-Tz-NOTA pretargeting experiment with a 24 h accumulation interval. This data was originally published in *JNM*. Zeglis, B. M. et al. "A pretargeted PET imaging strategy based on bioorthogonal Diels-Alder click chemistry." *Journal of Nuclear Medicine*. 54, 1389-1396 (2013). ©2013 by the Society of Nuclear Medicine and Molecular Imaging, Inc.

TABLE 14

| | 1 h | 4 h | 12 h | 24 h |
|---|---|---|---|---|
| Tumor/Blood | 1.17 ± 0.22 | 1.57 ± 0.55 | 1.82 ± 0.48 | 1.9 ± 0.63 |
| Tumor/Heart | 3.75 ± 0.65 | 4.51 ± 1.49 | 4.58 ± 1.16 | 4.82 ± 1.69 |
| Tumor/Blood | 1.17 ± 0.22 | 1.57 ± 0.55 | 1.82 ± 0.48 | 1.9 ± 0.63 |
| Tumor/Lung | 2.57 ± 0.76 | 2.55 ± 0.73 | 3.87 ± 1.55 | 3.83 ± 1.45 |
| Tumor/Liver | 1.86 ± 0.24 | 3.23 ± 0.9 | 4.53 ± 1.45 | 3.69 ± 1.01 |
| Tumor/Spleen | 6.46 ± 0.81 | 7.97 ± 3.57 | 7.1 ± 3.34 | 8.79 ± 2.98 |
| Tumor/ Stomach | 8.96 ± 1.7 | 16.17 ± 8.21 | 8.12 ± 10.12 | 24.29 ± 6.89 |
| Tumor/Large Intestine | 0.31 ± 0.08 | 0.43 ± 0.2 | 1.44 ± 0.72 | 2.36 ± 1.37 |

TABLE 14-continued

| | 1 h | 4 h | 12 h | 24 h |
|---|---|---|---|---|
| Tumor/Small Intestine | 119.52 ± 148.82 | 10.83 ± 2.8 | 5.46 ± 3.81 | 11.4 ± 2.91 |
| Tumor/Kidney | 3.14 ± 0.41 | 4.32 ± 1.56 | 4.6 ± 1.71 | 5.61 ± 1.98 |
| Tumor/Muscle | 18.42 ± 3.71 | 29.38 ± 8.5 | 26.63 ± 6.59 | 26.98 ± 7.41 |
| Tumor/Bone | 13.72 ± 7.63 | 14.95 ± 13.2 | 11.98 ± 4.51 | 13.43 ± 4.5 |

With a 24 h accumulation interval, the activity concentration of $^{64}$Cu-Tz-SarAr in the tumor reached a relatively high 5.63±0.67% ID/g at 1 h post-injection This value increased slightly over the course of the experiment to 6.74±1.26% ID/g at 12 h and 7.38±2.02% ID/g at 24 h. These data, combined with the relatively high blood activity values, suggested that while the majority of the in vivo ligations occurred at the tumor, some radioligands clicked with the antibody in the blood and reached the tumor thereafter. Therefore, in an attempt to decrease the frequency of click reactions in the blood and reduce non-target tissue activity concentrations, PET imaging and biodistribution experiments were conducted using longer accumulation intervals of 48 and 120 h (FIGS. 18A-18B and FIGS. 19-24 and Tables 15-22).

Table 15 shows the biodistribution of $^{64}$Cu-Tz-SarAr pretargeting experiment with a 48 h accumulation interval. Female athymic nude mice bearing subcutaneous SW1222 (right shoulder) xenografts (100-150 $mm^3$, 18-21 days post-inoculation) were administered 100 μg (0.66 nmol) huA33-TCO (in 200 μL 0.9% sterile saline) via intravenous tail vein injection. After an accumulation interval of 48 h, the same mice were then administered $^{64}$Cu-Tz-SarAr (300-350 μCi in 200 μL 0.9% sterile saline) via intravenous tail vein injection (t=0). The specific activity of the radiotracer was adjusted using cold $^{cat}$Cu-Tz-SarAr such that the molar ratio of $Tz_{injected}$:$huA33_{injected}$=1:1. Animals (n=4 per group) were euthanized by $CO_2$(g) asphyxiation at 1, 4, 12, and 24 h after injection. After asphyxiation, tissues were removed, rinsed in water, dried in air for 5 min, weighed, and counted in a gamma counter calibrated for $^{64}$Cu. Counts were converted into activity using a calibration curve generated from known standards. Count data were background- and decay-corrected to the time of injection, and the percent injected dose per gram (% ID/g) for each tissue sample was calculated by normalization to the total activity injected. Contents within the stomach, small intestine, and large intestine were not removed for the measurements.

TABLE 15

| | 1 h | 4 h | 12 h | 24 h |
|---|---|---|---|---|
| Blood | 2.15 ± 0.5 | 1.78 ± 0.28 | 1.81 ± 0.54 | 0.92 ± 0.31 |
| Tumor | 4.49 ± 0.44 | 5.15 ± 1.42 | 4.94 ± 1.12 | 4.85 ± 0.67 |
| Heart | 1.05 ± 0.24 | 1.08 ± 0.32 | 0.88 ± 0.33 | 0.45 ± 0.08 |
| Lung | 1.68 ± 0.09 | 1.53 ± 0.28 | 1.00 ± 0.18 | 1.05 ± 0.51 |
| Liver | 1.79 ± 0.09 | 1.27 ± 0.19 | 1.08 ± 0.32 | 1.28 ± 0.33 |
| Spleen | 0.84 ± 0.27 | 0.6 ± 0.09 | 0.56 ± 0.11 | 0.5 ± 0.1 |
| Stomach | 0.39 ± 0.17 | 0.27 ± 0.18 | 0.12 ± 0.04 | 0.15 ± 0.03 |
| Large Intestine | 0.29 ± 0.09 | 0.41 ± 0.11 | 0.22 ± 0.08 | 0.16 ± 0.03 |
| Small Intestine | 0.54 ± 0.15 | 0.33 ± 0.1 | 0.3 ± 0.08 | 0.22 ± 0.07 |
| Kidney | 1.98 ± 0.26 | 1.83 ± 0.57 | 2.04 ± 0.36 | 1.47 ± 0.43 |
| Muscle | 0.22 ± 0.11 | 0.24 ± 0.08 | 0.15 ± 0.02 | 0.11 ± 0.04 |
| Bone | 0.23 ± 0.05 | 0.32 ± 0.12 | 0.3 ± 0.07 | 0.18 ± 0.05 |

Table 16 shows tumor-to-tissue activity concentration ratios derived from the $^{64}$Cu-Tz-SarAr pretargeting biodistribution experiment with a 48 h accumulation interval as shown in Table 15.

TABLE 16

| | 1 h | 4 h | 12 h | 24 h |
|---|---|---|---|---|
| Tumor/Blood | 2.09 ± 0.52 | 2.9 ± 0.92 | 2.72 ± 1.03 | 5.27 ± 1.92 |
| Tumor/Heart | 4.27 ± 1.05 | 4.75 ± 1.92 | 5.62 ± 2.47 | 10.9 ± 2.55 |
| Tumor/Lung | 2.67 ± 0.3 | 3.37 ± 1.11 | 4.94 ± 1.45 | 4.61 ± 2.32 |
| Tumor/Liver | 2.51 ± 0.27 | 4.06 ± 1.27 | 4.58 ± 1.69 | 3.8 ± 1.11 |
| Tumor/Spleen | 5.34 ± 1.79 | 8.55 ± 2.69 | 8.75 ± 2.61 | 9.8 ± 2.47 |
| Tumor/Stomach | 11.57 ± 5.25 | 18.92 ± 13.29 | 41.88 ± 18.35 | 32.81 ± 8.37 |
| Tumor/Blood | 2.09 ± 0.52 | 2.9 ± 0.92 | 2.72 ± 1.03 | 5.27 ± 1.92 |
| Tumor/Large Intestine | 15.48 ± 5.25 | 12.68 ± 4.87 | 22.66 ± 10.19 | 29.58 ± 6.11 |
| Tumor/Small Intestine | 8.35 ± 2.48 | 15.71 ± 6.48 | 16.47 ± 5.62 | 21.72 ± 7.59 |
| Tumor/Kidney | 2.27 ± 0.37 | 2.81 ± 1.16 | 2.42 ± 0.7 | 3.31 ± 1.07 |
| Tumor/Muscle | 20.34 ± 10.25 | 21.84 ± 9.2 | 33.88 ± 9.31 | 44.18 ± 17.61 |
| Tumor/Bone | 19.48 ± 4.94 | 15.86 ± 7.12 | 16.24 ± 5.16 | 26.55 ± 7.58 |

Table 17 shows the biodistribution of $^{64}$Cu-Tz-SarAr pretargeting experiment with a 120 h accumulation interval. Female athymic nude mice bearing subcutaneous SW1222 (right shoulder) xenografts (100-150 $mm^3$, 18-21 days post-inoculation) were administered 100 μg (0.66 nmol) huA33-TCO (in 200 μL 0.9% sterile saline) via intravenous tail vein injection. After an accumulation interval of 120 h, the same mice were then administered $^{64}$Cu-Tz-SarAr (300-350 μCi in 200 μL 0.9% sterile saline) via intravenous tail vein injection (t=0). The specific activity of the radiotracer was adjusted using cold $^{cat}$Cu-Tz-SarAr such that the molar ratio of $Tz_{injected}$:huA33$_{injected}$=1:1. Animals (n=4 per group) were euthanized by $CO_2$(g) asphyxiation at 1, 4, 12, and 24 h after injection. After asphyxiation, tissues were removed, rinsed in water, dried in air for 5 min, weighed, and counted in a gamma counter calibrated for $^{64}$Cu. Counts were converted into activity using a calibration curve generated from known standards. Count data were background- and decay-corrected to the time of injection, and the percent injected dose per gram (% ID/g) for each tissue sample was calculated by normalization to the total activity injected. Contents within the stomach, small intestine, and large intestine were not removed for the measurements.

TABLE 17

| | 1 h | 4 h | 12 h | 24 h |
|---|---|---|---|---|
| Blood | 1.39 ± 0.19 | 1.05 ± 0.29 | 0.44 ± 0.14 | 0.75 ± 0.23 |
| Tumor | 3.61 ± 0.45 | 3.55 ± 0.74 | 3.29 ± 0.40 | 4.34 ± 0.98 |
| Heart | 0.52 ± 0.06 | 0.43 ± 0.11 | 0.34 ± 0.20 | 0.40 ± 0.16 |
| Lung | 1.41 ± 0.21 | 0.91 ± 0.22 | 0.59 ± 0.27 | 0.85 ± 0.29 |
| Liver | 1.65 ± 0.07 | 1.16 ± 0.39 | 0.96 ± 0.09 | 1.06 ± 0.16 |
| Blood | 1.39 ± 0.19 | 1.05 ± 0.29 | 0.44 ± 0.14 | 0.75 ± 0.23 |
| Spleen | 0.60 ± 0.13 | 0.50 ± 0.05 | 0.34 ± 0.14 | 0.69 ± 0.17 |
| Stomach | 0.32 ± 0.13 | 0.25 ± 0.12 | 0.09 ± 0.03 | 0.15 ± 0.08 |
| Large Intestine | 0.29 ± 0.16 | 0.20 ± 0.13 | 0.09 ± 0.03 | 0.16 ± 0.04 |
| Small Intestine | 0.34 ± 0.03 | 0.22 ± 0.03 | 0.15 ± 0.07 | 0.17 ± 0.06 |
| Kidney | 1.80 ± 0.12 | 2.10 ± 0.20 | 2.11 ± 0.13 | 1.90 ± 0.17 |
| Muscle | 0.20 ± 0.03 | 0.11 ± 0.05 | 0.08 ± 0.04 | 0.14 ± 0.05 |
| Bone | 0.21 ± 0.03 | 0.16 ± 0.04 | 0.11 ± 0.04 | 0.25 ± 0.08 |

Table 18 shows tumor-to-tissue activity concentration ratios derived from the $^{64}$Cu-Tz-SarAr pretargeting biodistribution experiment with a 120 h accumulation interval as shown in Table 17.

TABLE 18

| | 1 h | 4 h | 12 h | 24 h |
|---|---|---|---|---|
| Tumor/Blood | 2.61 ± 0.48 | 3.37 ± 1.16 | 7.46 ± 2.54 | 5.74 ± 2.17 |
| Tumor/Heart | 7.00 ± 1.22 | 8.24 ± 2.71 | 9.56 ± 5.64 | 10.76 ± 4.94 |

TABLE 18-continued

| | 1 h | 4 h | 12 h | 24 h |
|---|---|---|---|---|
| Tumor/Lung | 2.55 ± 0.49 | 3.89 ± 1.23 | 5.55 ± 2.62 | 5.09 ± 2.06 |
| Tumor/Liver | 2.19 ± 0.29 | 3.06 ± 1.20 | 3.43 ± 0.52 | 4.09 ± 1.13 |
| Tumor/Spleen | 6.02 ± 1.46 | 7.03 ± 1.64 | 9.63 ± 4.03 | 6.26 ± 2.09 |
| Tumor/Stomach | 11.37 ± 4.88 | 14.04 ± 7.07 | 38.07 ± 12.42 | 29.21 ± 17.97 |
| Tumor/Large Intestine | 12.39 ± 7.14 | 17.82 ± 12.22 | 35.43 ± 12.17 | 26.48 ± 8.29 |
| Tumor/Small Intestine | 10.53 ± 1.58 | 16.22 ± 3.91 | 21.47 ± 9.60 | 25.34 ± 10.4 |
| Tumor/Kidney | 2.01 ± 0.29 | 1.69 ± 0.39 | 1.56 ± 0.21 | 2.29 ± 0.56 |
| Tumor/Muscle | 18.41 ± 3.47 | 32.58 ± 16.17 | 38.74 ± 20.11 | 30.39 ± 11.94 |
| Tumor/Bone | 17.27 ± 3.03 | 21.53 ± 7.14 | 29.07 ± 11.14 | 17.16 ± 6.90 |

Table 19 shows a comparison of salient tumor-to-tissue activity concentration ratios at 1 h post-injection created using the different pretargeted PET imaging strategies discussed (see Tables 11, 14, 16, and 18).

TABLE 19

| Radioligand Accumulation | $^{64}$Cu-Tz-NOTA | $^{64}$Cu-Tz-SarAr | | |
|---|---|---|---|---|
| Interval | 24 h | 24 h | 48 h | 120 h |
| Tumor/Blood | 1.17 ± 0.22 | 1.34 ± 0.3 | 2.09 ± 0.52 | 2.61 ± 0.48 |
| Tumor/Liver | 1.86 ± 0.24 | 3.52 ± 0.49 | 2.51 ± 0.27 | 2.19 ± 0.29 |
| Tumor/Large Intestine | 0.31 ± 0.08 | 26.88 ± 12.11 | 15.48 ± 5.25 | 12.39 ± 7.14 |
| Tumor/Kidney | 3.14 ± 0.41 | 1.83 ± 0.27 | 2.27 ± 0.37 | 2.01 ± 0.29 |
| Tumor/Muscle | 18.42 ± 3.71 | 14.92 ± 2.85 | 20.34 ± 10.25 | 18.41 ± 3.47 |

Table 20 shows a comparison of salient tumor-to-tissue activity concentration ratios at 4 h post-injection created using the different pretargeted PET imaging strategies discussed (see Tables 11, 14, 16, and 18).

TABLE 20

| Radioligand Accumulation | $^{64}$Cu-Tz-NOTA | $^{64}$Cu-Tz-SarAr | | |
|---|---|---|---|---|
| Interval | 24 h | 24 h | 48 h | 120 h |
| Tumor/Blood | 1.57 ± 0.55 | 1.39 ± 0.26 | 2.9 ± 0.92 | 3.37 ± 1.16 |
| Tumor/Liver | 3.23 ± 0.9 | 3.83 ± 0.83 | 4.06 ± 1.27 | 3.06 ± 1.2 |
| Tumor/Large Intestine | 0.43 ± 0.2 | 11.65 ± 2.99 | 12.68 ± 4.87 | 17.82 ± 12.22 |
| Tumor/Kidney | 4.32 ± 1.56 | 2.00 ± 0.53 | 2.81 ± 1.16 | 1.69 ± 0.39 |
| Tumor/Muscle | 29.38 ± 8.5 | 14.84 ± 3.69 | 21.84 ± 9.2 | 32.58 ± 16.17 |

Table 21 shows a comparison of salient tumor-to-tissue activity concentration ratios at 12 h post-injection created using the different pretargeted PET imaging strategies discussed (see Tables 11, 14, 16, and 18).

TABLE 21

| Radioligand Accumulation | $^{64}$Cu-Tz-NOTA | $^{64}$Cu-Tz-SarAr | | |
|---|---|---|---|---|
| Interval | 24 h | 24 h | 48 h | 120 h |
| Tumor/Blood | 1.82 ± 0.48 | 3.07 ± 0.79 | 2.72 ± 1.03 | 7.46 ± 2.54 |
| Tumor/Liver | 4.53 ± 1.45 | 5.06 ± 2.23 | 4.58 ± 1.69 | 3.43 ± 0.52 |
| Tumor/Large Intestine | 1.44 ± 0.72 | 33.67 ± 8.82 | 22.66 ± 10.19 | 35.43 ± 12.17 |
| Tumor/Kidney | 4.6 ± 1.71 | 3.61 ± 1.05 | 2.42 ± 0.7 | 1.56 ± 0.21 |

TABLE 21-continued

| Radioligand Accumulation | $^{64}$Cu-Tz-NOTA | $^{64}$Cu-Tz-SarAr | | |
|---|---|---|---|---|
| Interval | 24 h | 24 h | 48 h | 120 h |
| Tumor/Muscle | 26.63 ± 6.59 | 45.12 ± 8.55 | 33.88 ± 9.31 | 38.74 ± 20.11 |

Table 22 shows a comparison of salient tumor-to-tissue activity concentration ratios at 24 h post-injection created using the different pretargeted PET imaging strategies discussed (see Tables 11, 14, 16, and 18).

TABLE 22

| Radioligand Accumulation | $^{64}$Cu-Tz-NOTA | $^{64}$Cu-Tz-SarAr | | |
|---|---|---|---|---|
| Interval | 24 h | 24 h | 48 h | 120 h |
| Tumor/Blood | 1.9 ± 0.63 | 2.83 ± 0.81 | 5.27 ± 1.92 | 5.74 ± 2.17 |
| Tumor/Liver | 3.69 ± 1.01 | 4.87 ± 1.48 | 3.8 ± 1.11 | 4.09 ± 1.13 |
| Tumor/Large Intestine | 2.36 ± 1.37 | 28.86 ± 10.28 | 29.58 ± 6.11 | 26.48 ± 8.29 |
| Tumor/Kidney | 5.61 ± 1.98 | 3.68 ± 1.1 | 3.31 ± 1.07 | 2.29 ± 0.56 |
| Tumor/Muscle | 26.98 ± 7.41 | 37.37 ± 16.06 | 44.18 ± 17.61 | 30.39 ± 11.94 |

Figure 18A:
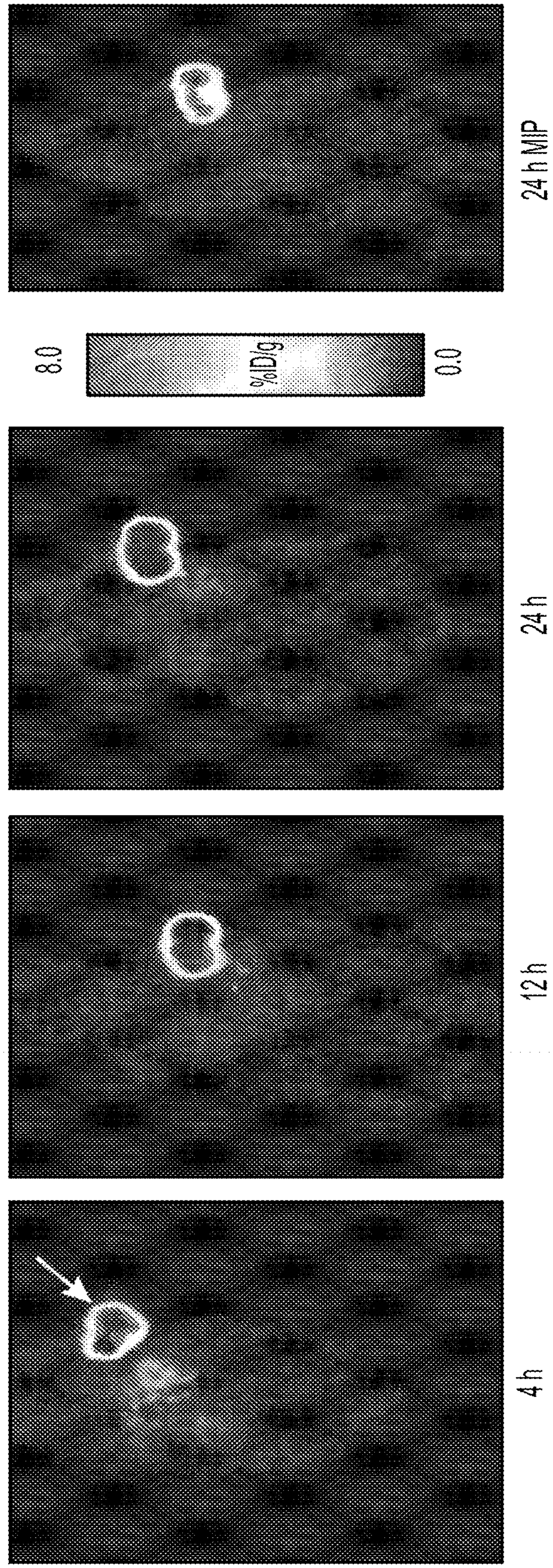
FIGS. 18A and 18B show pretargeted PET imaging using $^{64}$Cu-Tz-SarAr and 48 h (18A) and 120 h (18B) accumulation intervals. The coronal slices (left) intersect the center of the tumor (white arrow). Maximum intensity projections (MIP) collected at 24 h post-injection are also displayed (right).
Figure 18B:
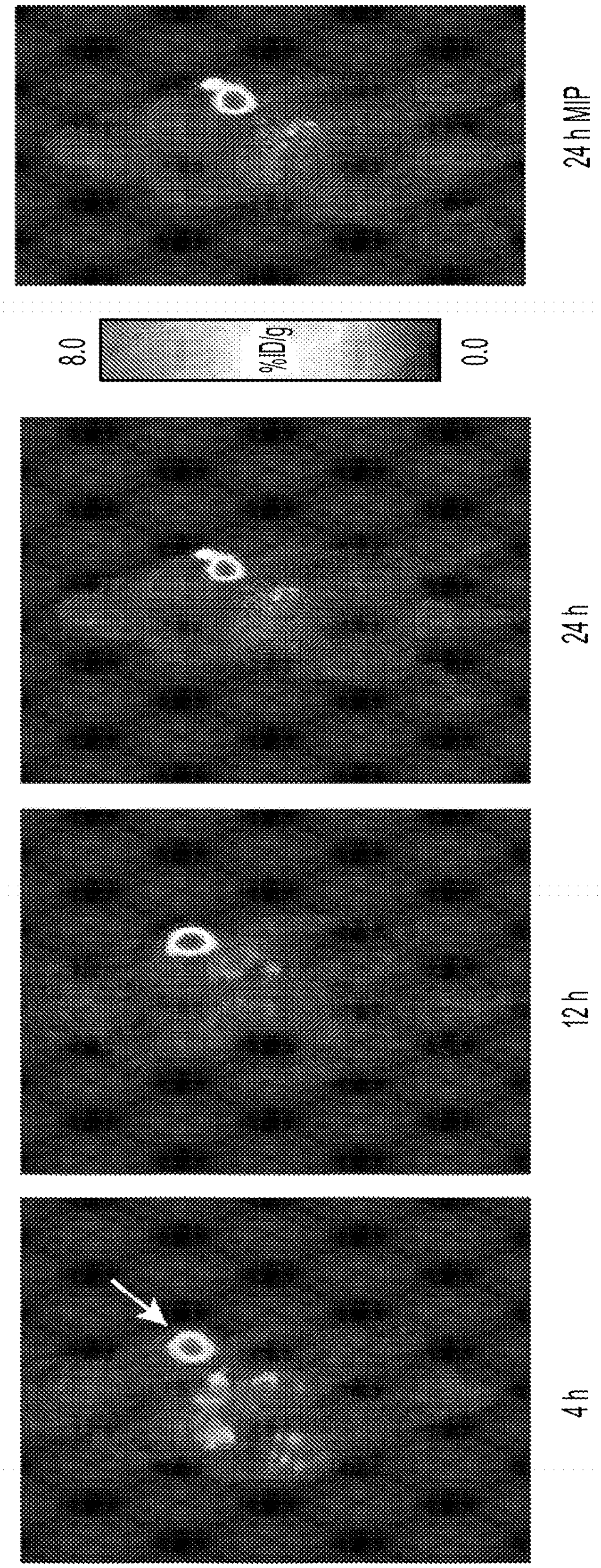
Figure 18C:
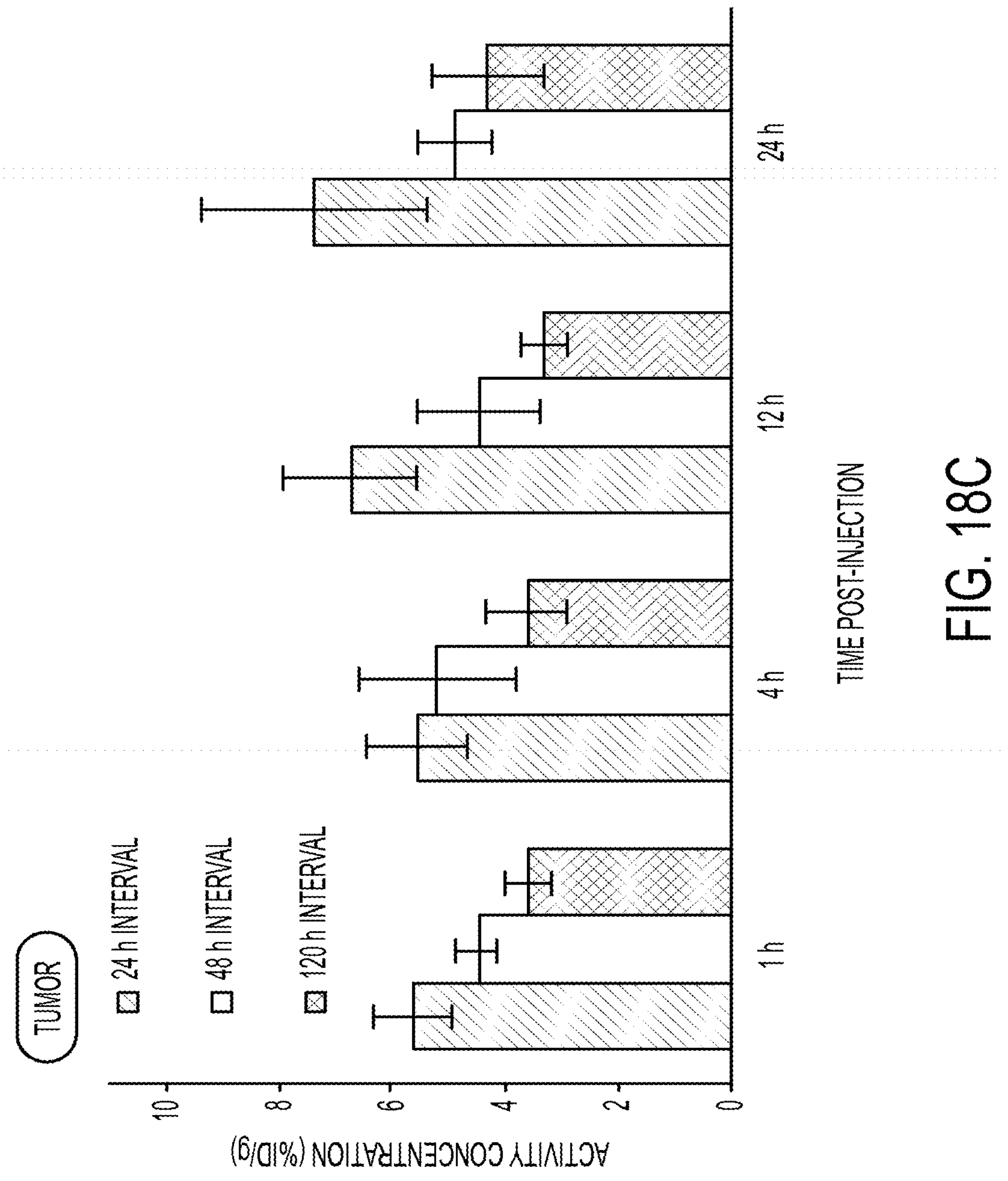
FIG. 18C shows activity concentration in the tumor as a function of both time post-injection and accumulation interval for pretargeting with $^{64}$Cu-Tz-SarAr.
Figure 18D:
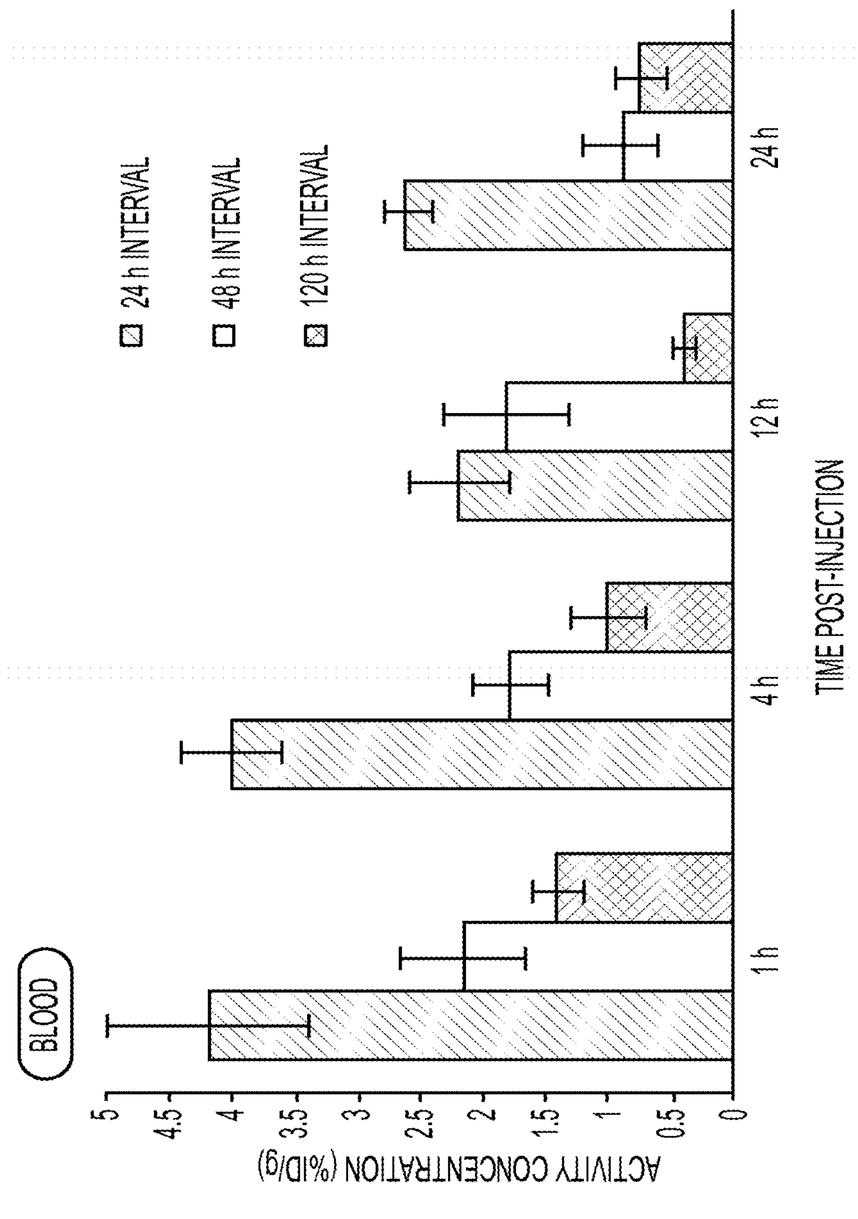
FIG. 18D shows activity concentration in the blood as a function of both time post-injection and accumulation interval for pretargeting with $^{64}$Cu-Tz-SarAr.
Figure 18E:
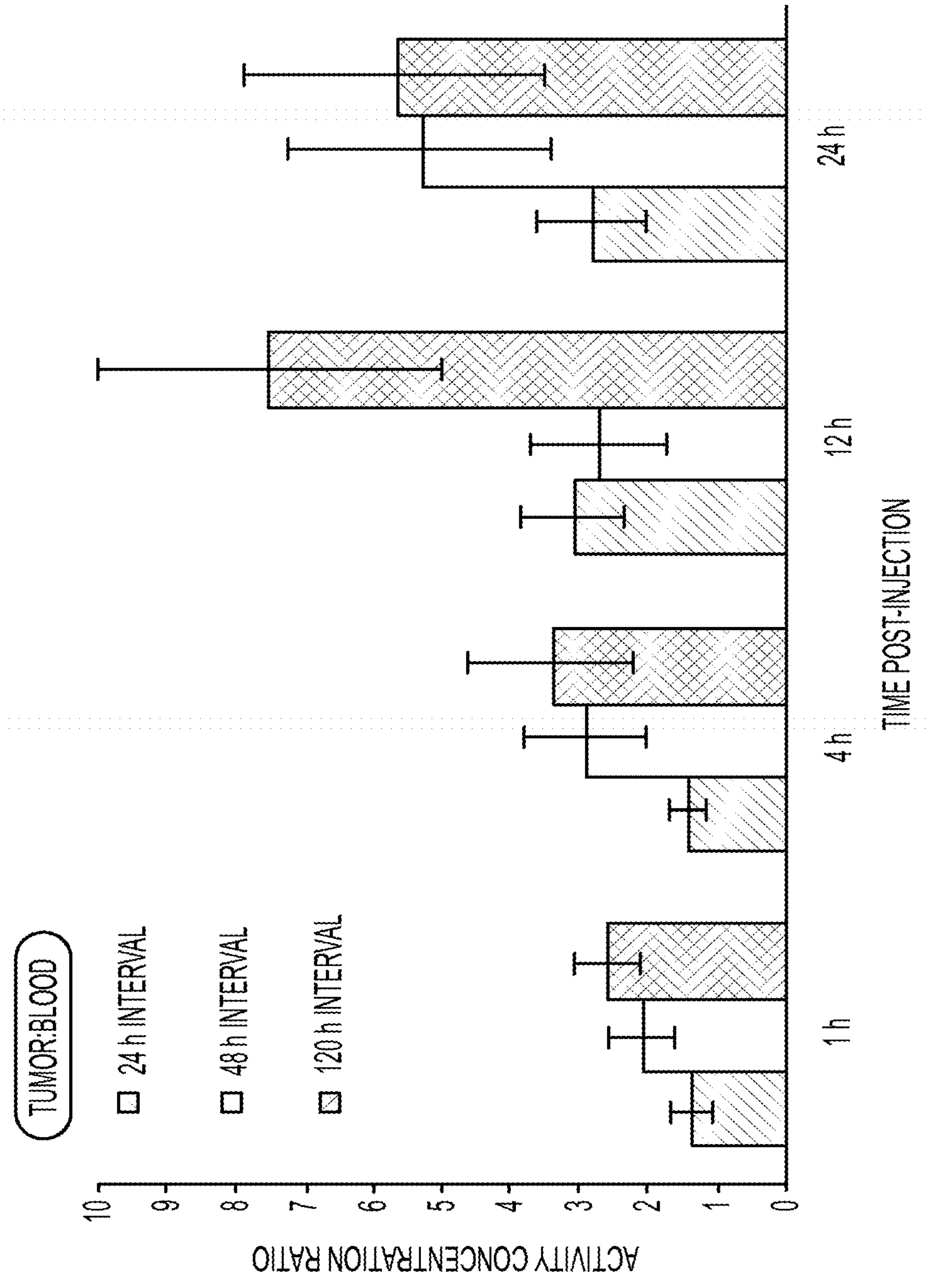
FIG. 18E shows tumor-to-blood activity concentration ratios as a function of both time post-injection and accumulation interval for pretargeting with $^{64}$Cu-Tz-SarAr.
Figure 18F:
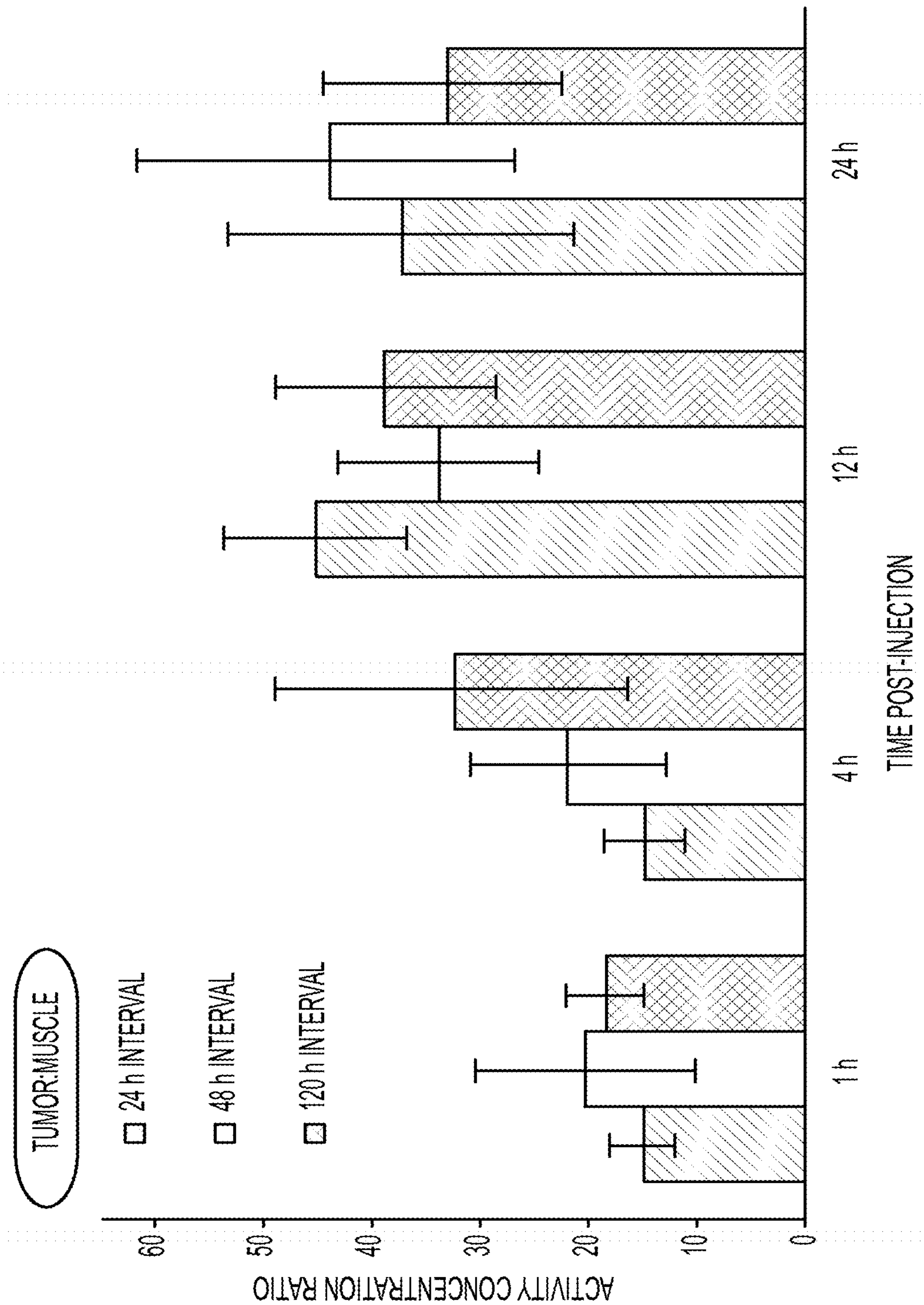
FIG. 18F shows tumor-to-muscle activity concentration ratios as a function of both time post-injection and accumulation interval for pretargeting with $^{64}$Cu-Tz-SarAr.
Figure 19:
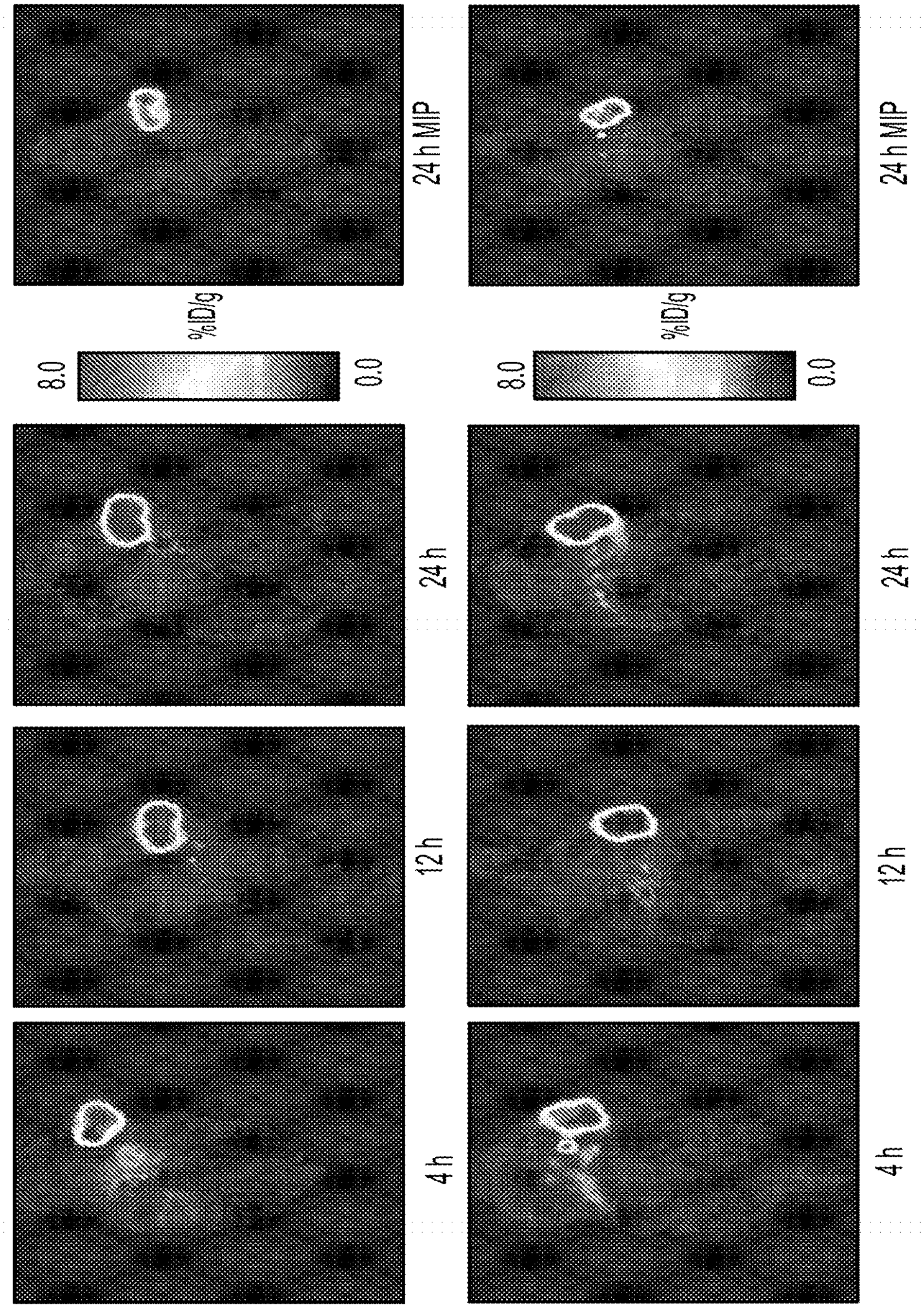
FIG. 19 shows pretargeted PET imaging using $^{64}$Cu-Tz-SarAr and a 48 h accumulation interval. Female athymic nude mice (n=5 per radioligand) bearing subcutaneous SW1222 (right shoulder) xenografts (100-150 mm$^3$, 18-21 days post-inoculation) were administered 100 mg (0.66 nmol) huA33-TCO (in 200 mL 0.9% sterile saline) via intravenous tail vein injection. After an accumulation interval of 48 h, the same mice were then administered $^{64}$Cu-Tz-SarAr (400-450 μCi in 200 mL 0.9% sterile saline), also via intravenous tail vein injection (t=0). The specific activity of $^{64}$Cu-Tz-SarAr was adjusted using cold $^{nat}$Cu-Tz-SarAr such that the molar ratio of $Tz_{injected}$:$huA33_{injected}$=1:1. Static scans were recorded at various time points after injection with a minimum of 30 million coincident events (10-30 min total scan time). Activity concentrations (percentage of dose per gram of tissue [% ID/g]) and maximum intensity projections were determined by conversion of the counting rates from the reconstructed images. All of the resulting PET images were analyzed using ASIPro VM™ software. The coronal slices intersect the center of the tumor, and the maximum intensity projection (MIP) displayed was collected at 24 h post-injection.
Figure 20:
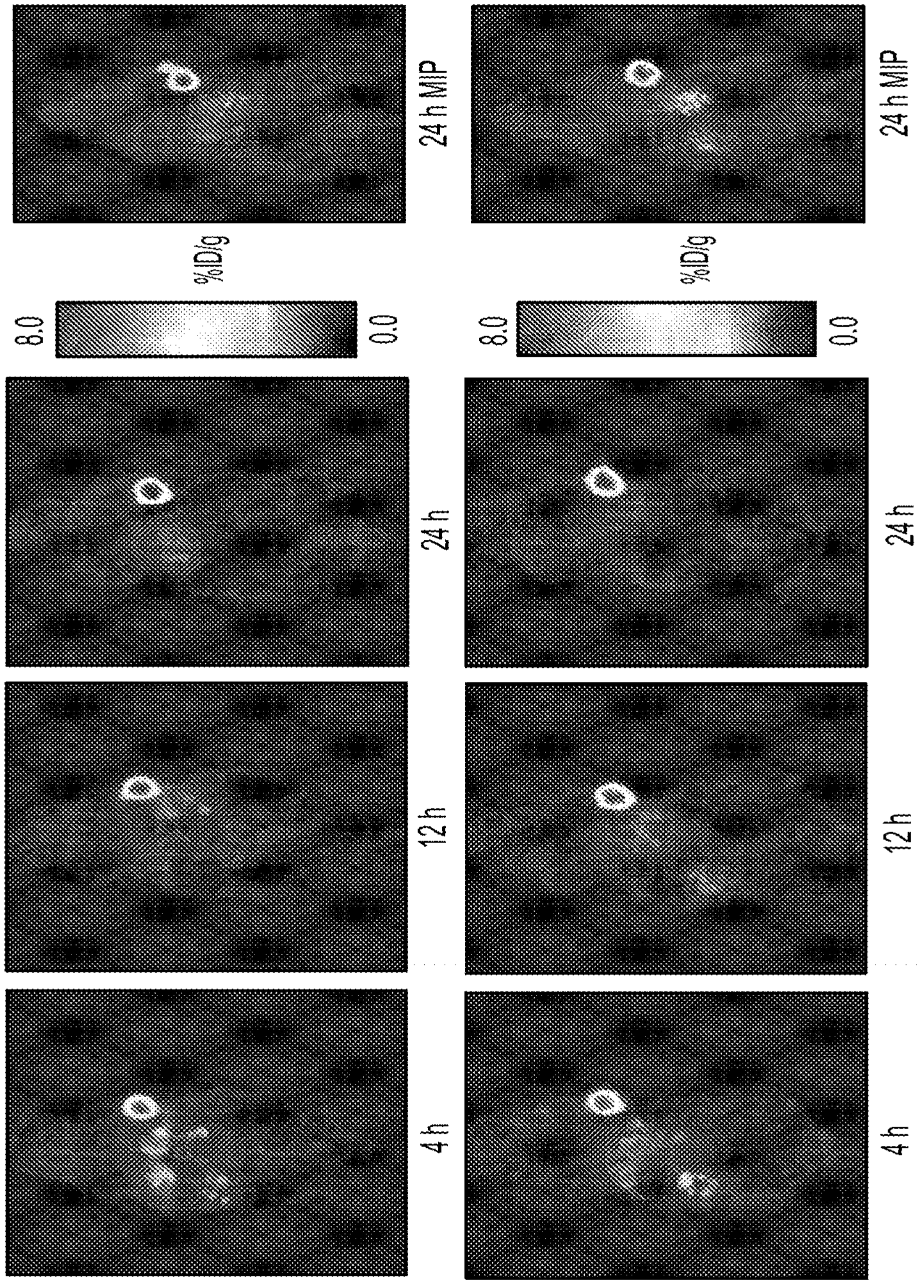
FIG. 20 shows pretargeted PET imaging using $^{64}$Cu-Tz-SarAr and a 120 h accumulation interval. Female athymic nude mice (n=5) bearing subcutaneous SW1222 (right shoulder) xenografts (100-150 mm$^3$, 18-21 days post-inoculation) were administered 100 mg (0.66 nmol) huA33-TCO (in 200 mL 0.9% sterile saline) via intravenous tail vein injection. After an accumulation interval of 120 h, the same mice were then administered $^{64}$Cu-Tz-SarAr (400-450 μCi in 200 mL 0.9% sterile saline), also via intravenous tail vein injection (t=0). The specific activity of $^{64}$Cu-Tz-SarAr was adjusted using cold $^{cat}$Cu-Tz-SarAr such that the molar ratio of $Tz_{injected}$:$huA33_{injected}$=1:1. Static scans were recorded at various time points after injection with a minimum of 30 million coincident events (10-30 min total scan time). Activity concentrations (percentage of dose per gram of tissue [% ID/g]) and maximum intensity projections were determined by conversion of the counting rates from the reconstructed images. All of the resulting PET images were analyzed using ASIPro VM™ software. The coronal slices intersect the center of the tumor, and the maximum intensity projection (MIP) displayed was collected at 24 h post-injection.
Figure 21:
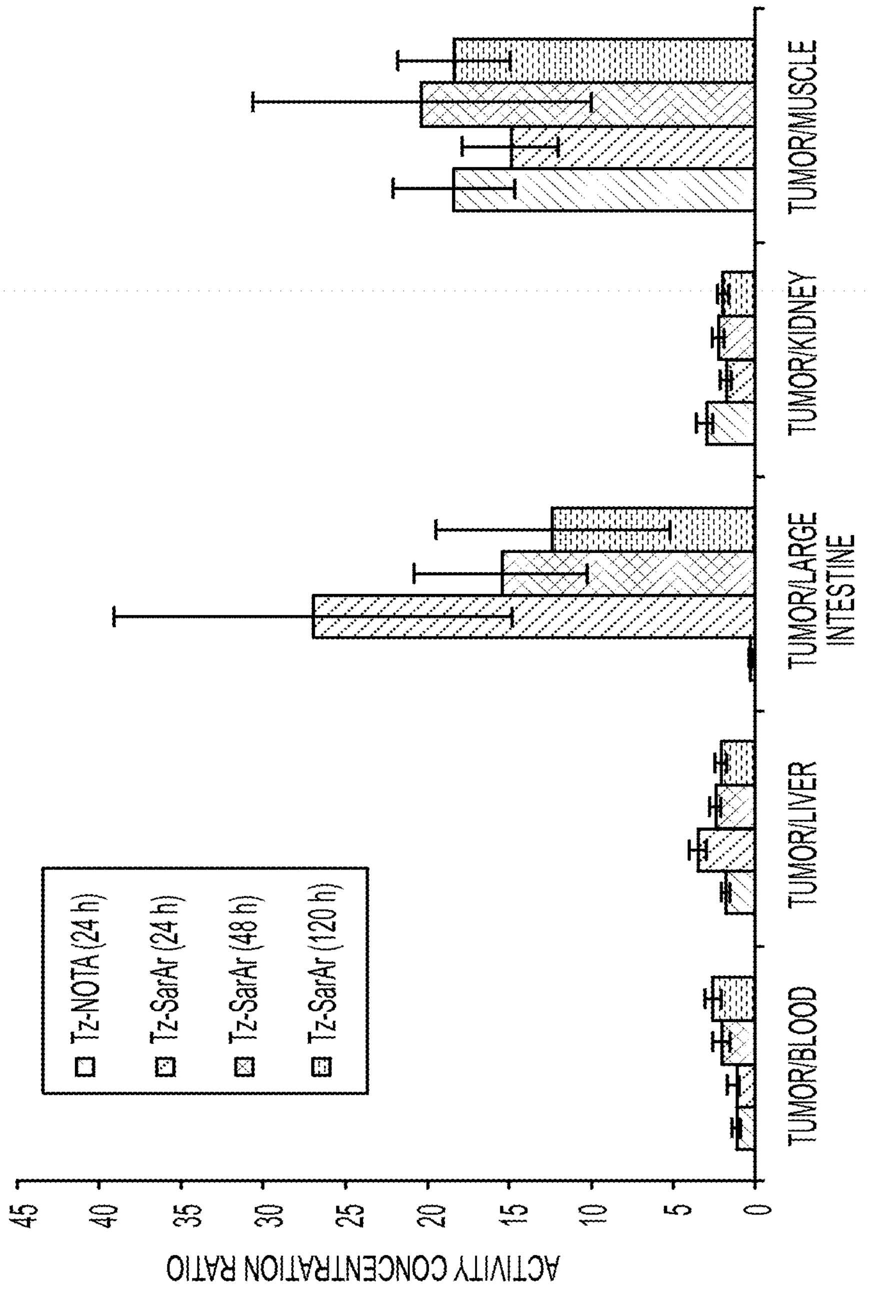
FIG. 21 shows graphical comparison of salient tumor-to-tissue activity concentration ratios at 1 h post-injection created using the different pretargeted PET imaging strategies discussed (see Tables 11, 14, 16, 18, and 19).
Figure 22:
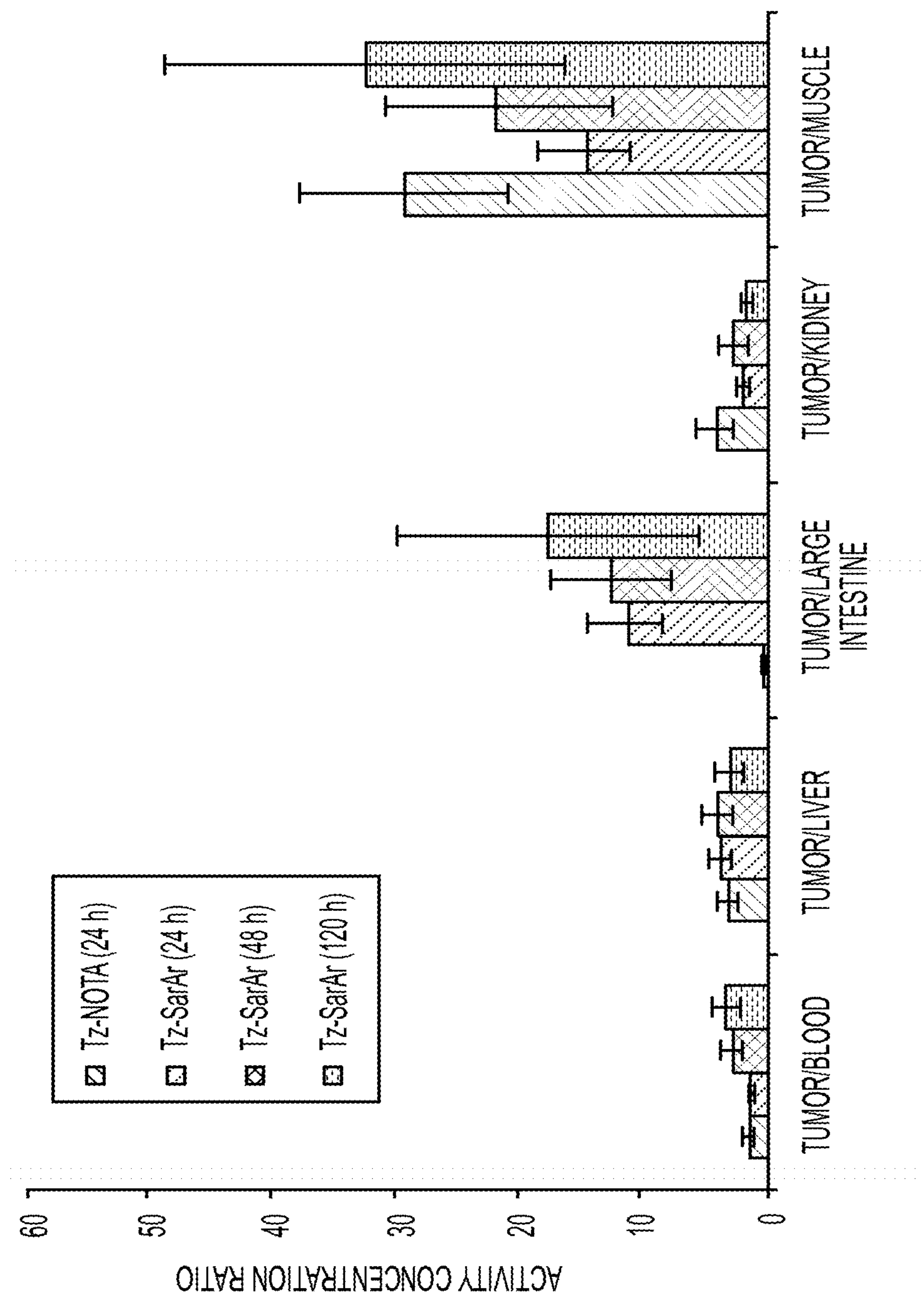
FIG. 22 shows graphical comparison of salient tumor-to-tissue activity concentration ratios at 4 h post-injection created using the different pretargeted PET imaging strategies discussed (see Tables 11, 14, 16, 18, and 20).
Figure 23:
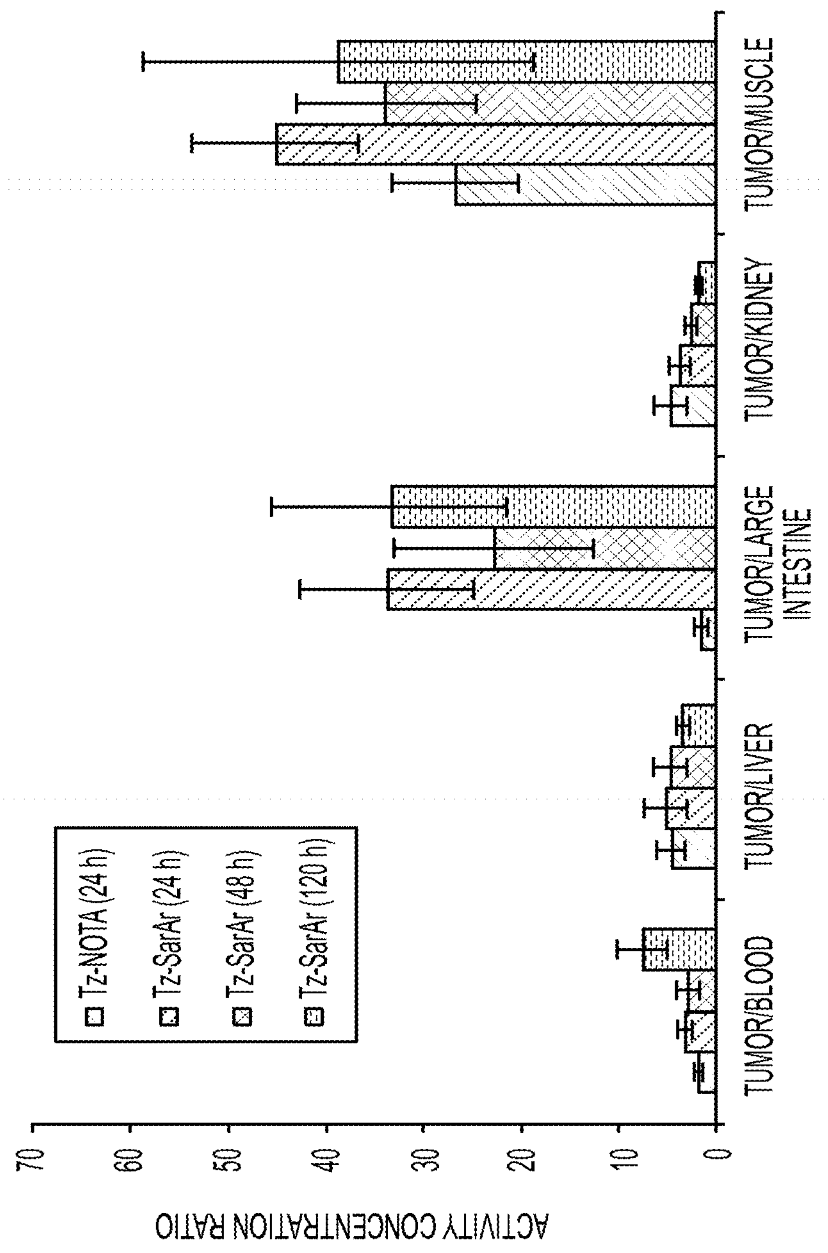
FIG. 23 shows graphical comparison of salient tumor-to-tissue activity concentration ratios at 12 h post-injection created using the different pretargeted PET imaging strategies discussed (see Tables 11, 14, 16, 18, and 21).
Figure 24:
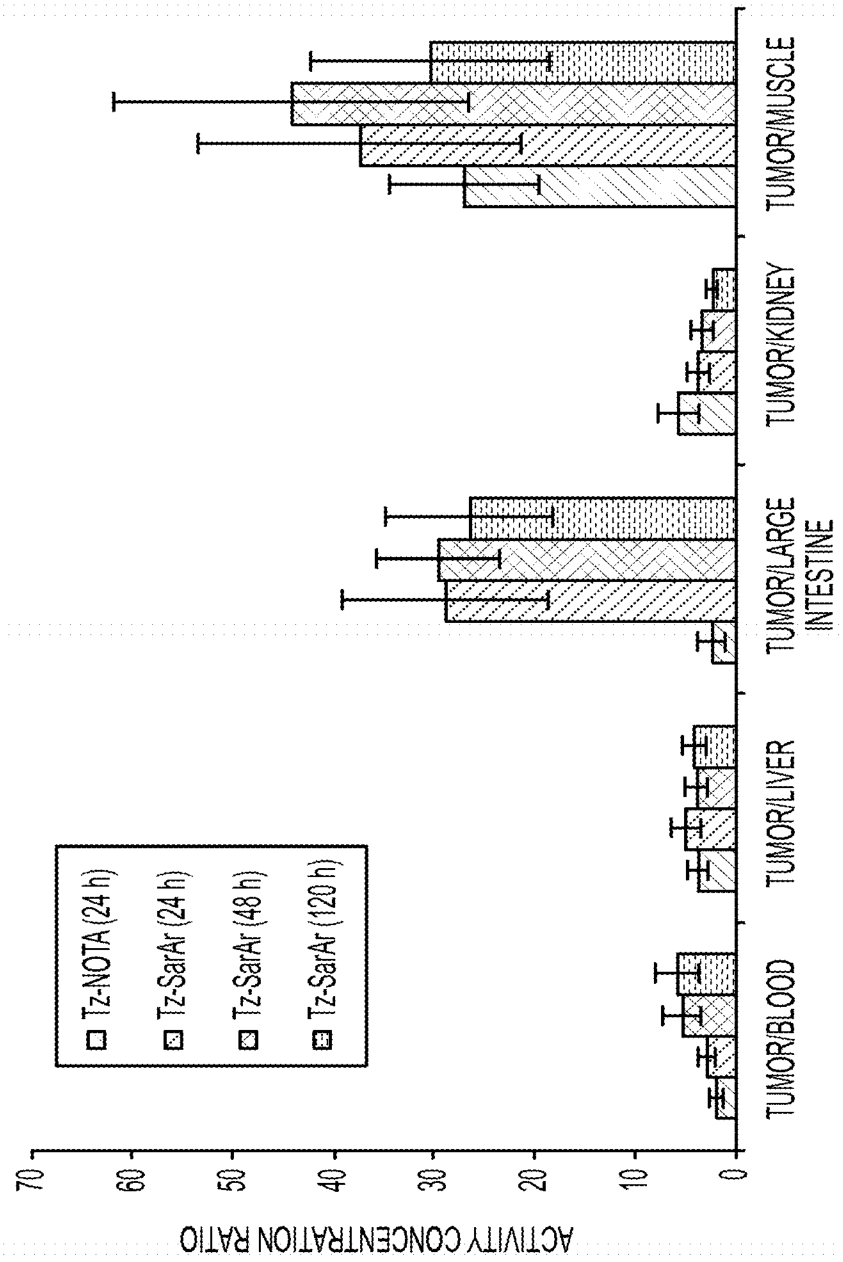
FIG. 24 shows graphical comparison of salient tumor-to-tissue activity concentration ratios at 24 h post-injection created using the different pretargeted PET imaging strategies discussed (see Tables 11, 14, 16, 18, and 22).
Figure 25A:
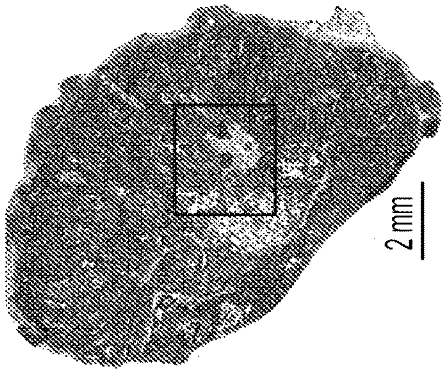
FIGS. 25A-25H show autoradiography, histology, and fluorescence microscopy of SW1222 colorectal carcinoma xenografts resected after pretargeted PET imaging using $^{64}$Cu-Tz-SarAr and an accumulation interval of 120 h.
Figure 25B:
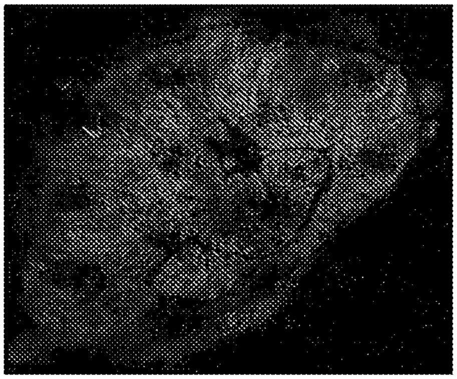
Figure 25C:
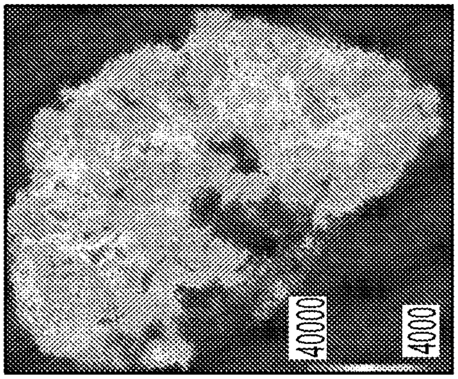
Figure 25D:
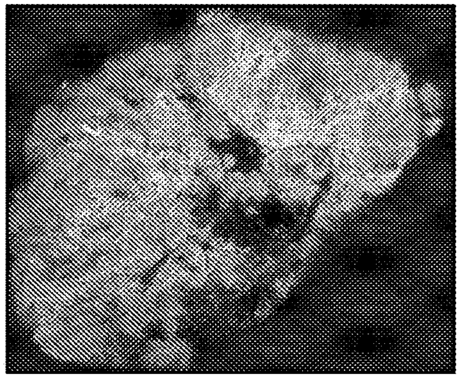
Figure 25E:
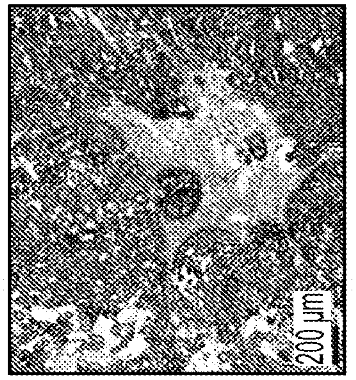
Figure 25F:
Figure 25G:
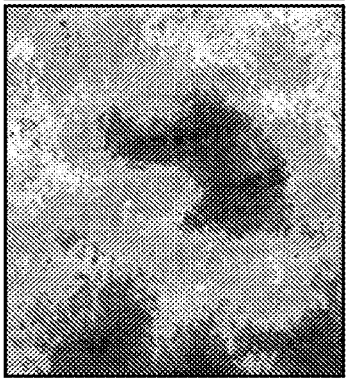
Figure 25H:

Two trends were observed. First, the activity concentrations in the tumor were decreased using longer intervals. For example, the activity concentrations decreased from 5.6±0.9% ID/g at 4 h post-injection using a 24 h interval to 5.2±1.4% ID/g and 3.6±0.7% ID/g at the same time-point using 48 and 120 h intervals, respectively (FIG. 18C). It is thought that this is because the TCO moiety is not infinitely stable to trans-cis isomerization (and thus inactivation) in vivo. However, in both cases the amount of uptake in the tumor at 1 h post-injection was nearly identical to that at 24 h, suggesting that longer accumulation intervals effectively eliminated click ligations in the blood. Second, the activity concentrations in the blood and most other tissues were reduced (FIG. 18D). The activity concentration remaining in the blood at 4 h post-injection with a 24 h accumulation interval was 4.0±0.37% ID/g. Using 48 and 120 h intervals, the corresponding values decreased to 1.78±0.28% ID/g and 1.05±0.29% ID/g respectively. Taken together, these two trends resulted in higher tumor-to-blood activity ratios for the longer accumulation intervals, for example, 2.83±0.81, 5.27±1.92, and 5.74±2.17 at 24 h post-injection for 24, 48, and 120 h intervals, respectively (FIG. 18E). Tumor-to-background activity ratios remained lowed in non-target tissue because activity concentrations were offset by the decreases in the activity concentrations in the tumor (FIG. 18F).

Autoradiography and Immunohistochemistry

Immediately following the pretargeted PET imaging studies, ex vivo autoradiographical and immunohistochemical analyses were performed on the SW1222 xenografts in order to learn more about the microscopic distribution of the huA33-TCO and $^{64}$Cu-Tz-SarAr (FIG. 25). As expected, hematoxylin and eosin staining of the excised tumors revealed that both huA33-TCO and $^{64}$Cu-Tz-SarAr were almost exclusively associated with tumor cells rather than regions of stromal tissue. Moreover, microscopic co-localization of the autoradiographical signal of $^{64}$Cu-Tz-SarAr and the fluorescence staining for huA33-TCO was demonstrated. These observations further supported the selective, in vivo formation of the completed $^{64}$Cu-SarAr huA33 radioimmunoconjugate.

Dosimetry

The radiation dosimetry of $^{64}$Cu-Tz-SarAr was performed to ensure the selective delivery of radioisotopes to malignant tissues at radiation doses below the doses of traditional radioimmunoconjugates. To this end, dosimetry calculations were performed using the biodistribution data collected and the OLINDA computer program to determine the mean organ absorbed doses (rad/mCi) and effective dose (rem/mCi) for each strategy (Table 23). The total effective dose of the $^{64}$Cu-Tz-SarAr pretargeting strategy with a 24 h interval period was 0.041 rem/mCi, a slight reduction compared to the 0.046 rem/mCi effective dose created by $^{64}$Cu-Tz-NOTA. This difference was due to the significant reduction in the mean organ absorbed dose to the large intestine. Moreover, the total effective dose of the $^{64}$Cu-Tz-SarAr pretargeting strategy was inversely proportional to the duration of the accumulation interval. For example, the effective dose decreased from 0.041 rem/mCi with a 24 h interval to 0.038 rem/mCi with a 48 h interval to 0.034 with a 120 h interval.

Table 23 shows dosimetry calculations for various huA33-based PET imaging strategies.

TABLE 23

| | | | Pretargeting | | | |
|---|---|---|---|---|---|---|
| | $^{89}$Zr- | $^{64}$Cu- | $^{64}$Cu-Tz-NOTA* | $^{64}$Cu-Tz-SarAr | | |
| Target Organ† | DFO huA33* | NOTA huA33* | 24 h interval | 24 h interval | 48 h interval | 120 h interval |
| Adrenals | 1.64 | 0.0726 | 0.0251 | 0.0374 | 0.0348 | 0.0322 |
| Brain | 0.764 | 0.0555 | 0.0236 | 0.0361 | 0.0339 | 0.0316 |
| Breasts | 0.621 | 0.0509 | 0.0209 | 0.0323 | 0.0303 | 0.0281 |
| Gallbladder Wall | 1.44 | 0.0741 | 0.0272 | 0.0391 | 0.0368 | 0.0341 |
| Lower Lg. Int. Wall | 1.34 | 0.193 | 0.166 | 0.0482 | 0.0456 | 0.0400 |
| Small Intestine | 1.11 | 0.0832 | 0.033 | 0.0418 | 0.0390 | 0.0362 |
| Stomach Wall | 0.949 | 0.0883 | 0.0267 | 0.0552 | 0.0422 | 0.0394 |
| Upper Lg. Int. Wall | 1.20 | 0.145 | 0.114 | 0.0409 | 0.0382 | 0.0355 |
| Heart Wall | 1.55 | 0.108 | 0.0294 | 0.0427 | 0.0379 | 0.0330 |
| Kidneys | 2.53 | 0.186 | 0.0315 | 0.0661 | 0.0539 | 0.0566 |
| Liver | 2.84 | 0.194 | 0.0311 | 0.0303 | 0.0334 | 0.0301 |
| Lungs | 2.26 | 0.179 | 0.0289 | 0.0325 | 0.0326 | 0.0216 |
| Muscle | 1.27 | 0.0546 | 0.0138 | 0.0193 | 0.0163 | 0.0139 |

TABLE 23-continued

| | | | Pretargeting | | | |
|---|---|---|---|---|---|---|
| | $^{89}$Zr- | $^{64}$Cu- | $^{64}$Cu-Tz-NOTA* | $^{64}$Cu-Tz-SarAr | | |
| Target Organ† | DFO huA33* | NOTA huA33* | 24 h interval | 24 h interval | 48 h interval | 120 h interval |
| Ovaries | 1.09 | 0.0681 | 0.0299 | 0.0401 | 0.0374 | 0.0346 |
| Pancreas | 1.37 | 0.0708 | 0.0258 | 0.0395 | 0.0364 | 0.0338 |
| Red Marrow | 3.12 | 0.308 | 0.0530 | 0.0301 | 0.0280 | 0.0258 |
| Osteogenic Cells | 6.09 | 0.439 | 0.0852 | 0.0893 | 0.0805 | 0.0720 |
| Skin | 0.677 | 0.0464 | 0.0194 | 0.0297 | 0.0277 | 0.0258 |
| Spleen | 2.52 | 0.120 | 0.0180 | 0.0370 | 0.0205 | 0.0225 |
| Testes | 0.683 | 0.0522 | 0.0225 | 0.0345 | 0.0322 | 0.0299 |
| Thymus | 0.988 | 0.0584 | 0.0227 | 0.0349 | 0.0325 | 0.0299 |
| Thyroid | 0.947 | 0.0563 | 0.0228 | 0.0351 | 0.0328 | 0.0303 |
| Bladder Wall | 0.826 | 0.0609 | 0.0262 | 0.0391 | 0.0365 | 0.0338 |
| Uterus | 0.941 | 0.0652 | 0.0277 | 0.0410 | 0.0383 | 0.0355 |
| Total Body | 1.39 | 0.0855 | 0.0272 | 0.0379 | 0.0348 | 0.0316 |
| Effective Dose | 1.54 | 0.133 | 0.046 | 0.0414 | 0.0377 | 0.0341 |

†Mean organ absorbed doses and effective dose are expressed in rad/mCi and rem/mCi, respectively.
*Data originally reported in Zeglis, B.M. et al. Journal of Nuclear Medicine. 54, 1389-1396 (2013). ©2013 by the Society of Nuclear Medicine and Molecular Imaging, Inc.

Next, the dosimetry of the $^{64}$Cu-Tz-SarAr pretargeting strategy and directly labeled antibodies was compared. Using a 120 h accumulation interval, the $^{64}$Cu-Tz-SarAr pretargeting approach yielded an effective dose of 0.034 rem/mCi, a nearly four-fold reduction compared to the 0.133 rem/mCi effective dose delivered by huA33 labeled directly with $^{64}$Cu. Moreover, the effective doses of $^{64}$Cu-Tz-SarAr to huA33 directly labeled with $^{89}$Zr was compared. In this case, the effective dose of $^{89}$Zr-DFO huA33 was 1.54 rem/mCi, or almost 50 times greater than the 0.034 rem/mCi dose associated with $^{64}$Cu-Tz-SarAr pretargeting with a 120 h accumulation interval. In some tissues, this dose rate reduction was more pronounced. For example, the mean absorbed doses to osteogenic cells and red marrow with $^{89}$Zr-DFO huA33 was 6.09 rad/mCi and 3.12 rad/mCi, respectively, approximately 80 and 120 times higher than the dose delivered to the same tissues by the $^{64}$Cu-Tz-SarAr pretargeting approach.

Experimental Examples of $^{64}$Cu tetrazine radioligands

Methods and Materials

Unless otherwise noted, all chemicals were acquired from Sigma-Aldrich (St. Louis, MO) and were used as received without further purification. All water employed was ultra-pure (greater than 18.2 $M^{-1}$ $cm^{-1}$ at 25° C.), all DMSO was of molecular biology grade (greater than 99.9%), and all other solvents were of the highest grade commercially available. Acetonitrile (CH3CN) and dimethylformamide (DMF) were purchased from Acros Organics (Waltham, MA) as extra dry over molecular sieves. Amine-reactive trans-cyclooctene [(E)-cyclooct-4-enyl 2,5-dioxo-1-pyrrolidinyl carbonate; TCO-NHS)] and amine-reactive tetrazine (2,6-dioxo-1-pyrrolidinyl 5-[4-(1,2,4,5-tetrazin-3-yl)benzylamino]-5-oxopentanoate; Tz-NHS) were purchased from Sigma-Aldrich (St. Louis, MO). p-NCS-Bn-NOTA, p-NH2-Bn-NOTA, and DiAmSar chelators were purchased from Macrocyclics, Inc. (Dallas, TX). Tz-NOTA and 64Cu-Tz-NOTA were synthesized as previously reported. 44 Humanized A33 (huA33) antibody was generously provided by the Ludwig Institute for Cancer Research (New York, NY) and stored at −80° C. prior to use. $^{64}$Cu was purchased from Washington University, St. Louis, where it was produced on a medical cyclotron (Model CS-15, Cyclotron Corp.) via the $^{64}$Ni(p,n)$^{64}$Cu transformation and purified as previously described to yield [$^{64}$Cu]$CuCl_2$ with an effective specific activity of 200-400 mCi/μg. 45 Human colorectal cancer cell line SW1222 was obtained from the Ludwig Institute for Cancer Immunotherapy and grown by serial passage. Amine-reactive AlexaFluor® 680 (AF680-NHS) was purchased from ThermoFisher Scientific (Waltham, MA).

Synthesis of tert-butyl (1-(4-(1,2,4,5-tetrazin-3-yl) phenyl)-3,7-dioxo-11,14,17,20,23,26,29 heptaoxa-2, 8-diazahentriacontan-31-yl)carbamate (Tz-PEG7-NHBoc)

Tz-NHS (10 mg; 0.025 mmol; 398.4 g/mol) was dissolved in 400 μL DMSO and added to 15 mg O-(2-aminoethyl)-O'-[2-(bocamino)ethyl]hexaethylene glycol (0.032 mmol; 1.3 equiv.; 468.6 g/mol). 10 μL triethylamine (7.3 mg; 0.072 mmol; 101.2 g/mol) was then added to this solution, and the solution was placed on an agitating thermomixer at 300 rpm for 30 minutes at room temperature. After 30 minutes, the reaction was purified via preparative C18 HPLC using a gradient of 5:95 MeCN:H2O (both with 0.1% TFA) to 95:5 MeCN:H2O over 30 min (tR=18.2 min). Lyophilization of the HPLC eluent yielded the purified product as a 16 mg of a bright pink powder (MW=751.9 g/mol; 0.021 mmol; 85% yield). 1H NMR (500 MHz, DMSO), δ, ppm: 10.52 (s, 1H), 8.50 (m, 3H), 7.82 (t, 1H), 7.46 (d, 2H), 6.69 (t, 1H), 4.33 (d, 2H), 3.42 (m, 22H), 3.33 (t, 2H), 3.31 (t, 2H), 3.12 (q, 2H), 2.99 (q, 2H), 2.12 (t, 2H), 2.03 (t, 2H), 2.12 (t, 2H), 1.70 (q, 2H), 1.29 (s, 9H). ESI-MS(+): m/z (%)=753.1 [M+H]+ HRMS (ESI): m/z calcd. for C35H57N7O11Na: 774.4005; found: 774.4014. UV-Vis: $\varepsilon_{525}$=530 $M^{-1}$ $cm^{-1}$.

Synthesis of N$^1$-(4-(1,2,4,5-tetrazin-3-yl)benzyl)-N$^5$-(23-amino-3,6,9,12,15,18,21 heptaoxatricosyl) glutaramide (Tz-$PEG_7$-$NH_2$)

Tz-$PEG_7$-NHBoc (10 mg; 0.014 mmol; 717.5 g/mol) was dissolved in 400 μL of 1:1 $CH_2Cl_2$:TFA and placed on an agitating thermomixer at 300 rpm for 30 minutes at room temperature. After 30 minutes, the solvent was removed via rotary evaporation, the residue was taken back up in $H_2O$, and the reaction was purified via preparative Cis HPLC using a gradient of 5:95 MeCN:$H_2O$ (both with 0.1% TFA) to 95:5 MeCN:$H_2O$ over 30 min ($t_R$=12.5 min). Lyophilization of the HPLC eluent yielded the purified product as 9 mg of a bright pink powder (MW=651.7; 0.013 mmol; 95% yield). $^1$H NMR (500 MHz, DMSO), δ, ppm: 10.58 (s, 1H), 8.46 (m, 2H), 7.87 (t, 1H), 7.75 (d, 2H), 7.52 (d, 1H), 4.40 (d, 2H), 3.60-3.50 (m, 26H), 3.40 (t, 2H), 3.32 (bs, 2H), 3.20 (q, 2H), 2.99 (bs, 2H), 2.19 (t, 2H), 2.12 (t, 2H), 1.79 (q, 2H). ESI-MS(+): m/z (%)=652.9 [M+H]$^+$ HRMS (ESI): m/z calcd. for $C_{30}H_{50}N_7O_9$: 652.3670; found: 652.3676. UV-Vis: $\varepsilon_{525}$=535 $M^{-1}$ $cm^{-1}$.

Synthesis of 2,2',2"-(2-(4-(3-(1-(4-(1,2,4,5-tetrazin-3-yl)phenyl)-3,7-dioxo-11,14,17,20,23,26,29 heptaoxa-2,8-diazahentriacontan-31-yl)thioureido)benzyl)-1,4,7-triazonane-1,4,7-triyl)triacetic acid (Tz-PEG$_7$-NOTA)

Tz-PEG$_7$-NH$_2$ (5 mg; 0.008 mmol; 651.8 g/mol) was dissolved in 400 μL DMSO and added to 10 mg p-NCS-Bn-NOTA (0.022 mmol; 2.75 equiv.; 450.5 g/mol). 10 μL triethylamine (7.3 mg; 0.072 mmol; 101.2 g/mol) was then added to this solution, and the solution was placed on an agitating thermomixer at 300 rpm for 30 minutes at room temperature. After 30 minutes, the reaction was purified via preparative Cis HPLC using a gradient of 5:95 MeCN:H$_2$O (both with 0.1% TFA) to 95:5 MeCN:H$_2$O over 30 min ($t_R$=15.5 min). Lyophilization of the HPLC eluent yielded the purified product as 6 mg of a bright pink powder (MW=1102.2; 0.005 mmol; 68% yield). $^1$H NMR (500 MHz, DMSO), δ, ppm: 10.51 (s, 1H), 9.50 (bs, 1H), 8.40 (m, 3H), 7.79 (m, 1H), 7.62 (m, 1H), 7.47 (d, 2H), 7.35 (d, 2H), 7.03 (d, 2H), 4.43 (d, 2H), 4.00-3.20 (m, 50H), 3.12 (q, 2H), 2.96 (bs, 2H), 2.11 (t, 2H), 2.03 (t, 2H), 1.70 (q, 2H). ESI-MS(−): m/z (%)=1100.6 [M−H]$^-$; 549.9 [M−2H]$^{2-}$ HRMS (ESI): m/z calcd. for $C_{50}H_{76}N_{11}O_{15}S$: 1102.5243; found: 1102.5253. UV-Vis: $\varepsilon_{525}$=540 $M^{-1}$ $cm^{-1}$.

Synthesis of N$^1$-(4-(((pivaloyloxy)amino)methyl) benzyl)-3,6,10,13,16,19 exaazabicyclo[6.6.6] icosane-1,8-diamine (SarAr-Bn-NHBoc)

N-Boc-4-(bromomethyl)-benzylamine (0.037 g; 0.12 mmol; 1.3 equiv.; 300.2 g/mol) was added to a stirred solution of DiAmSar (0.030 g; 0.094 mmol; 1.0 equiv.; 314.5 g/mol) in anhydrous dimethylformamide (4.0 mL) at room temperature. Sodium carbonate (0.034 g; 0.32 mmol; 3.5 equiv.; 105.9 g/mol) was added, and the reaction solution was stirred at 70° C. for 16 h. The reaction was diluted with water (6.0 mL), and purification by HPLC (3.0 mL/min, 5% to 80% CH$_3$CN in 15 min) afforded SarAr-Bn-NHBoc (MW=533.8; 0.035 g; 70%) as a colorless solid: $t_R$=9.4 min. $^1$H NMR (500 MHz, DMSO), δ, ppm: 7.38-7.50 (m, 4H), 4.18 (m, 2H), 2.31-3.98 (m, 42H), 1.35 (s, 9H). ESI-MS(+): m/z=534.5 [M+H]$^+$. HRMS (ESI): m/z calcd. for $C_{27}H_{52}N_9O_2$: 534.4244; found: 534.4250.

Synthesis of N$^1$-(4-(aminomethyl)benzyl)-3,6,10,13, 16,19 hexaazabicyclo[6.6.6]icosane-1,8-diamine (SarAr-Bn-NH$_2$)

Trifluoroacetic acid (2.0 mL) was added slowly to a stirred solution of SarAr-Bn-NHBoc (0.031 g; 0.058 mmol; 1.0 equiv.; 533.4 g/mol) in dry acetonitrile (2.0 mL), and the reaction mixture was stirred at room temperature for 90 min. Evaporation of the solvents under reduced pressure and purification by HPLC (6.0 mL/min, 5% to 60% CH$_3$CN in 20 min) afforded SarAr-Bn-NH$_2$ (MW=434.7; 0.026 g, 99%) as a colorless solid: $t_R$=6.8 min. $^1$H NMR (500 MHz, DMSO), δ, ppm: 7.55 (d, 2H), 7.51 (d, 2H), 4.23 (s, 2H), 2.56-4.05 (m, 27H). ESI-MS(+): m/z=434.4 [M+H]$^+$. HRMS (ESI): m/z calcd. for $C_{22}H_{44}N_9$: 434.3720; found: 434.3715.

Synthesis of N$^1$-(4-(1,2,4,5-tetrazin-3-yl)benzyl)-N$^5$-(4-(((8-amino-3,6,10,13,16,19 hexaazabicyclo [6.6.6]icosan-1-yl)amino)methyl)benzyl)glutaramide (Tz-SarAr)

A solution of Tz-NHS (5.0 mg; 0.013 mmol; 1.0 equiv.; 398.4 g/mol) in anhydrous dimethylformamide (400 μL) was added to a stirred solution of SarAr-Bn-NH$_2$ (5.4 mg; 0.013 mmol; 1.0 equiv.; 434.7 g/mol) in anhydrous dimethylformamide (200 μL) at room temperature, and the reaction solution was stirred in the dark for 2 h at room temperature. After dilution with water (1.8 mL), purification by HPLC (1.0 mL/min, 5% to 80% CH$_3$CN in 15 min) afforded Tz-SarAr (MW=716.9; 3.9 mg; 42%) as a pink solid: $t_R$=9.5 min. $^1$H NMR (600 MHz, D$_2$O), δ, ppm: 10.25 (s, 1H), 8.31 (d, 2H), 7.46 (d, 2H), 7.22-7.27 (m, 4H), 4.39 (m, 2H), 4.24 (m, 3H), 2.46-3.95 (m, 24H), 2.41-2.44 (m, 4H), 1.83 (m, 2H). ESI-MS(+): m/z=717.6 [M+H]$^+$. HRMS (ESI): m/z calcd. for $C_{36}H_{57}N_{14}O_2$: 717.4789; found: 717.4788.

Preparation of $^{64}$Cu-Tz-PEG$_7$-NOTA

A solution of Tz-PEG$_7$-NOTA (5-25 μg; 4.5-22.6 nmol) in NH$_4$OAc buffer (0.2 M, pH 5.5, 200 μL) was first prepared. Then, the desired amount of $^{64}$CuCl$_2$ in 0.1 M HCl (1500-7500 μCi) was added to the reaction mixture, and the solution was placed on an agitating thermomixer at 300 rpm for 30 minutes at room temperature. After this incubation, the $^{64}$Cu-Tz-PEG$_7$-NOTA was purified via reverse phase Cis HPLC ($t_R$=9.7 min) to yield the completed radioligand in greater than 99% radionuclidic purity, 78±6% decay-corrected isolated yield, and a specific activity of 278±32 μCi/μg (323±37 mCi/μmol).

Preparation of $^{64}$Cu-Tz-SarAr

A solution of Tz-SarAr (5-25 μg; 6.9-34.9 nmol) in NH$_4$OAc buffer (0.2 M, pH 5.5, 200 μL) was first prepared. Then, the desired amount of $^{64}$CuCl$_2$ in 0.1 M HCl (1500-7500 μCi) was added to the reaction mixture, and the solution was placed on an agitating thermomixer at 300 rpm for 30 minutes at room temperature. After this incubation, the $^{64}$Cu-Tz-PEG$_7$-NOTA was purified via reverse phase Cis HPLC ($t_R$=8.7 min) to yield the completed radioligand in greater than 99% radionuclidic purity, 79±7% decay-corrected isolated yield, and a specific activity of 398±46 μCi/μg (310±36 mCi/μmol) (n=6).

Pretargeted PET Imaging Experiments

All pretargeted PET imaging experiments were performed on an Inveon PET/CT scanner (Siemens Healthcare Global). Female athymic nude mice (n=5 per radioligand) bearing subcutaneous SW1222 (right shoulder) xenografts (100-150 mm$^3$, 9-12 days post-inoculation) were administered 100 μg (0.66 nmol) huA33-TCO (in 200 μL 0.9% sterile saline) via intravenous tail vein injection. After an accumulation interval of 24, 48, or 120 h, the same mice were then administered either $^{64}$Cu-Tz-PEG$_7$-NOTA or $^{64}$Cu-Tz-SarAr (400-450 μCi in 200 μL 0.9% sterile saline), also via intravenous tail vein injection (t=0). For both $^{64}$Cu-Tz-PEG$_7$-NOTA and $^{64}$Cu-Tz-SarAr, the specific activity of the radiotracer was adjusted using cold $^{cat}$Cu-Tz-PEG$_7$-NOTA or $^{cat}$Cu-Tz-SarAr such that the molar ratio of $Tz_{injected}$:$huA33_{injected}$≈1:1. Approximately 5 minutes prior to the PET images, mice were anesthetized by inhalation of 2% isoflurane (Baxter Healthcare, Deerfield, IL)/oxygen gas mixture and placed on the scanner bed; anesthesia was maintained using 1% isoflurane/gas mixture. Static scans were recorded at various time points after injection with a minimum of 30 million coincident events (10-30 min total scan time). An energy window of 350-700 keV and a coincidence timing window of 6 ns were used. Data were sorted into 2-dimensional histograms by Fourier re-binning, and the images were reconstructed using a two-dimensional ordered subset expectation maximization (2DOSEM) algorithm (16 subsets, 4 iterations) into a 128×128×159 (0.78×0.78×0.80 mm) matrix. The image data was normalized to correct for non-uniformity of response of the PET, dead-time count losses, positron branching ratio, and physical decay to the time of injection, but no attenuation, scatter, or partial-volume averaging correction was applied. Activity concentrations (percentage of dose per gram of tissue [% ID/g]) and maximum intensity projections were determined by conversion of the counting rates from the reconstructed images. All of the resulting PET images were analyzed using ASIPro VM™ software. Whole-body CT scans were acquired with a voltage of 80 kV and 500 μA. 120 rotational steps for a total of 2200 were acquired with a total scan time of 120 s and 145 ms per frame exposure. Combined PET/CT images were processed using Inveon Research Workplace software.

Pretargeted Biodistribution Experiments

Female athymic nude mice bearing subcutaneous SW1222 (right shoulder) xenografts (100-150 $mm^3$, 9-12 days post-inoculation) were administered 100 μg (0.66 nmol) huA33-TCO (in 200 μL 0.9% sterile saline) via intravenous tail vein injection. After an accumulation interval period of 24, 48, or 120 h, the same mice were then administered $^{64}$Cu-Tz-SarAr (300-350 μCi in 200 μL 0.9% sterile saline), also via intravenous tail vein injection (t=0). As in the PET imaging experiments, the specific activity of the radiotracer was adjusted using cold $^{cat}$Cu-Tz-SarAr such that the molar ratio of $Tz_{injected}$:huA$33_{injected}$=1:1. Animals (n=4 per group) were euthanized by $CO_2$(g) asphyxiation at 1, 4, and 24 h after injection. After asphyxiation, tissues were removed, rinsed in water, dried in air for 5 min, weighed, and counted in a gamma counter calibrated for $^{64}$Cu. Counts were converted into activity using a calibration curve generated from known standards. Count data were background- and decay-corrected to the time of injection, and the percent injected dose per gram (% ID/g) for each tissue sample was calculated by normalization to the total activity injected.

Instrumentation

All instruments were calibrated and maintained in accordance with standard quality-control procedures. UV-Vis measurements were taken on a Thermo Scientific NanoDrop 2000 Spectrophotometer. NMR spectroscopy was performed on a Bruker 500 MHz NMR with TopSpin 2.1 software for spectrum analysis. Electrospray ionization mass spectrometry (ESI-MS) spectra were recorded with a Waters Acquity UPLC (Milford, CA) with electrospray ionization SQ detector. High-resolution mass spectrometry (HIRMS) spectra were recorded with a Waters LCT Premier system (ESI). Activity measurements were made using a Capintec CRC-15R Dose Calibrator (Capintec, Ramsey, NJ). For accurate quantification of activities, experimental samples were counted for 1 min on a calibrated Perkin Elmer (Waltham, MA) Automatic Wizard Gamma Counter. Labeling of antibodies with $^{64}$Cu-labeled tetrazine radioligands was monitored using silica-gel impregnated glass-fiber instant thin-layer chromatography paper (Pall Corp., East Hills, NY) and analyzed on a Bioscan AR-2000 radio-TLC plate reader using Winscan Radio-TLC software (Bioscan Inc., Washington, D.C.).

HPLC

All HPLC purifications (6.0 mL/min, Buffer A: 0.1% TFA in water, Buffer B: 0.1% TFA in $CH_3CN$) were performed on a Shimadzu UFLC HPLC system equipped with a DGU-20A degasser, a SPD-M20A UV detector, a LC-6AB pump system, a CBM-20A communication BUS module, and a FRC-10A fraction collector using a Cis reversed phase XTerra© Preparative MS OBD™ column (10 μm, 19.2 mm×250 mm) or a $C_{18}$ reversed phase semi-Prep Phenomenex® Jupiter column (5 μm, 10 mm×250 mm). Quality controls of synthesized compounds were performed using a $C_{18}$ reversed phase Atlantis© T3 column (5 μm, 4.6 mm×250 mm). All radio-HPLC analysis and purification experiments were performed using a Shimadzu HPLC equipped with a $C_{18}$ reversed phase column (Phenomenex Luna analytical 4.6×250 mm), 2 LC-10AT pumps, a SPD-M10AVP photodiode array detector, a Bioscan Flow Counts radioactivity detector, and a gradient of 5:95 $CH_3CN$:$H_2O$ (both with 0.1% TFA) to 95:5 $CH_3CN$:$H_2O$ over 15 min.

Synthesis of Tz-$PEG_7$-AF680

Tz-$PEG_7$-$NH_2$ (1 mg; 0.0015 mmol; 651.8 g/mol) was dissolved in 400 μL DMSO and added to 2 mg AF680-NHS (0.0017 mmol; 1.1 equiv.; ~1150 g/mol). 10 μL triethylamine (7.3 mg; 0.072 mmol; 101.2 g/mol) was then added to this solution, and the solution was placed on an agitating thermomixer at 300 rpm for 30 minutes at room temperature. After 30 minutes, the reaction was purified via preparative Cis HPLC using a gradient of 5:95 $CH_3CN$:$H_2O$ (both with 0.1% TFA) to 95:5 $CH_3CN$:$H_2O$ over 30 min ($t_R$=11.2 min). Lyophilization of the HPLC eluent yielded the purified product as a 2 mg of a bright orange powder (MW~1750; ~0.0011 mmol; ~75% yield).

Preparation of huA33-TCO huA33 (2 mg, 13.3 nmol) was dissolved in 500 μL of phosphate buffered saline (PBS, pH 7.4), and the pH of the solution was adjusted to 8.8-9.0 with $NaHCO_3$ (0.1 M). To this solution was added an appropriate volume of TCO-NHS in DMF (10 mg/mL) to yield a TCO-NHS:huA33 reaction stoichiometry of 10:1. The resulting solution was incubated with gentle shaking for 30 min at room temperature. After 30 min, the modified antibody was purified using size-exclusion chromatography (Sephadex G-25 M, PD-10 column, GE Healthcare; dead volume=2.5 mL, eluted with 500 mL fractions of PBS, pH 7.4) and concentrated with centrifugal filtration units with a 50,000 molecular weight cut off (Amicon™ Ultra 4, Millipore Corp., Billerica, MA) and PBS (pH 7.4).

Determination of the TCO Occupancy of huA33-TCO

A solution of huA33-TCO (100 μg; 0.66 nmol) in 900 μL PBS (pH 7.4) was first prepared (0.74 μM). To this solution, 100 μL of a 1 mM solution of Tz-$PEG_7$-AF680 in DMSO was added to create a reaction solution of 1000 μL and concentrations of 0.66 μM huA33-TCO and 100 μM Tz-$PEG_7$-AF680 (a ~150 fold excess of Tz). This solution was placed on an agitating thermomixer at 300 rpm for 180 minutes at room temperature. After incubation, the resulting fluorophore-labeled immunoconjugate was purified using size-exclusion chromatography (Sephadex G-25 M, PD-10 column, GE Healthcare; dead volume=2.5 mL, eluted with 500 mL fractions of PBS, pH 7.4) and concentrated with centrifugal filtration units with a 50,000 molecular weight cut off (Amicon™ Ultra 4, Millipore Corp., Billerica, MA) and PBS (pH 7.4). The degree of labeling (DOL) was determined via UV-Vis. Absorbance measurements were taken at 280 nm and 680 nm for three separate antibody concentrations. The DOL was calculated using the following formulas:

$$A_{mAb} = A_{280} - A_{max}(CF)$$

$$DOL = [A_{max} * \mathrm{MW}_{mAb}]/[[mAb] * \varepsilon_{AF680}]$$

where the correction factor (CF) for AF680 was given as 0.05 by the supplier, $MW_{huA33}$=150,000, $\varepsilon_{F680}$=184,000, and $\varepsilon_{280,\ mAb}$=225,000. Given the rapid and quantitative nature of the IEDDA reaction, the degree of labeling of AF680 was assumed to be the degree of labeling of TCO.

Determination of Partition Coefficient $^{64}$Cu-Tz-PEG$_7$-NOTA, $^{64}$Cu-Tz-NOTA, or $^{64}$Cu-Tz-SarAr (1 μCi) was added to a mixture of 3 mL PBS (pH 7.4) and 3 mL 1-octanol. The resulting mixture was then vortexed thoroughly for 10 minutes and subsequently centrifuged at 1,000 rpm for 10 min. 1 mL of each layer (PBS and 1-octanol) was then collected, and the amount of radioactivity in each sample was counted on a gamma counter calibrated for $^{64}$Cu. The partition coefficient (log D) was calculated using the formula:

$$\mathrm{Log}\, D = \log_{10}\left[(\mathrm{counts}_{octanol})/(\mathrm{counts}_{PBS}\right]$$

All experiments were performed in triplicate.

Reaction of $^{64}$Cu-Tz Radioligands with huA33-TCO

In order to check their reactivity with TCO, $^{64}$Cu-Tz-PEG$_7$-NOTA and $^{64}$Cu-Tz-SarAr were added to a solution of huA33 in PBS (500 μL, pH 7.4) at a molar ratio of Tz:mAb of 1:1. The resulting solution was placed on an agitating thermomixer at 300 rpm for 30 minutes at room temperature. After this incubation, the progress of the reaction was assayed using radio-TLC with reverse-phase $C_{18}$ TLC plates and a mobile phase of 1:1 $CH_3CN$:water (each with 0.1% TFA). Under these conditions, the $^{64}$Cu-labeled antibody will remain at the baseline, while the $^{64}$Cu-Tz-labeled radioligands will travel up the plate. If the purified radioimmunoconjugate is desired, the $^{64}$Cu-Tz huA33 was then purified using size-exclusion chromatography (Sephadex G-25 M, PD-10 column, GE Healthcare; dead volume=2.5 mL, eluted with 500 mL fractions of PBS, pH 7.4). Typically, crude radiochemical yields of 90-95% were obtained, and post-purification radiochemical purities were greater than 99% (corresponding to specific activities of 2.0-2.5 mCi/mg). All experiments were performed in triplicate.

PBS and Serum Stability of $^{64}$Cu-Tz-PEG$_7$-NOTA and $^{64}$Cu-Tz-SarAr $^{64}$Cu-Tz-PEG$_7$-NOTA and $^{64}$Cu-Tz-SarAr (1000 μCi) were incubated on an agitating thermomixer (300 rpm) at 37° C. in 500 μL of either PBS (pH 7.4) or human serum. At each prescribed time-point, 100 μL of the solution was removed and placed into a 1.7 mL microcentrifuge tube. For the PBS samples, the compound was injected directly onto the HPLC and analyzed using a gradient of 5:95 $CH_3CN$:$H_2O$ (both with 0.1% TFA) to 95:5 $CH_3CN$:$H_2O$ over 15 min. For the serum samples, 100 μL cold $CH_3CN$ was added to the serum, and the resultant mixture was vortexed and centrifuged at 10,000 rpm for 10 min. After this, the clear supernatant was removed, moved to a new 1.7 mL microcentrifuge tube, and centrifuged again at 10,000 rpm for 10 min. The clear supernatant from this second spin was then injected into the HPLC and analyzed using a gradient of 5:95 $CH_3CN$:$H_2O$ (both with 0.1% TFA) to 95:5 $CH_3CN$:$H_2O$ over 15 min. The residual protein from the centrifuge spins was checked for radioactivity, and only minimal residual activity remained (less than 1% of the starting $^{64}$Cu for each $^{64}$Cu-Tz-PEG$_7$-NOTA and $^{64}$Cu-Tz-SarAr). The fraction of intact $^{64}$Cu-Tz-PEG$_7$-NOTA or $^{64}$Cu-Tz-SarAr was determined by integrating the peak corresponding to the compound ($t_R$=9.7 and 8.7 minutes, respectively) and dividing by the integral over the whole HPLC run. Both the injection loop and column were monitored to detect the presence of residual activity. All experiments were performed in triplicate.

In Vivo Stability of $^{64}$Cu-Tz-SarAr

Healthy athymic nude mice were injected with $^{64}$Cu-Tz-SarAr (300-350 μCi) via intravenous tail vein injection. After 15 min, 1 h, or 4 h, the mice were sacrificed via $CO_2$ asphyxiation, and their blood (500 μL) was collected via cardiac puncture in heparinized 1.7 mL microcentrifuge tubes. These tubes were then centrifuged at 10,000 rpm for 10 minutes to separate plasma from red-blood cells. After 10 minutes, the plasma supernatant was then transferred to a new 1.7 mL microcentrifuge tube and placed on ice. Subsequently, 500 μL of ice-cold $CH_3CN$ was added to the plasma to precipitate the proteins, and the tubes were vortexed briefly and centrifuged again for 10 min at 10,000 rpm. After this centrifugation, the supernatant was carefully removed and transferred to another 1.7 mL microcentrifuge tube, in which it was subjected to another round of centrifugation at 10,000 rpm for 10 min. After this final centrifugation, the supernatant was again transferred to a clean 1.7 mL microcentrifuge tube. This solution was then analyzed via radio-TLC methods using reverse-phase $C_{18}$ TLC plates and a mobile phase of 1:1 $CH_3CN$:water (each with 0.1% TFA). Using this method, any free $^{64}Cu^{2+}$ will remain at the baseline, while $^{64}$Cu-Tz-SarAr and other metabolites will travel up the TLC plate. The fraction of intact $^{64}$Cu-Tz-SarAr was calculated by dividing the integral of the parent compound peak over the integral of the entire radio-TLC chromatogram. All experiments were performed in triplicate.

Cell Culture

Human colorectal cell line SW1222 was obtained from the Ludwig Institute of Cancer Research and maintained in Iscove's Modified Dulbecco's Medium, supplemented with 10% heat-inactivated fetal calf serum, 2.0 mM glutamine, 100 units/mL penicillin, and 100 units/mL streptomycin in a 37° C. environment containing 5% $CO_2$. Cell lines were harvested and passaged weekly using a formulation 0.25% trypsin/0.53 mM EDTA in Hank's Buffered Salt Solution without calcium and magnesium.

Xenograft Models

All animal experiments we performed under an Institutional Animal Care and Use Committee-approved protocol, and the experiments followed institutional guidelines for the proper and humane use of animals in research. Six to eight week-old athymic nude female mice were obtained from Charles River Laboratories (Wilmington, MA). Animals were housed in ventilated cages, were given food and water ad libitum, and were allowed to acclimatize for approximately 1 week prior to inoculation. SW1222 tumors were induced on the right shoulder by a subcutaneous injection of 5.0×10$^6$ cells in a 150 μL cell suspension of a 1:1 mixture of fresh media:BD Matrigel (BD Biosciences, Bedford, Ma). The xenografts reached ideal size for imaging and biodistribution (~100-150 mm$^3$) in approximately 18-21 days.

Immunoreactivity Assays

Immunoreactivity assays employing the huA33-TCO antibodies labeled with the $^{64}$Cu-Tz radioligands were performed as previously reported using A33 antigen-expressing SW1222 human colorectal cancer cells. All experiments were performed in triplicate.

PET Imaging with $^{64}$Cu-Labeled Tetrazine Radioligands

All PET imaging experiments were performed on an Inveon PET/CT scanner (Siemens Healthcare Global). Healthy female athymic nude mice (n=4 per radioligand) were administered $^{64}$Cu-Tz-NOTA, $^{64}$Cu-Tz-PEG$_7$-NOTA, or $^{64}$Cu-Tz-SarAr (300-350 μCi in 200 μL 0.9% sterile saline) via intravenous tail vein injection (t=0). Approximately 5 minutes prior to the PET images, mice were anesthetized by inhalation of 2% isoflurane (Baxter Healthcare, Deerfield, IL)/oxygen gas mixture and placed on the scanner bed; anesthesia was maintained using 1% isoflurane/gas mixture. Static scans were recorded at various time points after injection with a minimum of 30 million coincident events (10-30 min total scan time). An energy window of 350-700 keV and a coincidence timing window of 6 ns were used. Data were sorted into 2-dimensional histograms by Fourier re-binning, and the images were reconstructed using a two-dimensional ordered subset expectation maximization (2DOSEM) algorithm (16 subsets, 4 iterations) into a 128×128×159 (0.78×0.78×0.80 mm) matrix. The image data was normalized to correct for non-uniformity of response of the PET, dead-time count losses, positron branching ratio, and physical decay to the time of injection but no attenuation, scatter, or partial-volume averaging correction was applied. Activity concentrations (percentage of dose per gram of tissue [% ID/g]) and maximum intensity projections were determined by conversion of the counting rates from the reconstructed images. All of the resulting PET images were analyzed using ASIPro VM™ software.

Acute Biodistribution with $^{64}$Cu-Labeled Tetrazine Radioligands

Healthy female athymic nude mice (n=4 per radioligand) were administered $^{64}$Cu-Tz-PEG$_7$-NOTA or $^{64}$Cu-Tz-SarAr (25-30 μCi in 200 μL 0.9% sterile saline) via intravenous tail vein injection (t=0). Animals (n=4 per group) were euthanized by $CO_2$(g) asphyxiation at 1, 4, 12, and 24 h after injection. After asphyxiation, tissues were removed, rinsed in water, dried in air for 5 min, weighed, and counted in a gamma counter calibrated for $^{64}$Cu. Counts were converted into activity using a calibration curve generated from known standards. Count data were background- and decay-corrected to the time of injection, and the percent injected dose per gram (% ID/g) for each tissue sample was calculated by normalization to the total activity injected.

Ex Vivo Autoradiography, Immunohistochemistry, and Histology

Following PET imaging, tumors were excised and embedded in optimal-cutting-temperature mounting medium (OCT, Sakura Finetek) and frozen on dry ice. Series of 10 m frozen sections were then cut. To determine radiotracer distribution, digital autoradiography was performed by placing tissue sections in a film cassette against a phosphor imaging plate (Fujifilm BAS-MS2325; Fuji Photo Film) for an appropriate exposure period at −20° C. Phosphor imaging plates were read at a pixel resolution of 25 μm with a Typhoon 7000 IP plate reader (GE Healthcare). After autoradiographic exposure, the same frozen sections were then used for fluorescence staining and microscopy. Immunofluorescence staining and imaging of A33 was performed essentially as previously described by Oehler et al. in "$^{18}$F-fluromisonidazole PET imaging as a biomarker for the response to 5,6-dimethylxanthenone-4-acetic acid in colorectal xenograft tumors. *Journal of Nuclear Medicine* 2011, 52 (3), 437-44. Frozen sections were fixed in 4% paraformaldehyde, and subsequently incubated with huA33 primary antibody (5 μg/ml) overnight at 4° C., followed by secondary detection using goat anti human Alexa-568 for 1 h at room temperature (20 μg/ml, Molecular Probes). Whole mount fluorescence images were acquired at ×40 magnification using a BX60 fluorescence microscope (Olympus America, Inc.) equipped with a motorized stage (Prior Scientific Instruments Ltd.) and CC12 camera (Olympus). Whole-tumor montage images were obtained by acquiring multiple fields at ×40 magnification, followed by alignment using MicroSuite Biologic Suite (version 2.7; Olympus). Fluorescence and autoradiographic images were registered using Adobe Photoshop (CS6).

Dosimetry

Mouse biodistribution data were expressed as normal-organ mean standard uptake values (SUVs) versus time post-administration. In first order, that SUVs were independent of body mass and thus the same among species, the mean SUV in mouse organ i, $SUV_{organ\ i\backslash Mouse}$, was converted to the fraction of the injected dose in each human organ I, $FID_{organ\ I\backslash Human}$, using the following formula:

$$FID_{Organ\ i|Human} = SUV_{ran\ i|Mouse} \cdot \frac{\text{Mass of Human Organ } i}{\text{Mass of Human Total Body}}$$

and the organ and total-body masses of the 70-kg Standard Man anatomic model. These data (corrected for radioactive decay to the time of injection) were then fit to a mono-exponential or bi-exponential time-activity function, depending on the organ. The cumulated activity, or residence time, in human organ i, μC i, in $\mu C_i$ h/μCi, was then calculated by analytically integrating the time-activity function in organ i, replacing the biological clearance constant, $(\lambda_b \lambda_j$. for each component j of the fitted exponential function with the corresponding effective clearance constant, $(\lambda_e \lambda_j = (\lambda_b \lambda_j + \lambda_p$, where $\lambda_p$ is the physical decay constant of the radionuclide. The resulting organ residence times were entered into the OLINDA computer program to yield the mean organ absorbed doses and effective dose in rad/mCi and rem/mCi, respectively.

Statistical Analysis

Data were analyzed by the unpaired, two-tailed Student's t-test. Differences at the 95% confidence level (P less than 0.05) were considered to be statistically significant.

$^{18}$F-based of Tetrazine Radioligands for Pretargeted Imaging

Described herein is the development of strategies for pretargeted PET imaging of pancreatic cancer featuring a tetrazine-bearing radioligand with an improved pharmacokinetic profile compared to prior systems. A TCO-bearing immuno-conjugate of the anti-CA19.9 antibody 5B1 and an Al[$18^F$]-NOTA-labeled tetrazine radioligand were harnessed for the visualization of CA19.9-expressing BxPC3 pancreatic cancer xenografts. Biodistribution and $^{18}$F-PET imaging data clearly demonstrate that this methodology effectively delineates tumor mass with activity concentrations up to 6.4% ID/g at 4 h after injection of the radioligand.

Figure 27:
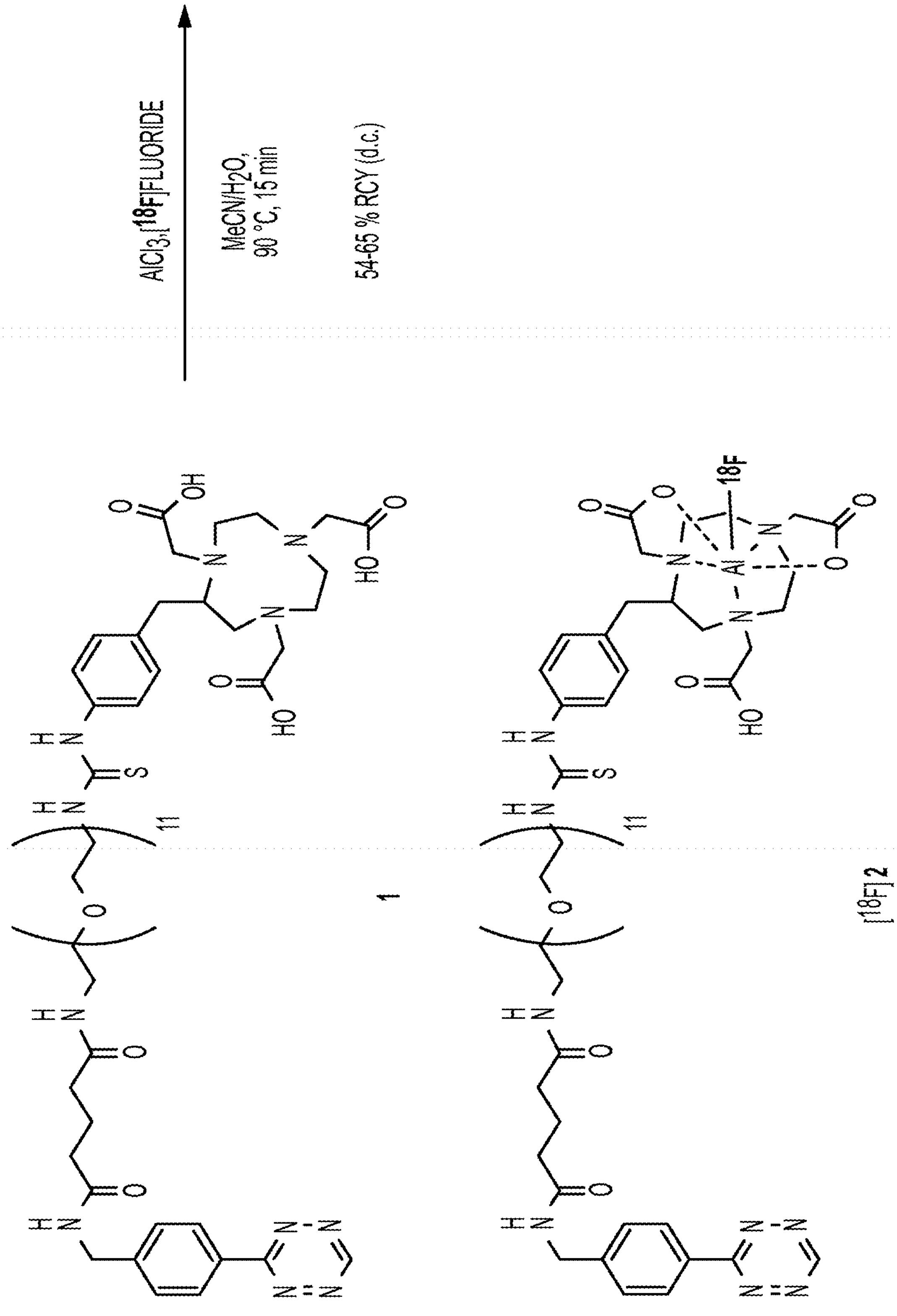
FIG. 27 shows the radiochemical synthesis of the radioligand Tz-PEG$_{11}$-Al$^{18}$F-NOTA ([$^{18}$F]2). [$^{18}$F]2 was obtained in 54-56% radiochemical yields (RCY) (d.c.) and high specifica activities (SAs) (21.4-26.7 GBq/µmol) after a total synthesis time of 108 min. Purification of the crude reaction mixture using a C18-cartridge gave [$^{18}$F]2 in purities of greater than 96%.

The development of a novel Tz/TCO-based pretargeting strategy using an Al[$^{18}$F]-NOTA-labeled tetrazine radioligand is described herein. As described below, the 5B1 antibody, a fully-human IgG that targets a promising biomarker for pancreatic ductal adenocarcinoma: carbohydrate antigen 19.9 (CA19.9) was selected. In order to functionalize the antibody with a reactive bioorthogonal moiety, purified 5B1 was incubated with an activated succinimidyl ester of TCO (TCO-NHS, 35 eq.) at room temperature for 1 h. The immunoconjugate was subsequently purified by gel-filtration chromatography. The precursor to the radioligand, Tz-$PEG_{11}$-NOTA (FIG. 27, 1), was synthesized from three commercially available building blocks: (i) 2,5-dioxo-1-pyrrolidinyl 5-[4-(1,2,4,5-tetrazin-3-yl)benzylamino]-5-oxopentanoate (Tz-NHS), (ii) O-(2-aminoethyl)-O'-[2-(boc-amino)ethyl]decaethylene glycol ($NH_2$-$PEG_{11}$-NHBoc), and (iii) S-2-(4-isothiocyanatobenzyl)-1,4,7-triaza-cyclononane-1,4,7-triacetic acid (p-SCN-Bn-NOTA). After the peptide coupling between Tz-NHS and $NH_2$-$PEG_{11}$-NHBoc and the subsequent deprotection of the terminal tert-butyloxycarbonyl protecting group, the resulting Tz-$PEG_{11}$-$NH_2$ moiety was reacted with the bifunctional p-SCN-Bn-NOTA chelator. Ultimately, the precursor was prepared in very high purity (greater than 98%) and with an overall yield of ~15% (n=3).

The $^{18}$F-labeled radioligand Tz-$PEG_{11}$-Al[$^{18}$F]-NOTA ([$^{18}$F]2 (FIG. 27, 2) was obtained in 54-65% radiochemical yield [decay-corrected (d.c.) to the start of synthesis] in high purity (greater than 96%) and had a specific activity between 21.4-26.7 GBq/μmol. The use of metal-free solvents, the pH of the Al[$^{18}$F]-NOTA complexation reaction (pH=4), and the ratio of reaction solvents (at least 3:1 MeCN/$H_2O$) all proved to be crucial factors in obtaining high radiochemical yields. Aqueous [$^{18}$F]fluoride (non-carrier added) was obtained from the cyclotron and loaded onto a preconditioned anion-exchange (QMA) cartridge. Before elution of the [$^{18}$F]fluoride using 0.4 M $KHCO_3$-solution (0.2 mL), the cartridge was washed with metal-free water (10-15 mL) to elute metal ions present in the original target water. Metal-free glacial acid (~15-20 μL) was used to adjust the pH to ~3.5-4, followed by the addition of 2 mM $AlCl_3$-solution (25 μL). The resulting mixture was incubated at room temperature for the formation of the Al-$^{18}$F complex. Precursor 1 (40 nmol in 700 μL MeCN) was then added to the solution of Al[$^{18}$F], and the resulting mixture was stirred at 90° C. for 15 min. Subsequently, the $^{18}$F-labeled product was purified using a SepPak C18-cartridge (Waters, Milford, MA) and eluted with a small volume of ethanol (0.3-0.4 mL). The in vitro stability of [$^{18}$F]2 was assayed by incubation in phosphate buffered saline (PBS, pH 7.4) or human serum at 37° C., followed by analysis via radio-HPLC. In PBS, negligible decomposition could be observed after 4 h (92±2.3% intact), and 79±4.4% (n=4) of the radioligand remained intact in human serum at the same time point. Given the fast reaction kinetics of the IEDDA ligation as well as the relatively short half-life of $^{18}$F, the observed degradation rate is not considered a detriment to the system, as shown for other Tz/TCO approaches.

The bioorthogonal click reaction between [$^{18}$F]2 and the TCO moiety on the antibody was demonstrated by incubation of equimolar amounts (1.33 nmol) of the purified radioligand with 5B1-TCO at room temperature. Analysis of the reaction via radio-TLC (mobile phase: 90% MeCN in H2O) revealed a greater than 94% yield for the reaction, with the $^{18}$F-labeled click reaction product situated at the origin, while the free radioligand can be detected at the solvent front.

In vivo biodistribution data for Tz-$PEG_{11}$-Al[$^{18}$F]-NOTA were first obtained in healthy mice by injecting [$^{18}$F]2 alone (1.8-2.0 MBq) via the tail vein. The data showed accumulation and retention of the radiotracer in the large intestines and feces with 0.32±0.87 percent injected dose per gram (% ID/g) at 1 h after injection to 1.73±0.45 (% ID/g) at 4 h. The uptake and retention of [$^{18}$F]2 could also be observed in the kidneys (2.12±0.23% ID/g at 1 h to 1.17±0.12% ID/g at 4 h), indicating dual renal and fecal elimination pathways for the radioligand. The amount of activity in the blood decreased over time, from 1.94±0.23% ID/g at 1 h to 0.78±0.08% ID/g at 4 h after injection, while the uptake in all other healthy tissues remained less than 1% ID/g. Notably, the activity concentrations in the bone were particularly low (not exceeding 0.2% ID/g), illustrating in vivo stability of the Al[$^{18}$F]-NOTA complex. In accompanying experiments, the blood half-life of the radioligand was calculated to be 71.2 min.

Figure 28:
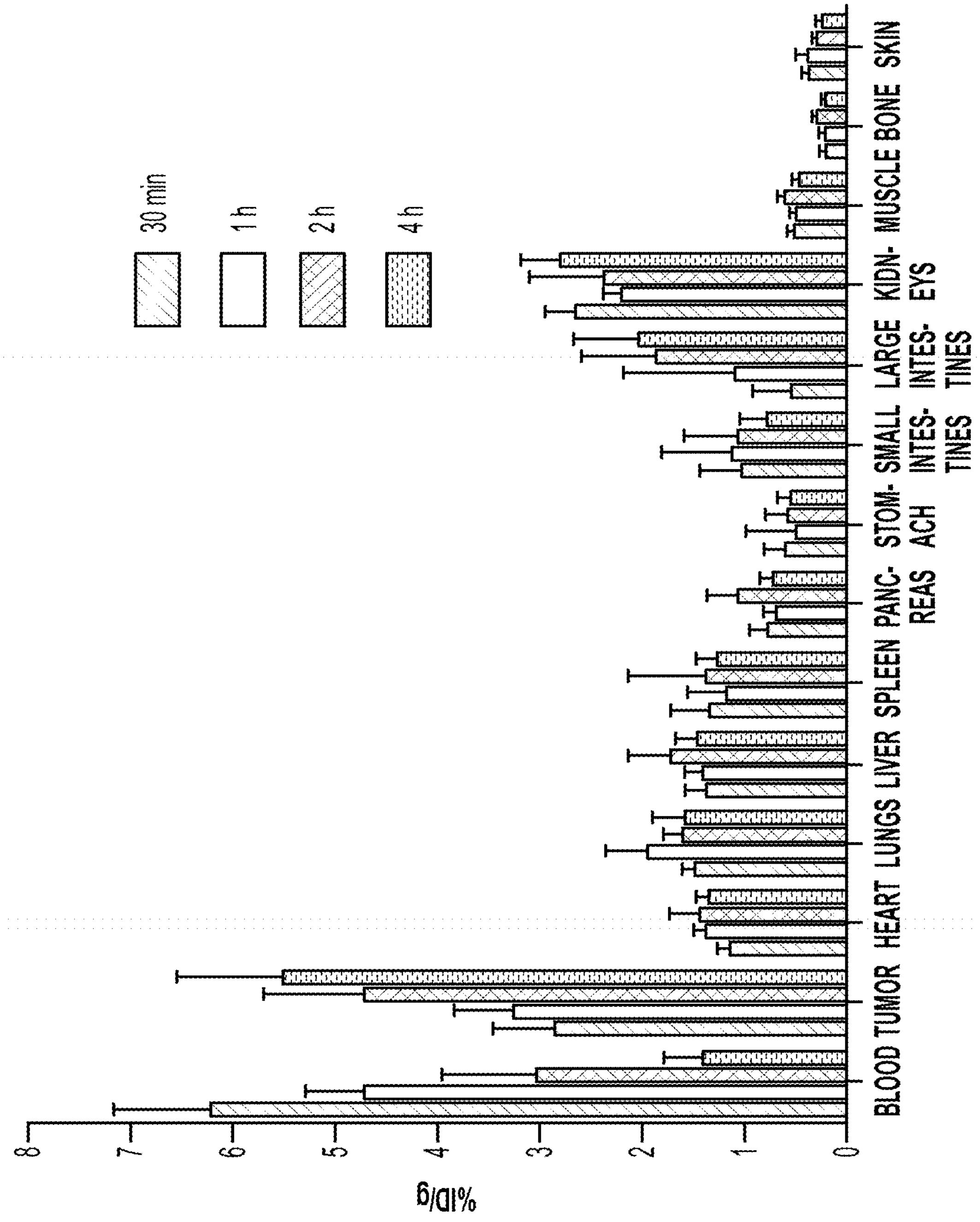
FIG. 28 shows results of the biodistribution pretargeting CA19.9 with [$^{18}$F]2/5B1-TCO. Subcutaneous BxPC3 xenograft bearing mice were administered 5B1-TCO (1.33 nmol) 72 h prior to the injection of the $^{18}$F-labeled tracer (1.33 nmol, 1.8-2.0 MBq) via the tail vein before the mice were euthanized and the organs collected at the appropriate time points.

In subsequent pretargeted biodistribution experiments, nude, athymic mice bearing subcutaneous CA19.9-expressing BxPC3 xenografts were injected with 5B1-TCO (1.33 nmol) 72 h prior to the administration of [$^{18}$F]2 (1.33 nmol, 1.8-2.0 MBq). The data revealed increasing tumoral uptake over the course of the study (3.0±0.32% ID/g at 30 min, 3.52±0.67% ID/g at 1 h, 4.81±1.23% ID/g at 2 h to 5.6±0.85% ID/g at 4 h), with the amount of radioactivity in the blood decreasing in kind, from 6.13±0.86% ID/g at 30 min to 1.75±0.22% ID/g at 4 h. In accordance to the biodistribution data obtained from healthy mice, the uptake in other tissue remained generally low (less than or equal to 2% ID/g), with the highest uptake and retention in the clearance organs: the intestines and kidneys (FIG. 28).

The clearance of radioactivity from the blood pool was generally in line with the calculated blood half-life of the radiotracer, and the steady uptake of radioactivity at the tumor suggested that the radioligand is primarily clicking with 5B1-TCO at the tumor site rather than clicking in the blood pool followed by accumulation at the tumor.

Figure 29:
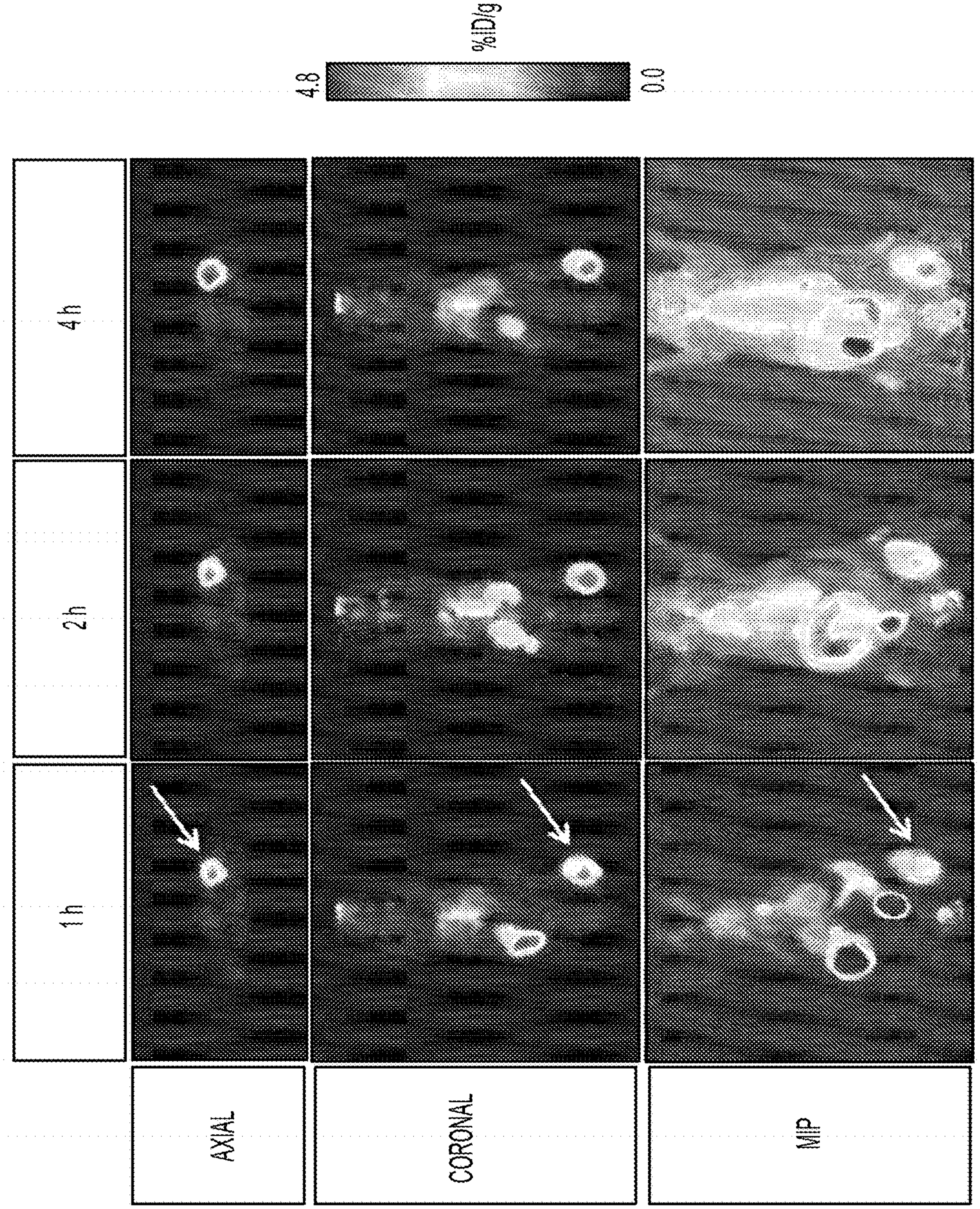
FIG. 29 shows PET images of Tz-PEG$_{11}$-NOTA-Al$^{18}$F/5B1-TCO pretargeting strategy. Subcutaneous BxPC3 xenograft bearing mice were administered 5B1-TCO (1.33 nmol) 72 h prior to the injection of the $^{18}$F-labeled tracer (1.33 nmol, 18-20 MBq) via the tail vein. Transverse (top) and coronal (middle) planar images intersect the center of the tumors. The maximum intensity projections (MIPs, bottom) clearly illustrate tumor uptake after 1 h with increasing tumor-to-background ratios over the course of the experiment.

Small animal PET imaging experiments were conducted in a similar fashion, with the only difference in the amount of radioactivity injected (18-20 MBq, 1.33 nmol of [$^{18}$F]2, equimolar to 5B1-TCO). The PET images as shown in FIG. 29 confirm the data obtained in the biodistribution study: the signal in the tumor increases with time, while the activity concentrations in the blood and intestines concomitantly decrease. This results in the clear delineation of the tumor from background tissue, with the tumor-to-background activity ratios improving over the course of the experiment. The tumoral uptake of [$^{18}$F]2 is immediately evident 1 h after injection; however, the signal grows to 6.4% ID/g at 4 h after the administration of the radioligand. While the tumor-to-background activity concentration ratios improve over time, radioactivity had not cleared the intestines at 4 h post-injection. Therefore, second generation tetrazine-bearing radioligands can be developed in an effort to determine whether structural alterations can increase the fraction of the radioligand that is excreted via the renal system, and thus create higher tumor-to-background ratios at earlier time points. Finally, using the biodistribution data, a dosimetric analysis of the pretargeting strategy was performed that confirms that pretargeted PET imaging with Tz-$PEG_{11}$-Al$^{18}$F-NOTA and 5B1-TCO confers a significant dosimetric advantage over the use of antibodies directly labeled with long-lived radioisotopes (e.g., in the case $^{89}$Zr-DFO-5B1). The effective dose of the presented $^{18}$F-based pretargeting system (0.03 rem/mCi) is more than 60 times lower than directly labeled $^{89}$Zr-DFO-5B1 (2.02 rem/mCi).

Thus, the $^{18}$F-based pretargeted PET imaging system described herein shows highly promising biodistribution results and produced tumor activity concentrations of up to 6.4% ID/g at 4 h post-injection. Small-animal PET imaging experiments revealed that this methodology clearly delineates CA19.9-expressing tissues, with especially enticing tumor-to-background activity ratios 2 h and 4 h after injection of the radiotracer.

All starting materials except the NOTA-Bn-p-NSC that was purchased from Macrocyclics were purchased from Sigma-Aldrich (synthetic-grade) and were used without further purification. All solvents used for HPLC analysis and purification within this project were purchased from Fisher Scientific (HPLC grade). Metal-free DMSO (greater than or equal to 99.99995%) and MeCN (greater than or equal to 99.999%) were purchased from Sigma-Aldrich. Water (greater than 18.2 MΩ cm−1 at 25° C.) was obtained from an Alpha-Q Ultrapure water system from Millipore (Bedford, MA).

Proton ($^{1}H$) NMR spectra were measured on a BrukerAvance Ultra Shield (500 MHz) spectrometer at ambient temperature. Data were recorded as follows: chemical shift in ppm from internal reference tetramethylsilane on the scale, multiplicity (s=singlet; d=doublet; t=triplet; m=multiplet), coupling constant (Hz), integration, and assignment. Carbon ($^{13}C$) NMR spectra were measured on a BrukerAvance Ultra Shield (125 MHz) spectrometer at ambient temperature. Chemical shifts were recorded in ppm from the solvent resonance employed as the internal standard (deuterochloroform at 77.00 ppm).

Non-carrier-added (n.c.a.) $^{18}F$-fluoride was obtained via the $^{18}O(p,n)^{18}F$ nuclear reaction of 11-MeV protons in an EBCO TR-19/9 cyclotron using enriched $^{18}O$-water. QMA light ion-exchange cartridges and C-18 light Sep-Pak© cartridges were obtained from Waters (Milford, MA). C18 cartridges were equilibrated using absolute ethanol (10 mL) followed by deionized water (5 mL). QMA cartridges used a Chromafix 30-PS-HCO3-resin for ion-exchange and were equilibrated using KHCO3-solution (0.4 M, 5 mL) followed by deionized water (10 mL). High performance liquid chromatography (HPLC) purification and analysis was performed on a Shimadzu UFLC HPLC system equipped with a DGU-20A degasser, a SPD-M20A UV detector, a RF-20Axs fluorescence detector, a LC-20AB pump system, and a CBM-20A communication BUS module. A LabLogic Scan-RAM radio-TLC/HPLC-detector was used for purifications while a PosiRAM Model 4 was used for analysis. HPLC solvents (Buffer A: 0.1% TFA in water, Buffer B: 0.1% TFA in MeCN) were filtered before use. HPLC analysis of radioactive and non-radioactive compounds was performed on a reversed phase Atlantis T3 column (C18, 5 μm, 4.6 mm×250 mm). Preparative HPLC purification was carried out on a reversed phase Waters XTerra Prep C18 OBD (C18, 10 μm, 19 mm×250 mm). For radioactive thin-layer chromatography (TLC) analysis throughout this work, Merck precoated TLC plates (C18, reversed-phase) were used. Radio-TLC was performed using a Canberra 190 5 Experimental Part UNISPEC iScan (Meriden, CT, USA) instrument. Radioactivity was determined using a calibrated ion chamber (Capintec CRC-15R).

Electrospray ionization mass spectrometry (ESI-MS) spectra were recorded with a Shimadzu LC-2020 with electrospray ionization SQ detector. High-resolution mass spectrometry (ESI-HRMS) was carried out on a Micromass LCT Premier XE using a reversed phase Waters XBridge column (C18, 5 μm, 4.6 mm×50 mm).

Syntheses tert-butyl-(1-(4-(1,2,4,5-tetrazin-3-yl)phenyl)-3,7-dioxo-11,14,17,20,23,26,29,32,35,38,41-un-de-caoxa-2,8-diazatritetracontan-43-yl)carbamate (Tz-$PEG_{11}$-NHBoc)

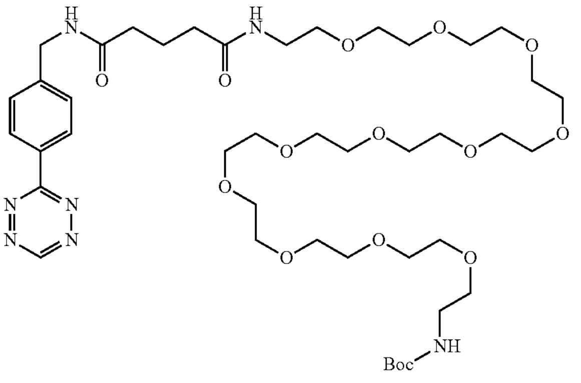

MW = 928.09 g/mol; $C_{43}H_{73}N_7O_{15}$ 2,5-Dioxo-1-pyrrolidinyl 5-[4-(1,2,4,5-tetrazin-3-yl)benzalamino]-5-oxopentanoate (Tz-NHS, 10 mg, 0.025 mmol) was dissolved in anhydrous dimethylsulfoxide (DMSO, 0.5 mL) before O-(2-Aminoethyl)-O'-[2-(Boc-amino)ethyl]decaethylene glycol (24.2 mg, 0.0375 mmol) and TEA (0.0057 mL, 0.0375 mmol) were added. The reaction mixture was stirred at room temperature for 45 min. After completion of the reaction (monitored by HPLC, 5% MeCN/H to 95% MeCN over 20 min, $R_t$=14.2 min, 1 mL/min) the product was purified using preparative HPLC (5% MeCN/H to 95% MeCN over 20 min, $R_t$=14.5 min, 8 mL/min) with purity greater than 95%. The product was furnished as a pink solid (18.2 mg, 96%). $^{1}H$ NMR (500 MHz, DMSO-$d_6$) δ 10.65 (s, 1H), 8.77 (t, J=5.4 Hz, 1H), 8.65-8.57 (m, 2H), 8.16-8.12 (m, 2H), 6.77-6.73 (m, 1H), 3.62-3.42 (m, 46H), 3.38 (t, J=6.1 Hz, 3H), 3.07 (q, J=5.8 Hz, 2H), 1.38 (s, 9H); MS (ESI) m/z 929.3 $[M+H]^+$, HRMS (ESI) calcd. for $C_{43}H_{73}N_7NaO_{15}$ $[M+Na]^+$ m/z 950.5062 found 950.5034.

$N^1$-(4-(1,2,4,5-tetrazin-3-yl)benzyl)-$N^5$-(35-amino-3,6,9,12,15,18,21,24,27,30,33-undecaoxa-pentatriacontyl)glutaramide (Tz-$PEG_{11}$-$NH_2$)

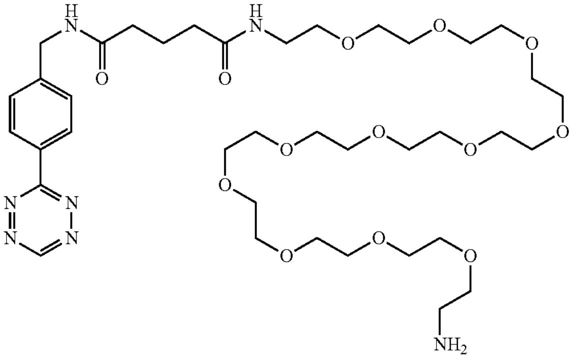

MW = 827.97 g/mol; $C_{38}H_{65}N_7O_{13}$

Tz-PEG$_{11}$-NHBoc (16.3 mg, 0.0216 mmol) was dissolved in dichloromethane (DCM, 0.5 mL) before TFA (0.1 mL) was added drop wise. The resulting solution was stirred at room temperature for 30 min. The solvent was removed under reduced pressure before the deprotected product was purified via preparative HPLC (5% MeCN/H to 95% MeCN over 20 min, $R_t$=11.6 min, 8 mL/min) with purity greater than 97% The product was furnished as a pink solid (14.4 mg, 92%). $^1$H NMR (500 MHz, DMSO-d$_6$) δ 10.59 (s, 1H), 8.74 (t, J=5.2 Hz, 1H), 8.61-8.55 (m, 2H), 8.12-8.09 (m, 2H), 6.79-6.74 (m, 1H), 3.68-3.36 (m, 46H), 3.34 (t, J=6.1 Hz, 3H), 3.10 (q, J=5.8 Hz, 2H); MS (ESI) m/z 829.2 [M+H]$^+$, HRMS (ESI) calcd for $C_{38}H_{66}N_7O_{13}$ [=M+H]$^+$ m/z 828.4719 found 828.4742.

2,2',2"-(3-(4-(3-(1-(4-(1,2,4,5-tetrazin-3-yl)phenyl)-3,7-dioxo-11,14,17,20,23,26,29,32,35,38,-41-undecaoxa-2,8-diazatritetracontan-43-yl)thioureido)benzyl)-1,4,7-triazonane-2,5,8-triyl)triacetic acid (Tz-PEG$_{11}$-NOTA)

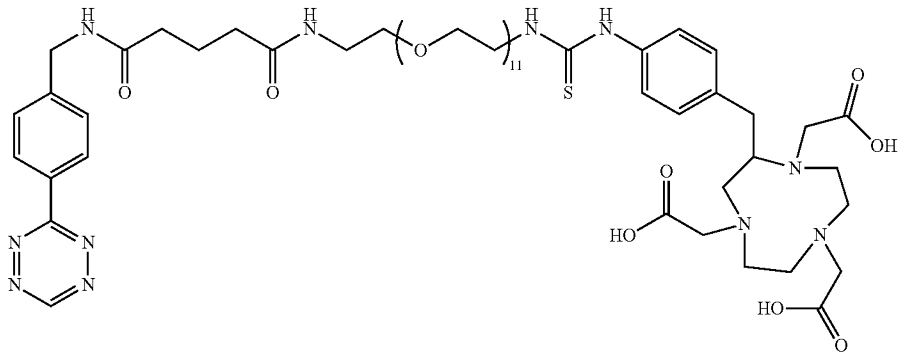

MW = 1278.48 g/mol; $C_{58}H_{91}N_{11}O_{19}S$

Tz-PEG$_{11}$-NH$_2$ (13.5 mg, 0.0216 mmol) was dissolved in DMSO (0.5 mL) before NOTA-Bn-NCS (20.2 mg, 0.036 mmol) and TEA (0.0057 mL, 0.0375 mmol) were added. The reaction mixture was stirred at room temperature for 45 min. After completion of the reaction (monitored by HPLC, 5% MeCN/H to 95% MeCN over 20 min, $R_t$=13.2 min, 1 mL/min) the product was purified using preparative HPLC (5% MeCN/H$_2$O to 95% MeCN over 30 min, $R_4$=13.6 min, 8 mL/min) with purity greater than 97% The product was furnished as a pink solid (20.2 mg, 73%). $^1$H NMR (500 MHz, DMSO-d$_6$) δ 10.59 (s, 1H), 8.47 (d, J=7.3 Hz, 3H), 7.87 (t, J=5.2 Hz, 3H), 7.55 (d, J=7.6 Hz, 3H), 7.43 (d, J=8.1 Hz, 3H), 7.20 (d, J=7.7 Hz, 2H), 4.41 (d, J=5.8 Hz, 3H), 4.00 (d, J=17.5 Hz, 2H), 3.82 (d, J=17.9 Hz, 4H), 3.51 (s, 53H), 2.20 (t, J=7.4 Hz, 3H), 2.12 (t, J=7.5 Hz, 5H), 1.78 (dt, J=14.4, 7.2 Hz, 4H); MS (ESI) m/z 829.2 [M+H]$^+$, HRMS (ESI) calcd for $C_{43}H_{73}N_7O_{15}$ [=M−H]$^-$ m/z 1276.6135 found 1276.6179.

Tz-PEG$_{11}$-Al[$^{18}$F]-NOTA.

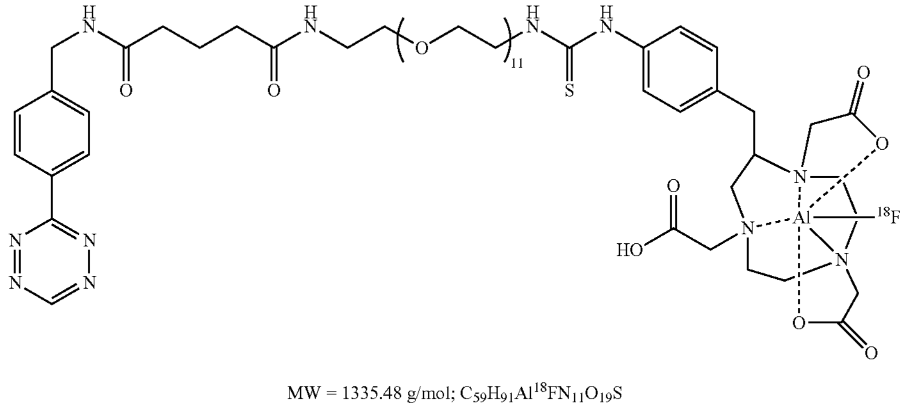

MW = 1335.48 g/mol; $C_{59}H_{91}Al^{18}FN_{11}O_{19}S$

The [18F]fluoride received from the cyclotron was trapped on a preconditioned QMA cartridge. The cartridge was subsequently washed with metal-free water (10-15 mL) before the [18F]fluoride (0.9-1.1 GBq) was eluted using 0.4 M KHCO3-solution (0.2 mL) into a V-vial. The pH of the solution was adjusted to ~4 using glacial acetic acid (15-20 μL) followed by the addition of 2 mM AlCl3-solution (25 μL). The resulting solution was incubated at room temperature for 20 min to form the Al-18F complex. The precursor $Tz-PEG_{11}$-NOTA dissolved in MeCN (700 μL) was then added to the aqueous solution containing the Al-18F complex and the resulting mixture stirred at 90° C. for 15 min. After the given period of time the reaction vial was cooled using dry ice before the reaction mixture was diluted with water (20 mL). The obtained aqueous solution containing the labeled product was flushed through a preconditioned C18 cartridge followed by an additional 10 mL of water to remove left over [18F]fluoride from the cartridge. The product [18F]2 was subsequently eluted with EtOH (0.3-05 mL) and analyzed for purity using radio-HPLC (5% $MeCN/H_2O$ to 95% MeCN over 20 min, Rt=11.5 min, 1 ml/min). Prior to each animal experiment the EtOH was removed under reduced pressure and the tracer was reconstituted in 0.9% saline for injections.

In vitro Stability Testing

Table 24 shows results obtained from the in vitro stability study of the radioligand [18F]2. The values are given as percent intact tracer after incubation.

TABLE 24

| | Conditions | |
|---|---|---|
| Time | PBS (pH =7.4) [%] | Human Serum [%] |
| 30 min | 98.5 ± 1.0 | 95.5 ± 1.5 |
| 1 h | 96.5 ± 2.5 | 91.5 ± 2 |
| 2 h | 93 ± 1.0 | 85 ± 4.5 |
| 4 h | 91.5 ± 1.5 | 74.5 ± 5.5 |

Figure 30B:
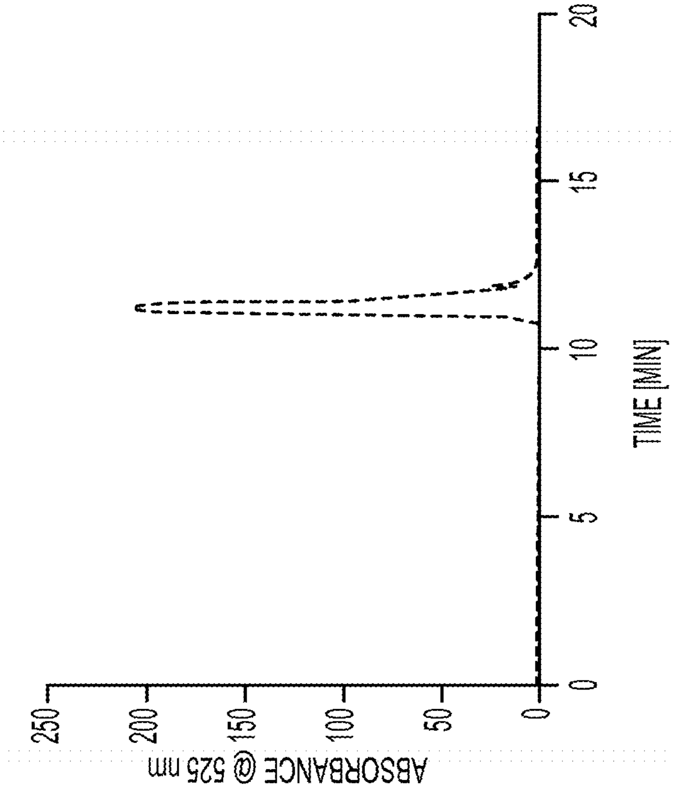
FIGS. 30A and 30B show radioactivity (FIG. 30A) and UV (FIG. 30B) traces of the radio-HPLC analysis of the radioligand Tz-PEG$_{11}$-Al[$^{18}$F]-NOTA.
Figure 30A:
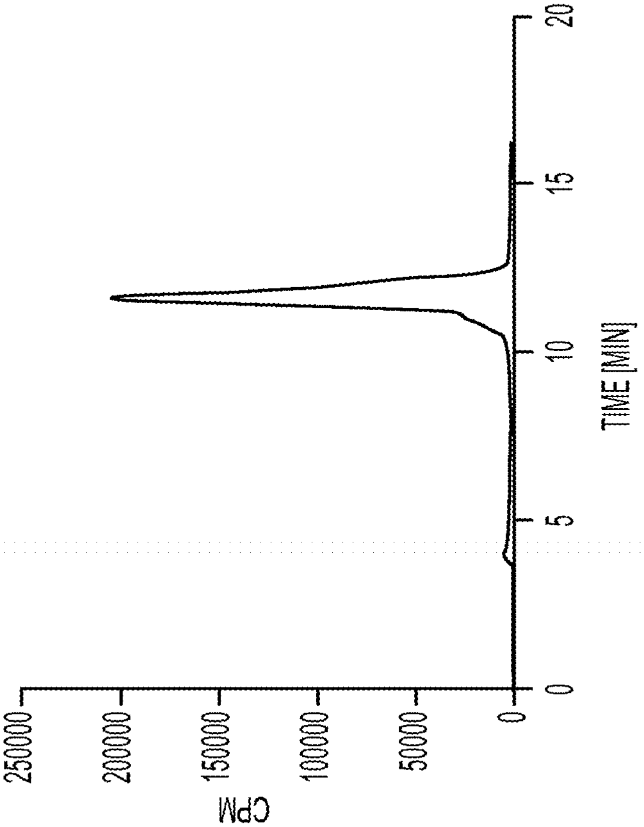

The radioligand was incubated with agitation (600 rpm) at 37° C. in 500 μL of either PBS or human serum. At the appropriate time points, 100 μL of the solution was transferred into a 1.7 mL centrifuge tube. In case of PBS, the aliquot was directly injected into the HPLC. For the serum samples, 100 μL of MeCN was added to the previously transferred 100 μL serum solution and the resulting solution was vortexed and centrifuged (13,000 rpm) for 5 min. The clear supernatant was removed, moved to a new centrifuge tube followed by additional centrifugation at 13,000 rpm for 5 min. The resulting clear supernatant was then used for HPLC analysis (FIGS. 30A and 30B). The residual protein was checked for radioactivity, and only minimal residual radioactivity could be detected (e.g., less than 2%). The fraction of intact radioligand was calculated by dividing the peak area corresponding to the tracer by the integral of the entire HPLC run. The observed decomposition of the radioligand in human serum is likely related to the presence of nucleophilic sulfhydryl and amino groups in the serum that could, even at neutral pH, have a measurable negative effect on the stability of the tetrazine radioligand.

Click Reaction of $Tz-PEG_{11}$-Al[18F]-NOTA with TCO-modified 5B1

Figure 31B:
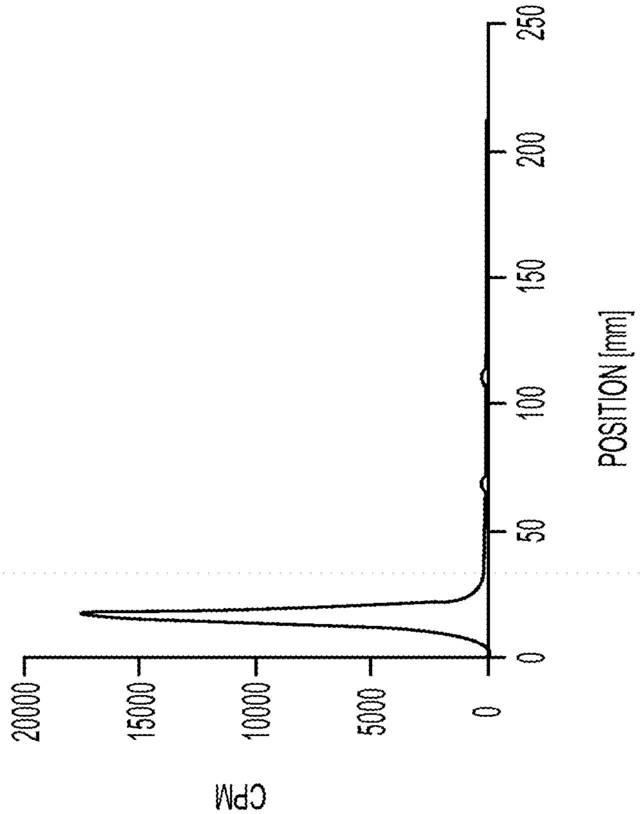
FIGS. 31A and 31B show radio-TLC diagrams using 90% MeCN in $H_2O$ as mobile phase showing free radioligand (FIG. 31A) and the click reaction product after 15 min incubation (FIG. 31B) at room temperature of the radioligand with TCO-modified 5B1. The results indicated that the click reaction is complete after 15 min (n=3).
Figure 31A:
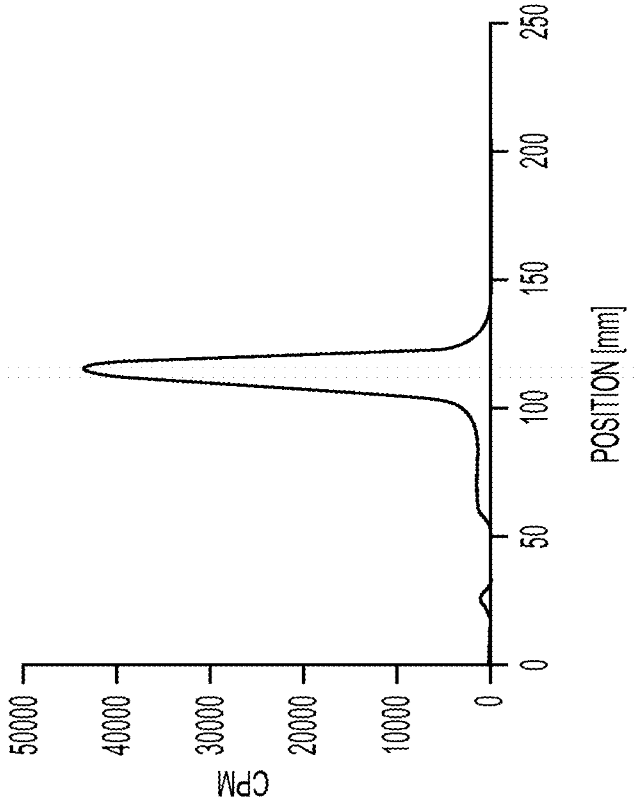

The click reaction between the radioligand and the TCO moiety of the TCO-modified 5B1 antibody was demonstrated by incubating an equimolar amount (1.33 nmol) of the purified tracer [18F]2 with 5B1-TCO in PBS (pH=7.4) at room temperature for 15 min. A small aliquot of the reaction mixture was spotted onto a C18 TLC plate. TLC was performed using 90% MeCN in $H_2O$ as mobile phase and analyzed by radio-TLC. The free radioligand in a control run could be detected at the solvent front (FIG. 31A) whereas the 18F-labeled click reaction product (FIG. 31B) was situated at the origin showing that the click reaction was completed after 15 min.

Cell Culture

BxPC3 cells were purchased from ATCC (Manassas, VA) and grown in RPMI modified to contain 4.5 g/L glucose and 1.5 g/L sodium bicarbonate and supplemented with 10% (v/v) fetal calf serum, 10 mM HEPES, 1 mM sodium pyruvate, 2 mM L-glutamine, 10 cc/L non-essential amino acids, 100 IU penicillin and 100 ug streptomycin.

In Vivo Models

All animal experiments within this study were performed in accordance with protocols approved by the Institutional Animal Care and Use Committee of MSKCC and followed National Institutes of Health guidelines for animal welfare. Female athymic nude CrTac:NCr-Foxn1$^{nu}$ mice at age 6-8 weeks were purchased from Charles River Laboratories. For subcutaneous injections, mice were anesthetized with 2% isoflurane (Baxter Healthcare) (2 L/min medical air) before BxPC3 cells were implanted subcutaneously ($5\times10^6$ cells in 150 μL 1:1 growth media/Matrigel® (BD Biosciences, San Jose, CA) in the right shoulder and allowed to grow for approximately 3-4 weeks until the tumors reached 5-10 mm in size. For all intravenous injections, mice were gently warmed with a heat lamp and placed on a restrainer. The tails were sterilized with alcohol pads, and injection took place via the lateral tail vein.

Biodistribution in Healthy Nude Mice

Figure 32:
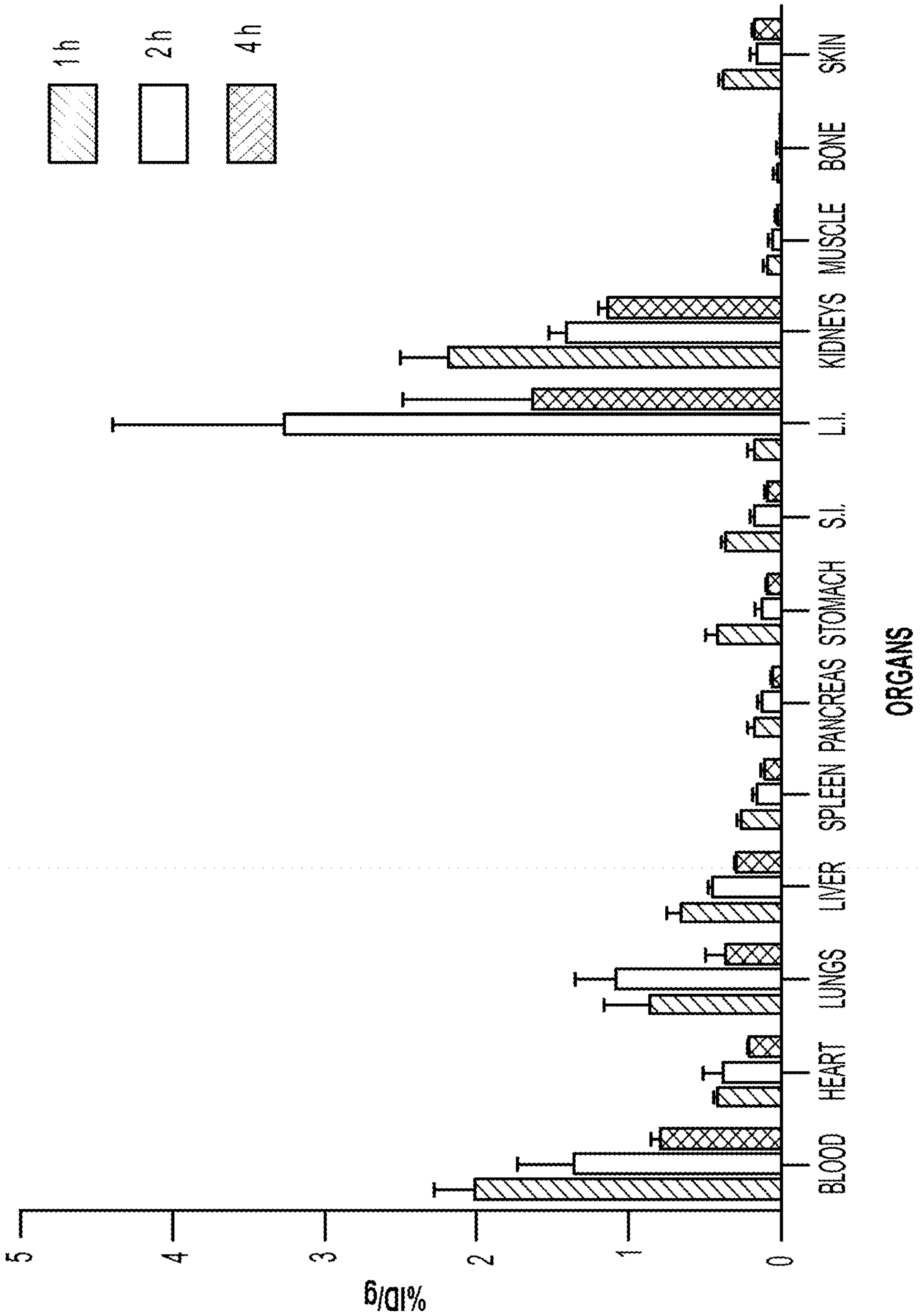
FIG. 32 shows biodistribution data of the radioligand obtained from healthy nude mice at 1, 2, and 4 h (n=4) after injection of the radioligand [$^{18}$F]2.

The radioligand $Tz-PEG_{11}$-Al18F-NOTA was injected into healthy mice via the tail vein (FIG. 32). The organs were harvested at the appropriate time points after the animals were euthanized by $CO_2$ asphyxiation. The collected organs were weighed and counted in a WIZARD$^2$ automatic 7-counter (PerkinElmer, Boston, MA). Generally, radioactivity was taken and retained in the intestines and kidneys. Blood pool clearance occurred slower than anticipated for small molecule radiotracer, however, the clearance pattern was in line with the determined blood half-life of 74.4 minutes.

The identical method was used in case of the pretargeted biodistribution experiments.

Blood Half-Life Determination of $Tz-PEG_{11}$-Al[18F]-NOTA

Figure 33:
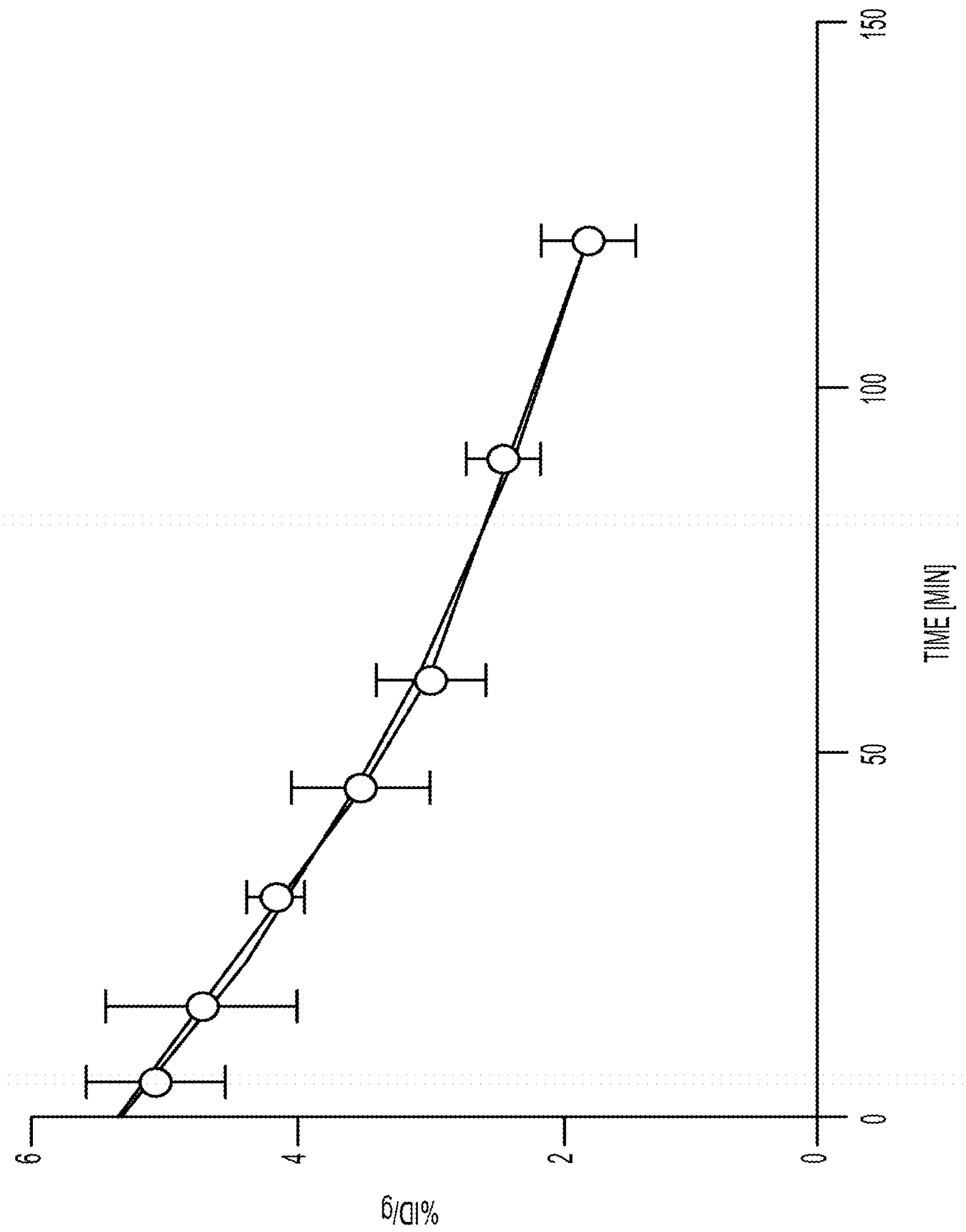
FIG. 33 shows the blood half-life of the radioligand was calculated by plotting the % ID/g of the collected blood samples for each time point (n=4) against the corresponding collection time points.

The tracer $Tz-PEG_{11}$-Al[8F]-NOTA ([18F]2) was injected into healthy nude mice via the tail vein. Blood was collected through the saphenous vein at the appropriate time points (FIG. 33). The collection tubes were weighed before and after blood collection and measured for radioactivity in order to calculate the percent injected dose per gram values for each time point and sample (n=4 for each time point). The half-life was subsequently calculated to 74.4 minutes.

Dosimetry

The pretargeted biodistribution data obtained from the utilized mouse model were first expressed as normal-organ mean standard uptake values (SUVs) versus time post-injection. It was assumed that SUVs are, in first order, independent of body mass and hence the same among species. The mean SUV in mouse organ in every mouse organ was then used to calculate the mean SUV of the same organs in a human using the organ and total-body masses of the 70 kg Standard Man anatomic model. These data were then corrected for radioactive decay to the time of injection and subsequently fitted to a mono-exponential or bi-exponential time-activity function, depending on the organ. This information was used to determine the organ residence times which were then entered into the OLINDA computer program to yield the mean organ absorbed doses and effective dose in rad/mCi and rem/mCi, respectively. The data obtained from the herein presented $^{18}$F-based pretargeting system were compared to the pretargeting system previously described by Viola-Villegas et al. using $^{89}$Zr-labeled 5B1 for pretargeting CA19.9 (Table 25).

Table 25 shows mean organ absorbed doses and effective dose calculated for the herein described pretargeting approach given in rad/mCi and rem/mCi, respectively, compared to the pretargeting system previously by N. T. Vioia-Villegas, S. L. Rice, S. Carlin, X. Wu, M. J. Evans, K. K. Sevak, M. Drobjnak, G. Ragupathi, R. Sawada, W. W. Scholz, P. O. Livingston, J. S. Lewis, *J Nucl. Med,* 2013, 54, 1876-1882. using $^{89}$Zr-labeled 5B1 for pretargeting CA19.9.

TABLE 25

| Target Organ | $^{18}$F pretargeting | $^{89}$Zr-DFO-5B1# |
|---|---|---|
| Adrenals | 0.0288 | 2.22 |
| Brain | 0.0256 | 1.7 |
| Breasts | 0.0214 | 1.36 |
| Gallbladder Wall | 0.0297 | 2.13 |
| LH Wall | 0.0487 | 2.22 |
| Small Intestine | 0.0356 | 2.1 |
| Stomach Wall | 0.0401 | 2.2 |
| UH Wall | 0.0424 | 1.98 |
| Heart Wall | 0.0279 | 2.15 |
| Kidneys | 0.113 | 2.86 |
| Liver | 0.0223 | 2.52 |
| Lungs | 0.0181 | 2.52 |
| Muscle | 0.0138 | 1.59 |
| Ovaries | 0.0299 | 1.98 |
| Pancreas | 0.0327 | 2.26 |
| Red Marrow | 0.0227 | 4.01 |
| Osteogenic Cells | 0.0366 | 5.08 |
| Skin | 0.018 | 1.17 |
| Spleen | 0.0997 | 3.7 |
| Testes | 0.0233 | 1.51 |
| Thymus | 0.0234 | 1.71 |
| Thyroid | 0.0235 | 1.69 |
| Urinary Bladder Wall | 0.0286 | 1.86 |
| Uterus | 0.0306 | 1.99 |
| Total Body | 0.0235 | 1.86 |
| Effective dose | 0.0302 | 2.02 |

Exemplary Tetrazine Precursors Available for Radiolabeling with $^{18}$F

Below are listed examples of available tetrazine-based precursor molecules that can be used for radiolabeling with $^{18}$F using the Al[$^{18}$F]-NOTA methodology.

Tetrazine Structures Connected to NOTA-Chelators Via PEG-Linkers:

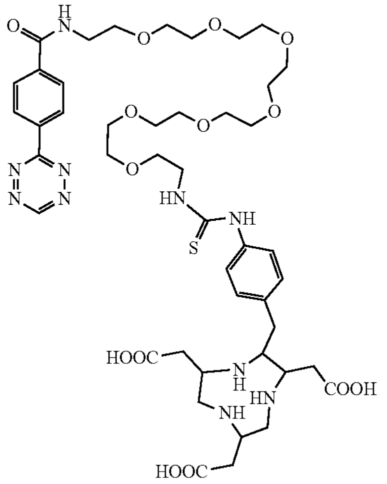

2,2′,2″-(3-(4-(3-(1-(4-(1,2,4,5-tetrazin-3-yl)phenyl)-1-oxo-5,8,11,14,17,20,23-heptaoxa-2-azapentacosan-25-yl)thioureido)benzyl)-1,4,7-triazonane-2,5,8-triyl)triacetic acid Chemical Formula: $C_{45}H_{66}N_{10}O_{14}S$
Molecular Weight: 1003.13900

-continued
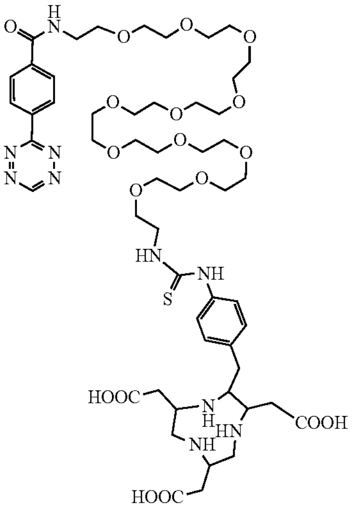
2,2′,2″,-(3-(4-(3-(1-(4-(1,2,4,5-tetrazin-3-yl)phenyl)-1-oxo-5,8,11,14,17,20,23,26,29,32,35-undecaoxa-2-azaheptatriacontan-37-yl)thioureido)benzyl)-1,4,7-triazonane-2,5,8-triyl)triacetic acid
Chemical Formula: $C_{53}H_{82}N_{10}O_{18}S$
Molecular Weight: 1179.35100
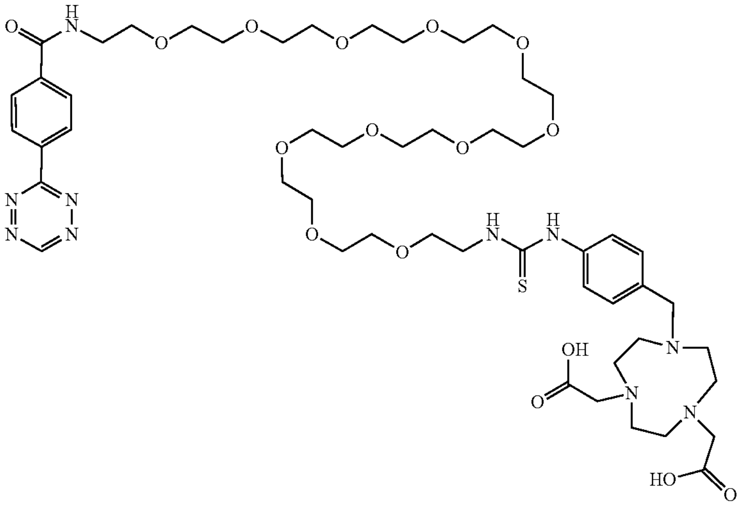
2,2′-(7-(4-(3-(1-(4-(1,2,4,5-tetrazin-3-yl)phenyl)-1-oxo-5,8,11,14,17,20,23,26,29,32,35-undecaoxa-2-azaheptatriacontan-37-yl)thioureido)benzyl)-1,4,7-triazonane-1,4-diyl)diacetic acid
Chemical Formula: $C_{51}H_{80}N_{10}O_{16}S$
Molecular Weight: 1121.32

-continued
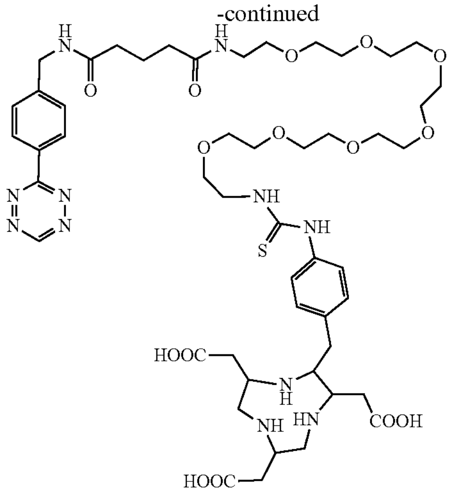
2,2′,2″-(3-(4-(3-(1-(4-(1,2,4,5-tetrazin-3-yl)phenyl)-3,7-dioxo-11,14,17,20,23,26,29-heptaoxa-2,8-diazahentriacontan-31-yl)thioureido)benzyl)-1,4,7-triazonane-2,5,8-triyl)triacetic acid
Chemical Formula: $C_{50}H_{75}N_{11}O_{15}S$
Molecular Weight: 1102.27200
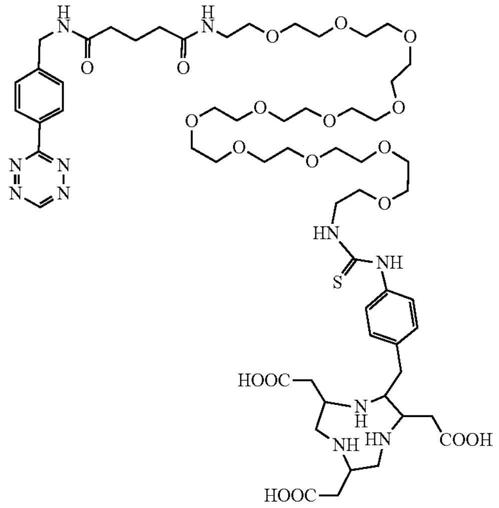
2,2′,2″-(3-(4-(3-(1-(4-(1,2,4,5-tetrazin-3-yl)phenyl)-3,7-dioxo-11,14,17,20,23,26,29,32,35,38,41-undecaoxa-2,8-diazatritetracontan-43-yl)thioureido)benzyl)-1,4,7-triazonane-2,5,8-triyl)triacetic acid
Chemical Formula: $C_{58}H_{91}N_{11}O_{19}S$
Molecular Weight: 1278.48400

-continued
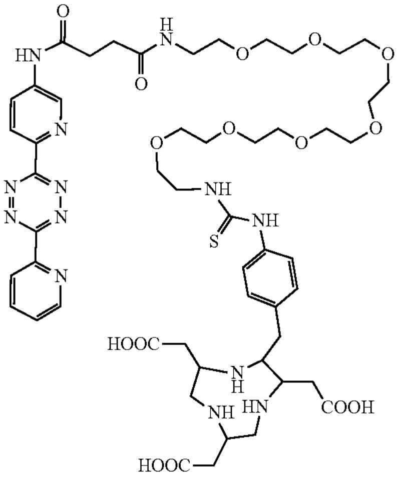
2,2′,2″-(3-(4-(3-(25,28-dioxo-28-((6-(6-(pyridin-2-yl)-1,2,4,5-tetrazin-3-yl)pyridin-3-yl)amino)-3,6,9,12,18,21-heptaoxa-24-azaoctacosyl)thioureido)benzyl)1,4,7-triazonane-2,5,8-triyl)triacetic acid
Chemical Formula: $C_{52}H_{73}N_{13}O_{15}S$
Molecular Weight: 1152.29200
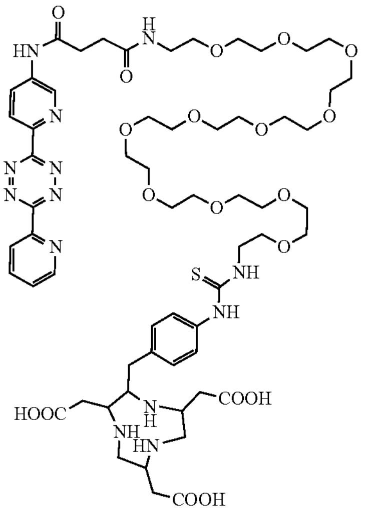
2,2′,2″-(3-(4-(3-(37,40-dioxo-40-((6-(6-(pyridin-2-yl)-1,2,4,5-tetrazin-3-yl)pyridin-3-yl)amino)-3,6,9,12,15,18,21,24,27,30,33-undecaoxa-36-azatetracontyl)thioureido)benzyl)-1,4,7-triazonane-2,5,8-triyl)triacetic acid
Chemical Formula: $C_{60}H_{89}N_{13}O_{19}S$
Molecular Weight: 1328.50400

-continued
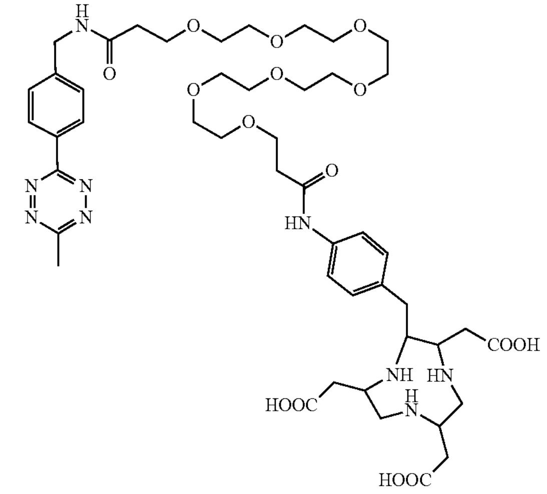
2,2′,2″-(3-(4-(1-(4-(6-methyl-1,2,4,5-tetrazin-3-yl)phenyl)-3-oxo-6,9,12,15,18,21,24-heptaoxa-2-azaheptacosan-27-amido)benzyl)-1,4,7-triazonane-2,5,8-triyl)triacetic acid
Chemical Formula: $C_{47}H_{69}N_9O_{15}$
Molecular Weight: 1000.1200
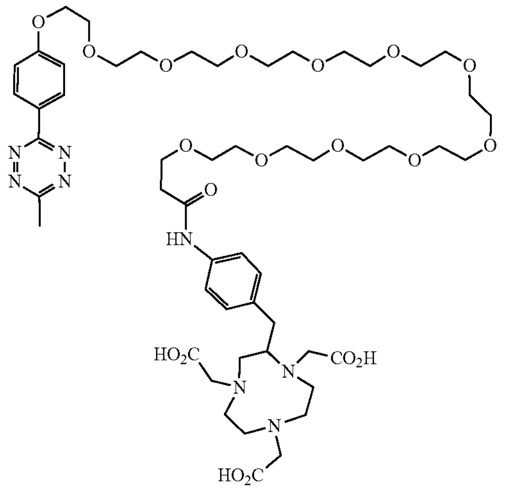
2,2′,2″-(2-(4-(1-(4-(6-methyl-1,2,4,5-tetrazin-3-yl)phenoxy)-3,6,9,12,15,18,21,24,27,30,33-undecaoxahexatriacontan-36-amido)benzyl)-1,4,7-triazonane-1,4,7-triyl)triacetic acid
Chemical Formula: $C_{55}H_{86}N_8O_{20}$
Molecular Weight: 1179.3300

Tetrazine Structures Connected to NOTA/NODA-Chelators Via (Poly)-L-Lysine-Linkers:

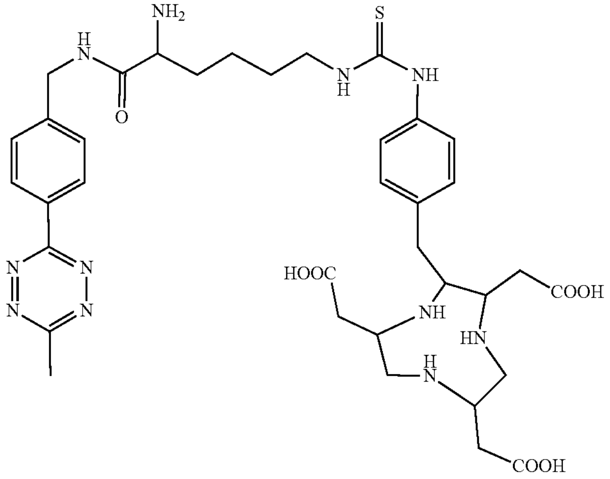

2,2′,2″-(3-(4-(3-(5-amino-6-((4-(6-methyl-1,2,4,5-tetrazin-3-yl)benzyl)amino)-6-oxohexyl)thioureido)benzyl)-1,4,7-triazonane-2,5,8-triyl)triacetic acid Chemical Formula: $C_{36}H_{49}N_{11}O_7S$
Molecular Weight: 779.91800

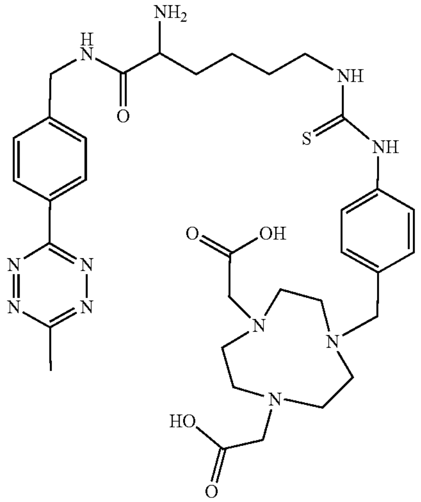

2,2′-(7-(4-(3-(5-amino-6-((4-(6-methyl-1,2,4,5-tetrazin-3-yl)benzyl)amino)-6-oxohexyl)thioureido)benzyl)-1,4,7-triazonane-1,4-diyl)diacetic acid Chemical Formula: $C_{34}H_{47}N_{11}O_5O$
Molecular Weight: 721.88200

-continued

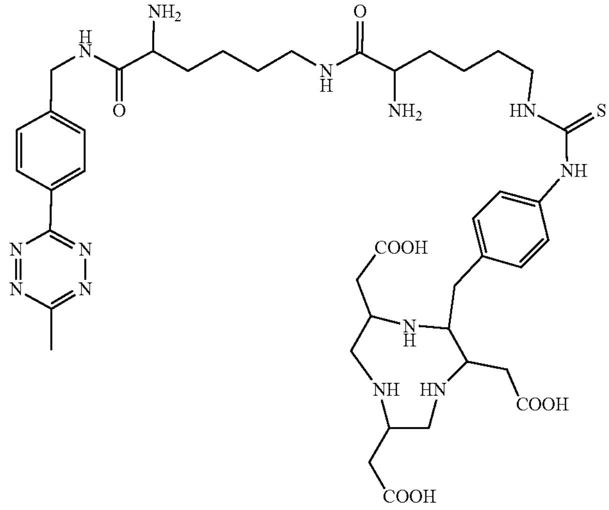

2,2′,2″-(3-(4-(3-(5-amino-6-((5-amino-6-((4-(6-methyl-1,2,4,5-tetrazin-3-yl)benzyl)amino)-6-oxohexyl)amino)-6-oxohexyl)thioureido)benzyl)-1,4,7-triazonane-2,5,8-triyl)triacetic acid Chemical Formula: $C_{42}H_{61}N_{13}O_8S$
Molecular Weight: 908.0900

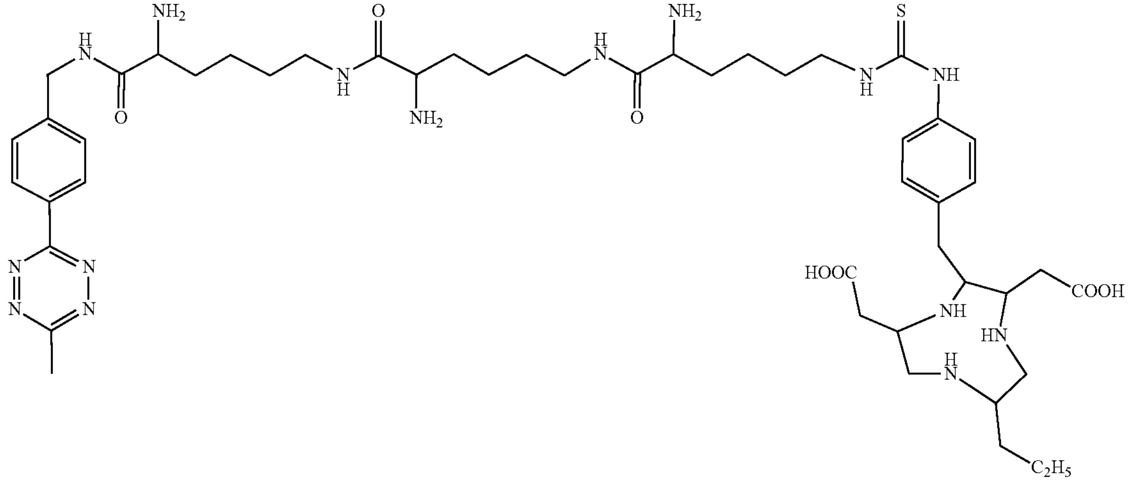

2,2′,2″-(3-(4-(3-(5-amino-6-((5-amino-6-((5-amino-6-((4-(6-methyl-1,2,4,5-tetrazin-3-yl)benzyl)amino)-6-oxohexyl)amino)-6-oxohexyl)amino)-6-oxohexyl)thioureido)benzyl)-1,4,7-triazonane-2,5,8-triyl)triacetic acid Chemical Formula: $C_{48}H_{73}N_{15}O_9S$
Molecular Weight: 1036.26800

What is claimed is:

1. A composition comprising:

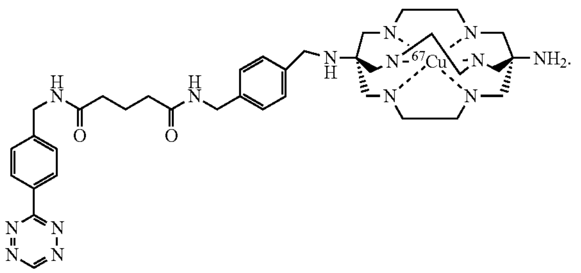

2. A radioimmunoconjugate comprising:

(1) a targeting moiety-transcyclooctene (TCO) conjugate; and (2) a radioligand comprising the composition of claim 1.

3. The radioimmunoconjugate of claim 2, wherein the targeting moiety-TCO conjugate has a TCO moiety comprising:

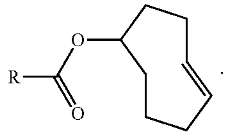

R = N, C

4. A method for detecting tumor cells, the method comprising:

(a) administering a quantity of targeting moiety-transcyclooctene (TCO) conjugate to a subject, wherein a portion of the targeting moiety-TCO conjugate localizes at the tumor cells and unbound targeting moiety-TCO conjugate is cleared from blood, from renal system, and/or from the subject after an accumulation interval;

(b) administering a radioligand to the subject after the accumulation interval, wherein the radioligand comprises the composition of claim 1, wherein the targeting moiety-TCO conjugate and the radioligand bind together to form a radioimmunoconjugate via an in vivo click reaction at the tumor cells within a region of the subject; and (c) imaging via positron emission tomography (PET) imaging the radioimmunoconjugate accumulated in the region of the subject within a time period less than 9 hours from the administering of the radioligand.

5. The method of claim 4, wherein the targeting moiety-TCO conjugate has a TCO moiety comprising:

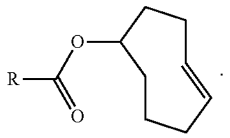

R = N, C

6. The method of claim 4, wherein the tumor cells are colorectal tumor cells or pancreatic tumor cells.

* * * * *